US012188019B2

(12) United States Patent
Bataller Alberola et al.

(10) Patent No.: US 12,188,019 B2
(45) Date of Patent: Jan. 7, 2025

(54) SILENCING OF HNF4α-P2 ISOFORMS WITH SIRNA TO IMPROVE HEPATOCYTE FUNCTION IN LIVER FAILURE

(71) Applicant: University of Pittsburgh—Of the Commonwealth System of Higher Education, Pittsburgh, PA (US)

(72) Inventors: Ramon Bataller Alberola, Pittsburgh, PA (US); Jose Maria Argemi Ballbe, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 672 days.

(21) Appl. No.: 17/144,365

(22) Filed: Jan. 8, 2021

(65) Prior Publication Data

US 2021/0147852 A1    May 20, 2021

Related U.S. Application Data

(62) Division of application No. 16/670,122, filed on Oct. 31, 2019, now Pat. No. 10,913,951.

(60) Provisional application No. 62/757,944, filed on Nov. 9, 2018, provisional application No. 62/753,299, filed on Oct. 31, 2018.

(51) Int. Cl.
*C12N 15/113* (2010.01)

(52) U.S. Cl.
CPC ...... *C12N 15/1138* (2013.01); *C12N 2310/14* (2013.01)

(58) Field of Classification Search
CPC ............ C12N 15/1138; C12N 2310/14; C12N 2310/315; C12N 15/113
USPC ...................... 435/6.1, 91.1, 91.31, 455, 458; 514/44 A; 536/23.1, 24.5
See application file for complete search history.

(56) References Cited

U.S. PATENT DOCUMENTS

| | | |
|---|---|---|
| 3,687,808 A | 8/1972 | Merigan, Jr. |
| 4,469,863 A | 9/1984 | Tso et al. |
| 4,476,301 A | 10/1984 | Imbach et al. |
| 4,587,044 A | 5/1986 | Miller et al. |
| 4,605,735 A | 8/1986 | Miyoshi |
| 4,667,025 A | 5/1987 | Miyoshi |
| 4,762,779 A | 8/1988 | Snitman |
| 4,789,737 A | 12/1988 | Miyoshi |
| 4,824,941 A | 4/1989 | Gordon et al. |
| 4,828,979 A | 5/1989 | Klevan et al. |
| 4,835,263 A | 5/1989 | Nguyen et al. |
| 4,837,028 A | 6/1989 | Allen |
| 4,845,205 A | 7/1989 | Dinh et al. |
| 4,876,335 A | 10/1989 | Yamane et al. |
| 4,897,355 A | 1/1990 | Eppstein et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,023,243 A | 6/1991 | Tullis |
| 5,032,401 A | 7/1991 | Jamas et al. |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,134,066 A | 7/1992 | Rogers et al. |
| 5,138,045 A | 8/1992 | Cook et al. |
| 5,171,678 A | 12/1992 | Behr et al. |
| 5,175,273 A | 12/1992 | Bischofberger et al. |
| 5,214,136 A | 5/1993 | Lin et al. |
| 5,218,105 A | 6/1993 | Cook et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,272,250 A | 12/1993 | Spielvogel et al. |
| 5,283,185 A | 2/1994 | Epand et al. |
| 5,292,873 A | 3/1994 | Rokita et al. |
| 5,317,098 A | 5/1994 | Shizuya et al. |
| 5,319,080 A | 6/1994 | Leumann |
| 5,359,044 A | 10/1994 | Cook et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |

(Continued)

FOREIGN PATENT DOCUMENTS

CN    102304515    *   1/2012    ......... C12N 2310/13
WO    8804924 A1    7/1988

(Continued)

OTHER PUBLICATIONS

Adzhubei, et al., "A method and server for predicting damaging missense mutations", Nat Methods, 2010, vol. 7, pp. 248-249.

(Continued)

*Primary Examiner* — Jane J Zara

(74) *Attorney, Agent, or Firm* — The Webb Law Firm

(57) ABSTRACT

Provided herein are antisense agents for knocking down, inhibiting, or silencing expression of an HNF4α-P2 isoform mRNA in a cell or a patient. Also provided are methods of knocking down, inhibiting, or silencing expression of an HNF4α-P2 isoform mRNA in a cell or a patient and methods of treating a patient with liver disease, liver damage, liver inflammation, or liver failure, such as acute liver failure, ALD, AH, or ACLF.

7 Claims, 20 Drawing Sheets

Specification includes a Sequence Listing.

(56) References Cited

U.S. PATENT DOCUMENTS

| | | |
|---|---|---|
| 5,414,077 A | 5/1995 | Lin et al. |
| 5,416,203 A | 5/1995 | Letsinger |
| 5,432,272 A | 7/1995 | Benner |
| 5,446,137 A | 8/1995 | Maag et al. |
| 5,451,463 A | 9/1995 | Nelson et al. |
| 5,457,187 A | 10/1995 | Gmeiner et al. |
| 5,459,255 A | 10/1995 | Cook et al. |
| 5,466,786 A | 11/1995 | Buhr et al. |
| 5,484,908 A | 1/1996 | Froehler et al. |
| 5,486,603 A | 1/1996 | Buhr |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,134 A | 5/1996 | Acevedo et al. |
| 5,525,465 A | 6/1996 | Haralambidis et al. |
| 5,525,711 A | 6/1996 | Hawkins et al. |
| 5,541,313 A | 7/1996 | Ruth |
| 5,543,152 A | 8/1996 | Webb et al. |
| 5,545,730 A | 8/1996 | Urdea et al. |
| 5,552,538 A | 9/1996 | Urdea et al. |
| 5,552,540 A | 9/1996 | Haralambidis |
| 5,565,552 A | 10/1996 | Magda et al. |
| 5,567,810 A | 10/1996 | Weis et al. |
| 5,567,811 A | 10/1996 | Misiura et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,608,046 A | 3/1997 | Cook et al. |
| 5,610,300 A | 3/1997 | Altmann et al. |
| 5,614,617 A | 3/1997 | Cook et al. |
| 5,627,053 A | 5/1997 | Usman et al. |
| 5,639,873 A | 6/1997 | Barascut et al. |
| 5,646,265 A | 7/1997 | McGee |
| 5,658,873 A | 8/1997 | Bertsch-Frank et al. |
| 5,670,633 A | 9/1997 | Cook et al. |
| 5,681,941 A | 10/1997 | Cook et al. |
| 5,688,941 A | 11/1997 | Cook et al. |
| 5,700,920 A | 12/1997 | Altmann et al. |
| 5,750,692 A | 5/1998 | Cook et al. |
| 5,976,567 A | 11/1999 | Wheeler et al. |
| 5,981,501 A | 11/1999 | Wheeler et al. |
| 6,015,886 A | 1/2000 | Dale et al. |
| 6,147,200 A | 11/2000 | Manoharan et al. |
| 6,166,197 A | 12/2000 | Cook et al. |
| 6,191,105 B1 | 2/2001 | Ekwuribe et al. |
| 6,222,025 B1 | 4/2001 | Cook et al. |
| 6,235,887 B1 | 5/2001 | Froehler et al. |
| 6,268,490 B1 | 7/2001 | Imanishi et al. |
| 6,294,664 B1 | 9/2001 | Ravikumar et al. |
| 6,320,017 B1 | 11/2001 | Ansell |
| 6,380,368 B1 | 4/2002 | Froehler et al. |
| 6,525,191 B1 | 2/2003 | Ramasamy |
| 6,528,640 B1 | 3/2003 | Beigelman et al. |
| 6,534,484 B1 | 3/2003 | Wheeler et al. |
| 6,576,752 B1 | 6/2003 | Manoharan et al. |
| 6,586,410 B1 | 7/2003 | Wheeler et al. |
| 6,617,438 B1 | 9/2003 | Beigelman et al. |
| 6,639,062 B2 | 10/2003 | Manoharan et al. |
| 6,670,461 B1 | 12/2003 | Wengel et al. |
| 6,747,014 B2 | 6/2004 | Teng et al. |
| 6,770,748 B2 | 8/2004 | Imanishi et al. |
| 6,783,931 B1 | 8/2004 | Cook et al. |
| 6,794,499 B2 | 9/2004 | Wengel et al. |
| 6,815,432 B2 | 11/2004 | Wheeler et al. |
| 6,887,906 B1 | 5/2005 | Teng et al. |
| 6,900,297 B1 | 5/2005 | Cook et al. |
| 6,998,484 B2 | 2/2006 | Koch et al. |
| 7,034,133 B2 | 4/2006 | Wengel et al. |
| 7,037,646 B1 | 5/2006 | Cook et al. |
| 7,045,610 B2 | 5/2006 | Dempcy et al. |
| 7,053,207 B2 | 5/2006 | Wengel |
| 7,063,860 B2 | 6/2006 | Chancellor et al. |
| 7,070,802 B1 | 7/2006 | Bhalani et al. |
| 7,084,125 B2 | 8/2006 | Wengel |
| 7,157,099 B2 | 1/2007 | Autuori et al. |
| 7,399,845 B2 | 7/2008 | Seth et al. |
| 7,427,672 B2 | 9/2008 | Imanishi et al. |
| 7,495,088 B1 | 2/2009 | Brakel et al. |
| 7,569,686 B1 | 8/2009 | Bhat et al. |
| 7,741,457 B2 | 6/2010 | Seth et al. |
| 8,022,193 B2 | 9/2011 | Seth et al. |
| 8,030,467 B2 | 10/2011 | Seth et al. |
| 8,106,022 B2 | 1/2012 | Manoharan et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,314,227 B2 | 11/2012 | Wengel |
| 2003/0027780 A1 | 2/2003 | Hardee et al. |
| 2004/0171570 A1 | 9/2004 | Allerson et al. |
| 2005/0137155 A1 | 6/2005 | McSwiggen |
| 2008/0039618 A1 | 2/2008 | Allerson et al. |
| 2009/0012281 A1 | 1/2009 | Swayze et al. |
| 2009/0023673 A1 | 1/2009 | Manoharan et al. |
| 2009/0215178 A1* | 8/2009 | Tang ............... C12N 15/111 435/455 |
| 2010/0324120 A1 | 12/2010 | Chen et al. |
| 2011/0313020 A1 | 12/2011 | Templin et al. |
| 2012/0157511 A1 | 6/2012 | Manoharan et al. |
| 2013/0011922 A1 | 1/2013 | Quay et al. |
| 2013/0096289 A1 | 4/2013 | Wengel |
| 2013/0190383 A1 | 7/2013 | Vaish et al. |
| 2013/0338215 A1* | 12/2013 | Lieberman ............ A61P 31/18 435/375 |
| 2017/0009304 A1* | 1/2017 | Zhuo ................ G16B 30/00 |
| 2019/0070213 A1 | 3/2019 | Aznarez et al. |
| 2019/0185819 A1 | 6/2019 | Soto-Gutierrez et al. |

FOREIGN PATENT DOCUMENTS

| | | |
|---|---|---|
| WO | 9116024 A1 | 10/1991 |
| WO | 9324640 A2 | 12/1993 |
| WO | 9400569 A1 | 1/1994 |
| WO | 9402595 A1 | 2/1994 |
| WO | 9637194 A1 | 11/1996 |
| WO | 9640964 A2 | 12/1996 |
| WO | 9914226 A2 | 3/1999 |
| WO | 0003683 A2 | 1/2000 |
| WO | 2013036868 A1 | 3/2013 |
| WO | 2014179620 A1 | 11/2014 |
| WO | 2014179627 A2 | 11/2014 |
| WO | 2016209862 A1 | 12/2016 |
| WO | WO-2017010950 A1 * | 1/2017 ........... A61K 31/713 |
| WO | 2017106283 A1 | 6/2017 |

OTHER PUBLICATIONS

Affo et al., "CCL20 mediates lipopolysaccharide induced liver injury and is a potential driver of inflammation and fibrosis in alcoholic hepatitis", Gut, 2014, vol. 63, pp. 1782-1792.

Affo et al., "Transcriptome analysis identifies TNF superfamily receptors as potential therapeutic targets in alcoholic hepatitis", Gut, 2013, vol. 62, pp. 452-460.

Altamirano, et al., "A histologic scoring system for prognosis of patients with alcoholic hepatitis", Gastroenterology, 2014, vol. 146, pp. 231-1239.

(56) References Cited

OTHER PUBLICATIONS

Apweiler, et al., "UniProt: the Universal Protein knowledgebase", Nucleic Acids Res., 2004 vol. 32, pp. D115-119.
Argemi, et al., "Defective HNF4a-dependent gene expression as a drive of hepatocellular failure in alcoholic hepatitis", Modified Nucleosides in Biochemistry, Biotechnology and Medicine, 2008, Herdewijn, P. ed. Wiley-VCH, 2008.
Aryee, et al., "Minfi: a flexible and comprehensive Bioconductor package for the analysis of Infinium DNA methylation microarrays", Bioinformatics, 2014, vol. 30, pp. 1363-1369.
Bala, et al., "The pro-inflammatoryeffects of miR-155 promote liver fibrosis and alcohol-induced steatohepatitis", J Hepatol, 2016, vol. 64, pp. 1378-1387.
Buch, et al., "A genome-wide association study confirms PNPLA3 and identifies TM6SF2 and MBOAT7 as risk loci for alcohol-related cirrhosis", Nat Genet, 2015, vol. 47, pp. 1443-1448.
Cardenas, et al., "TGF-beta induces global changes in DNA methylation during the epithelial-to-mesenchymal transition in ovarian cancer cells" Epigenetics, 2014, vol. 9, pp. 1461-1472.
Consortium, "The Genotype-Tissue Expression (GTEx) project", Nat Genet, 2013, vol. 45, pp. 580-585.
Corey, "Chemical modification: the key to clinical application of RNA interference?", J Clin Invest., 2017, vol. 117:12, pp. 3615-3622.
Culhane, et al., "MADE4: an R package for multivariate analysis of gene expression data", Bioinformatics, 2005, vol. 21, pp. 2789-2790.
De Leeuw, et a., "MAGMA: generalized gene-set analysis of GWAS data", PLoS Comput Biol, 2015, vol. 11, p. 1004219.
Dobin, et al., "STAR: ultrafast universal RNA-seq aligner", Bioinformatics, 2013, vol. 29, pp. 15-21.
Dubuquoy, et al., "Progenitor cell expansion and impaired hepatocyte regeneration in explanted livers from alcoholic hepatitis", Gut, 2015, vol. 64, pp. 949-1960.
Etrnst, et al., "STEM: a tool for the analysis of short time series gene expression data", BMC Bioinformatics, 2006, vol. 7, pp. 191.
Forrest et al., "Rescue liver transplantation for severe alcoholic hepatitis: arriving where we started?", Hepatology, 2013, vol. 57, pp. 10-12.
Fu, et al., "Peroxisome proliferator-activated receptor gamma inhibits transforming growth factor beta-induced connective tissue growth factor expression in human aortic smooth muscle cells by interfering with Smad3", J Biol Chem, 2001, vol. 276, pp. 45888-45894.
Hayhurst, et al., "Hepatocyte nuclear factor 4alpha (nuclear receptor 2A1) is essential for maintenance of hepatic gene expression and lipid homeostasis", Mol Cell Biol, 2001,vol. 21, pp. 1393-1403.
Hines, et al., "Recent advances in alcoholic liver disease III. Role of the innate immune response in alcoholic hepatitis", Am J Physiol Gastrointest Liver Physiol, 2004. vol. 287, pp. G310-G314.
Ho, et al., "oPOSSUM: integrated tools for analysis of regulatory motif over-representation", Nucleic Acids Res, 2007, vol. 35, pp. W245-W252.
Kleiner, et al., Design and validation of a histological scoring system for nonalcoholic fatty liver disease, Hepatology, 2005, vol. 41, pp. 1313-1321.
Kono, et al. "Development of an intragastric enteral model in the mouse: studies of alcohol-induced liver disease using knockout technology", J Hepatobiliary Pancreat Surg, 2000, vol. 7, pp. 395-400.
Kuo, et al., "A transcriptional hierarchy involved in mammalian cell-type specification", Nature, 1992, vol. 355, pp. 457-461.
Lackner, et al., "Histological parameters and alcohol abstinence determine long-term prognosis in patients with alcoholic liver disease", J Hepatol, 2017, vol. 66, pp. 610-618.
Li, et al., "RSEM: accurate transcript quantification from RNA-Seq data with or without a reference genome".BMC Bioinformatics, 2011, vol. 12, p. 323.
Liberzon, et al., "Molecular signatures database (MSigDB) 3.0", Bioinformatics, 2011. vol. 27, pp. 1739-1740.
Lima et al., Cell, 2012, vol. 150, pp. 883-894.
Louvet, et al., "The Lille model: a new tool for therapeutic strategy in patients with severe alcoholic hepatitis treated with steroid", Hepatology, 2007, vol. 45, pp. 1348-1354.
Mathurin, et al., "Early liver transplantation for severe alcoholic hepatitis", N Engl J Med, 2011,vol. 365, pp. 1790-1800.
Matsumura, et al., "Epigenetic suppression of the TGF-beta pathway revealed by ranscriptome profiling in ovarian cancer", Genome Res, 2011, vol. 21, pp. 74-82.
Modified Nucleosides in Biochemistry, Biotechnology and Medicine, Herdewijn, P. ed. Wiley-VCH, 2008.
Nishikawa, et al., "Resetting the transcription factor network reverses terminal chronic hepatic failure", J Clin Invest, 2015, vol. 125, pp. 1533-1544.
Odena, et al., "LPS-TLR4 Pathway Mediates Ductular Cell Expansion in Alcoholic Hepatitis", Sci Rep, 2016 vol. 6, p. 35610.
Pan, et al., "Transforming growth factor beta1 induces the expression of collagen type I by DNA methylation in cardiac fibroblasts", PLoS One, 2013, vol. 8, p. e60335.
Pertea, et al., "Transcript-level expression analysis of RNA-seq experiments with HISAT, StringTie and Ballgown", Nat Protoc , 2016, vol. 11, pp. 1650-1667.
Peters, et al., "De novo identification of differentially methylated regions in the human genome", Epigenetics Chromatin, 2015, vol. 8, p. 6.
Ritchie et al., "limma powers differential expression analyses for RNA-sequencing and microarray studies", Nucleic Acids Res, 2015, vol. 43, p. e47.
Sancho-Bru et al., "Liver progenitor cell markers correlate with liver damage and predict shortterm mortality in patients with alcoholic hepatitis", Hepatology, 2012, vol. 55, pp. 1931-1941.
Sanghvi, et al., "dsRNA Research and Applications" , CRC Press, Boca Raton, 1993, pp. 276-278.
Shen et al., "MATS: a Bayesian framework for flexible detection of differential alternative splicing from RNASeq data", Nucleic Acids Res, 2012, vol. 40, p. e61.
Shen et al., "rMATS: robust and flexible detection of differential alternative splicing from replicate RNA-Seq data", Proc Natl Acad Sci U S A. 2014, vol. 111, pp. E5593-E5601.
Sladek, et al., "Liver-enriched transcription factor HNF-4 is a novel member of the steroid hormone receptor superfamily", Genes Dev 4, 1990, pp. 2353-2365.
Spath, et al., "Hepatocyte nuclear factor 4 expression overcomes repression of the hepatic phenotype in dedifferentiated hepatoma cells", Mol Cell Biol, 1997, vol. 17, pp. 1913-1922.
Stickel, et al., "The genetics of alcohol dependence and alcohol-related liver disease", J Hepatol, 2017, vol. 66, pp. 195-211.
The Concise Encyclopedia Of Polymer Science And Engineering, pp. 858-859, Kroschwitz, J. L, ed. John Wiley & Sons, 1990.
Thurz, et al., "Prednisolone or pentoxifylline for alcoholic hepatitis", N Engl J Med, 2015, vol. 372, pp. 1619-1628.
Torres-Padilla, et al., "Developmentally regulated Nterminal variants of the nuclear receptor hepatocyte nuclear factor 4alpha mediate multiple interactions through coactivator and corepressor-histone deacetylase complexes", J Biol Chem, 2002, vol. 277, pp. 44677-44687.
Torres-Padilla, et al., "Effects of interactions of hepatocyte nuclear factor 4alpha isoforms with coactivators and corepressors are promoter-specific", FEBS Lett, 2003, vol. 539, pp. 19-23.
Torres-Padilla, et al., "Expression of HNF4alpha isoforms in mouse liver development is regulated by sequential promoter usage and constitutive 3' end splicing", Mech Dev, 2001, vol. 109, 13.
Uehara, et al., "The DEN and CCl4-Induced Mouse Model of Fibrosis and Inflammation-Associated Hepatocellular Carcinoma", Curr Protoc Pharmacol, 2014, vol. 66, 14 30 11-10.
Vaser et al., "SIFT missense predictions for genomes", Nat Protoc, 2016, vol. 11, pp. 1-9.
Watts, et al.,"Gene silencing by siRNAs and antisense oligonucleotides in the laboratory and the clinic" (2012) 226(2):365-379).
Wu, et al. "PPARgamma is essential for protection against nonalcoholic steatohepatitis", Gene Ther, 2010, vol. 17, pp. 790-798.
Yan, et al., "HiChIP: a high-throughput pipeline for integrative analysis of ChIP-Seq data", BMC Bioinformatics, 2014, vol. 15, 280.

(56) References Cited

OTHER PUBLICATIONS

Zhang, et al., "TGF-beta regulates DNA methyltransferase expression in prostate cancer, correlates with aggressive capabilities, and predicts disease recurrence", PLoS One, 2011, vol. 6, p. e25168.

Zhong, et al., "Purification of nanogram-range immunoprecipitated DNA in ChIP-seq application", BMC Genomics, 2017, vol. 18, p. 985.

* cited by examiner

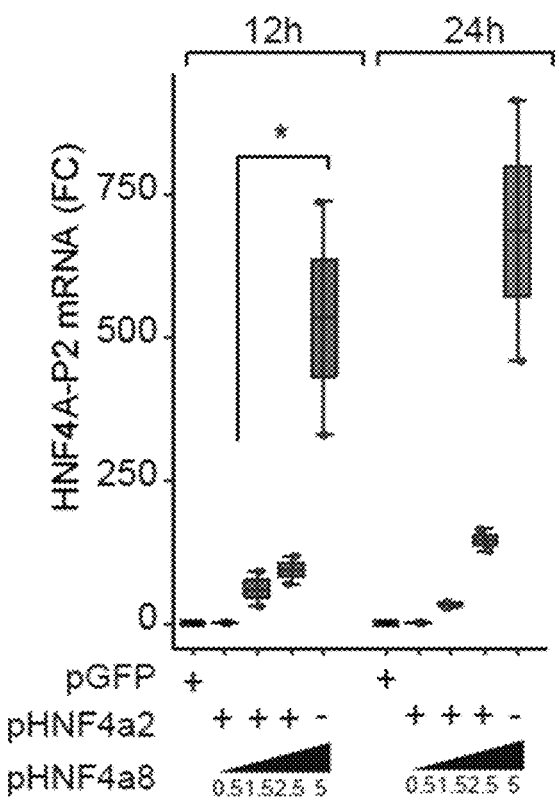
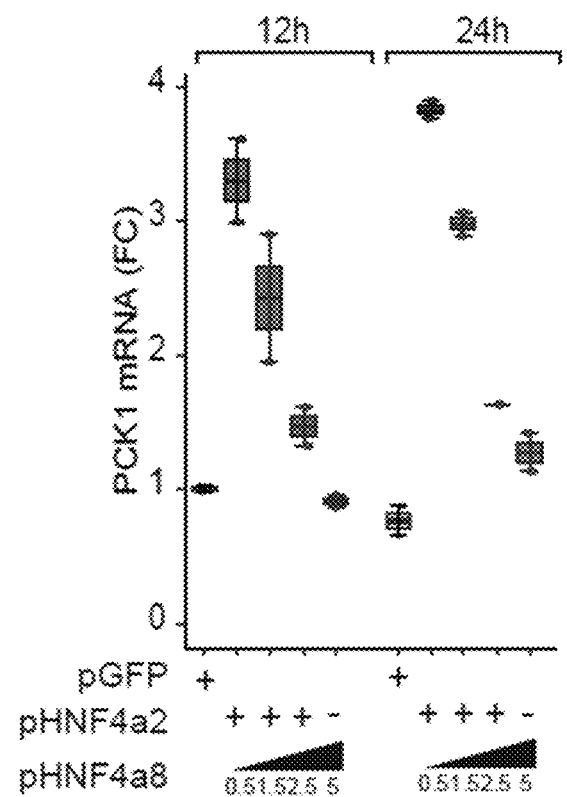
FIG. 2J
FIG. 2K
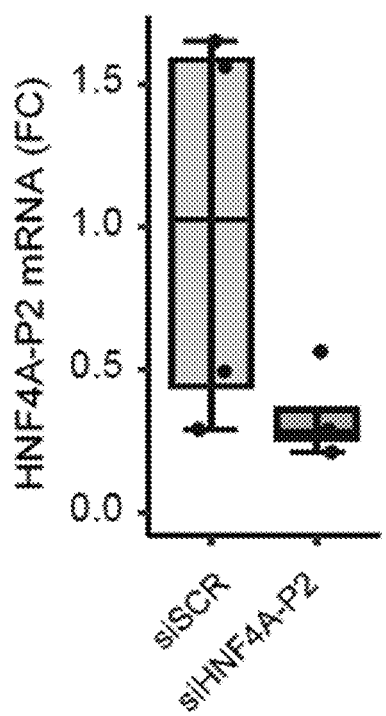
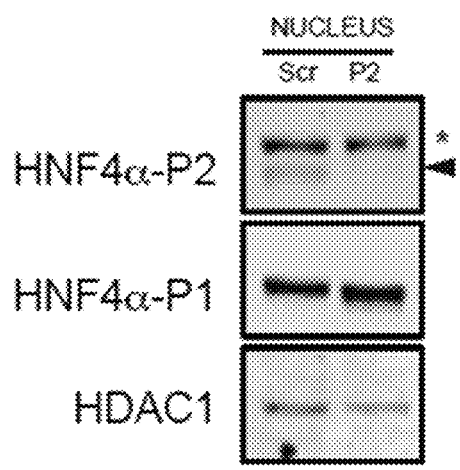
FIG. 2L
FIG. 2M

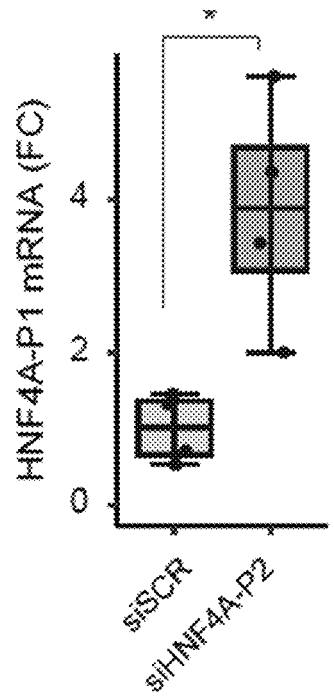 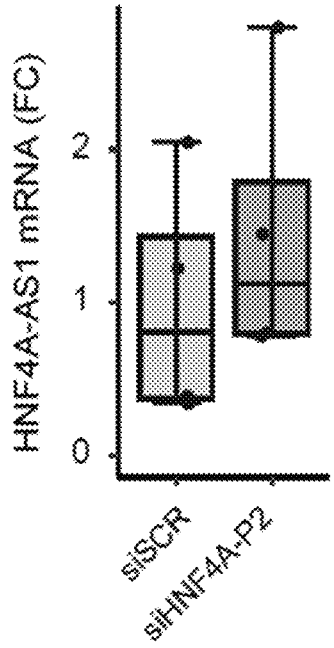
FIG. 2N        FIG. 2O
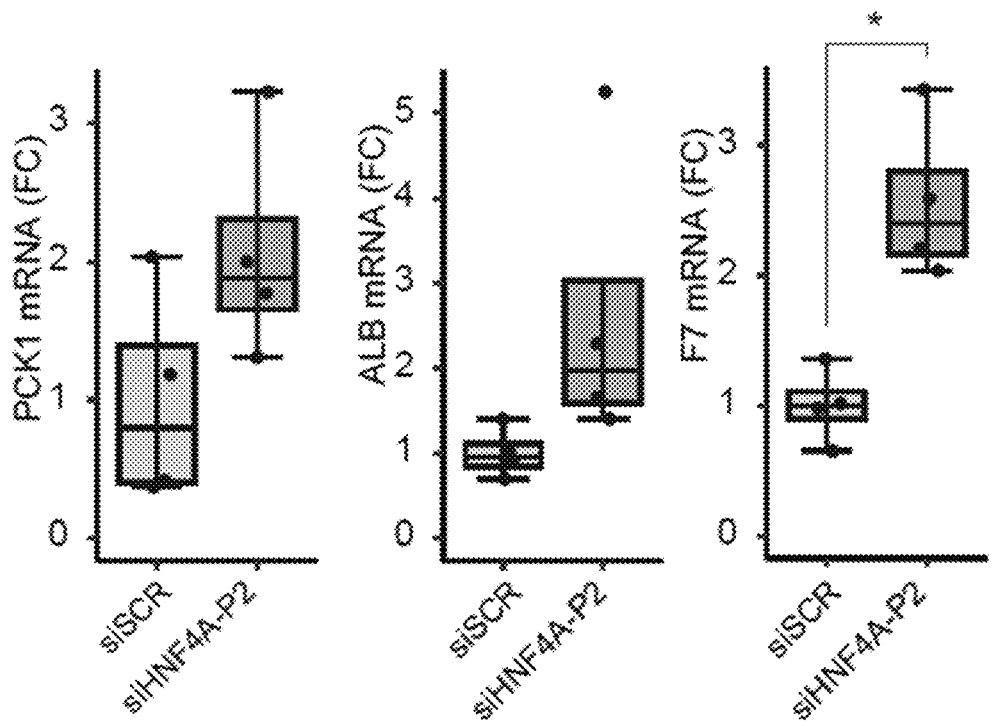
FIG. 2P

>NM_175914.4 Homo sapiens hepatocyte nuclear factor 4 alpha (HNF4A),
transcript variant 5, mRNA (SEQ ID NO: 1)
GGCCATGGTCAGCGTGAACGCGCCCCTCGGGGCTCCAGTGGAGAGTTCTTACGACACGTCCCCATCAGAA
GGCACCAACCTCAACGCGCCCAACAGCCTGGGTGTCAGCGCCCTGTGTGCCATCTGCGGGGACCGGGCCA
CGGGCAAACACTACGGTGCCTCGAGCTGTGACGGCTGCAAGGGCTTCTTCCGGAGGAGCGTGCGGAAGAA
CCACATGTACTCCTGCAGATTTAGCCGGCAGTGCGTGGTGGACAAAGACAAGAGGAACCAGTGCCGCTAC
TGCAGGCTCAAGAAATGCTTCCGGGCTGGCATGAAGAAGGAAGCCGTCCAGAATGAGCGGGACCGGATCA
GCACTCGAAGGTCAAGCTATGAGGACAGCAGCCTGCCCTCCATCAATGCGCTCCTGCAGGCGGAGGTCCT
GTCCCGACAGATCACCTCCCCCGTCTCCGGGATCAACGGCGACATTCGGGCGAAGAAGATTGCCAGCATC
GCAGATGTGTGTGAGTCCATGAAGGAGCAGCTGCTGGTTCTCGTTGAGTGGGCCAAGTACATCCCAGCTT
TCTGCGAGCTCCCCCTGGACGACCAGGTGGCCCTGCTCAGAGCCCATGCTGGCGAGCACCTGCTGCTCGG
AGCCACCAAGAGATCCATGGTGTTCAAGGACGTGCTGCTCCTAGGCAATGACTACATTGTCCCTCGGCAC
TGCCCGGAGCTGGCGGAGATGAGCCGGGTGTCCATACGCATCCTTGACGAGCTGGTGCTGCCCTTCCAGG
AGCTGCAGATCGATGACAATGAGTATGCCTACCTCAAAGCCATCATCTTCTTTGACCCAGATGCCAAGGG
GCTGAGCGATCCAGGGAAGATCAAGCGGCTGCGTTCCCAGGTGCAGGTGAGCTTGGAGGACTACATCAAC
GACCGCCAGTATGACTCGCGTGGCCGCTTTGGAGAGCTGCTGCTGCTGCTGCCCACCTTGCAGAGCATCA
CCTGGCAGATGATCGAGCAGATCCAGTTCATCAAGCTCTTCGGCATGGCCAAGATTGACAACCTGTTGCA
GGAGATGCTGCTGGGAGGGTCCCCCAGCGATGCACCCCATGCCCACCACCCCTGCACCCTCACCTGATG
CAGGAACATATGGGAACCAACGTCATCGTTGCCAACACAATGCCCACTCACCTCAGCAACGGACAGATGT
GTGAGTGGCCCCGACCCAGGGGACAGGCAGCCACCCTGAGACCCCACAGCCCTCACCGCCAGGTGGCTC
AGGGTCTGAGCCCTATAAGCTCCTGCCGGGAGCCGTCGCCACAATCGTCAAGCCCTCTCTGCCATCCCC
CAGCCGACCATCACCAAGCAGGAAGTTATCTAGCAAGCCGCTGGGGCTTGGGGGCTCCACTGGCTCCCCC
CAGCCCCCTAAGAGAGCACCTGGTGATCACGTGGTCACGGCAAAGGAAGACGTGATGCCAGGACCAGTCC
CAGAGCAGGAATGGGAAGGATGAAGGGCCCGAGAACATGGCCTAAGGCCACATCCCACTGCCACCCTTG
ACGCCCTGCTCTGGATAACAAGACTTTGACTTGGGGAGACCTCTACTGCCTTGGACAACTTTTCTCATGT
TGAAGCCACTGCCTTCACCTTCACCTTCATCCATGTCCAACCCCGACTTCATCCCAAAGGACAGCCGCC
TGGAGATGACTTGAGGCCTTACTTAAACCCAGCTCCCTTCTTCCCTAGCCTGGTGCTTCTCCTCTCCTAG
CCCCTGTCATGGTGTCCAGACAGAGCCCTGTGAGGCTGGGTCCAATTGTGGCACTTGGGGCACCTTGCTC
CTCCTTCTGCTGCTGCCCCACCTCTGCTGCCTCCCTCTGCTGTCACCTTGCTCAGCCATCCCGTCTTCT
CCAACACCACCTCTCCAGAGGCCAAGGAGGCCTTGGAAACGATTCCCCCAGTCATTCTGGGAACATGTTG
TAAGCACTGACTGGGACCAGGCACCAGGCAGGGTCTAGAAGGCTGTGGTGAGGGAAGACGCCTTTCTCCT
CCAACCCAACCTCATCCTCCTTCTTCAGGGACTTGGGTGGGTACTTGGGTGAGGATCCCTGAAGGCCTTC
AACCCGAGAAAACAAACCCAGGTTGGCGACTGCAACAGGAACTTGGAGTGGAGAGGAAAAGCATCAGAAA
GAGGCAGACCATCCACCAGGCCTTTGAGAAAGGGTAGAATTCTGGCTGGTAGAGCAGGTGAGATGGGACA
TTCCAAAGAACAGCCTGAGCCAAGGCCTAGTGGTAGTAAGAATCTAGCAAGAATTGAGGAAGAATGGTGT
GGGAGAGGGATGATGAAGAGAGAGAGGGCCTGCTGGAGAGCATAGGGTCTGGAACACCAGGCTGAGGTCC
TGATCAGCTTCAAGGAGTATGCAGGGAGCTGGCTTCCAGAAAATGAACACAGCAGTTCTGCAGAGGACG
GGAGGCTGGAAGCTGGGAGGTCAGGTGGGGTGGATGATATAATGCGGGTGAGAGTAATGAGGCTTGGGGC
TGGAGAGGACAAGATGGGTAAACCCTCACATCAGAGTGACATCCAGGAGGAATAAGCTCCCAGGGCCTGT
CTCAAGCTCTTCCTTACTCCCAGGCACTGTCTTAAGGCATCTGACATGCATCATCTCATTTAATCCTCCC
TTCCTCCCTATTAACCTAGAGATTGTTTTGTTTTTATTCTCCTCCTCCCTCCCCGCCCTCACCCGCCC
CACTCCCTCCTAACCTAGAGATTGTTACAGAAGCTGAAATTGCGTTCTAAGAGGTGAAGTGATTTTTTTT
CTGAAACTCACACAACTAGGAAGTGGCTGAGTCAGGACTTGAACCCAGGTCTCCCTGGATCAGAACAGGA
GCTCTTAACTACAGTGGCTGAATAGCTTCTCCAAAGGCTCCTGTGTTCTCACCGTGATCAAGTTGAGGG
GCTTCCGGCTCCTTCTACAGCCTCAGAAACCAGACTCGTTCTTCTGGGAACCCTGCCCACTCCCAGGAC
CAAGATTGGCCTGAGGCTGCACTAAAATTCACTTAGGGTCGAGCATCCTGTTTGCTGATAAATATTAAGG
AGAATTCATGACTCTTGACAGCTTTTCTCTCTTCACTCCCCAAGTCAAGGGGAGGGGTGGCAGGGGTCTG
TTTCCTGGAAGTCAGGCTCATCTGGCCTGTTGGCATGGGGGTGGGACAGTGTGCACAGTGTGGGGGCAGG

FIG. 4A

```
GGAGGGCTAAGCAGGCCTGGGTTTGAGGGCTGCTCCGGAGACCGTCACTCCAGGTGCATTCTGGAAGCAT
TAGACCCCAGGATGGAGCGACCAGCATGTCATCCATGTGGAATCTTGGTGGCTTTGAGGACATTCTGGAA
AATGCCACTGACCAGTGTGAACAAAAGGGATGTGTTATGGGGCTGGAGGTGTGATTAGGTAGGAGGGAAA
CTGTTGGACCGACTCCTGCCCCCTGCTCAACACTGACCCCTCTGAGTGGTTGGAGGCAGTGCCCCAGTGC
CCAGAAATCCCACCATTAGTGATTGTTTTTTATGAGAAAGAGGCGTGGAGAAGTATTGGGGCAATGTGTC
AGGGAGGAATCACCACATCCCTACGGCAGTCCCAGCCAAGCCCCCAATCCCAGCGGAGACTGTGCCCTGC
TCAGAGCTCCCAAGCCTTCCCCCACCACCTCACTCAAGTGCCCCTGAAATCCCTGCCAGACGGCTCAGCC
TGGTCTGCGGTAAGGCAGGGAGGCTGGAACCATTTCTGGGCATTGTGGTCATTCCCACTGTGTTCCTCCA
CCTCCTCCCTCCAGCGTTGCTCAGACCTCTGTCTTGGGAGAAAGGTTGAGATAAGAATGTCCCATGGAGT
GCCGTGGGCAACAGTGGCCCTTCATGGGAACAATCTGTTGGAGCAGGGGGTCAGTTCTCTGCTGGGAATC
TACCCCTTTCTGGAGGAGAAACCCATTCCACCTTAATAACTTTATTGTAATGTGAGAAACACAAAACAAA
GTTTACTTTTTTGACTCTAAGCTGACATGATATTAGAAAATCTCTCGCTCTCTTTTTTTTTTTTTTTTT
TTTTTTGGCTACTTGAGTTGTGGTCCTAAAACATAAAATCTGATGGACAAACAGAGGGTTGCTGGGGGGA
CAAGCGTGGGCACAATTTCCCCACCAAGACACCCTGATCTTCAGGCGGGTCTCAGGAGCTTCTAAAAATC
CGCATGGCTCTCCTGAGAGTGGACAGAGGAGAGGAGAGGGTCAGAAATGAACGCTCTTCTATTTCTTGTC
ATTACCAAGCCAATTACTTTTGCCAAATTTTTCTGTGATCTGCCCTGATTAAGATGAATTGTGAAATTTA
CATCAAGCAATTATCAAAGCGGGCTGGGTCCCATCAGAACGACCCACATCTTTCTGTGGGTGTGAATGTC
ATTAGGTCTTGCGCTGACCCCTGAGCCCCCATCACTGCCGCCTGATGGGGCAAAGAAACAAAAACATTT
CTTACTCTTCTGTGTTTTAACAAAAGTTTATAAAACAAAATAAATGGCGCATATGTTTTCTAAAAAAAAA
AAAAAAAA
```

FIG. 4B

>NM_001030003.2 Homo sapiens hepatocyte nuclear factor 4 alpha (HNF4A), transcript variant 4, mRNA (SEQ ID NO: 2)

```
GGCCATGGTCAGCGTGAACGCGCCCCTCGGGGCTCCAGTGGAGAGTTCTTACGACACGTCCCCATCAGAA
GGCACCAACCTCAACGCGCCCAACAGCCTGGGTGTCAGCGCCCTGTGTGCCATCTGCGGGGACCGGGCCA
CGGGCAAACACTACGGTGCCTCGAGCTGTGACGGCTGCAAGGGCTTCTTCCGGAGGAGCGTGCGGAAGAA
CCACATGTACTCCTGCAGATTTAGCCGGCAGTGCGTGGTGGACAAAGACAAGAGGAACCAGTGCCGCTAC
TGCAGGCTCAAGAAATGCTTCCGGGCTGGCATGAAGAAGGAAGCCGTCCAGAATGAGCGGGACCGGATCA
GCACTCGAAGGTCAAGCTATGAGGACAGCAGCCTGCCCTCCATCAATGCGCTCCTGCAGGCGGAGGTCCT
GTCCCGACAGATCACCTCCCCCGTCTCCGGGATCAACGGCGACATTCGGGCGAAGAAGATTGCCAGCATC
GCAGATGTGTGTGAGTCCATGAAGGAGCAGCTGCTGGTTCTCGTTGAGTGGGCCAAGTACATCCCAGCTT
TCTGCGAGCTCCCCCTGGACGACCAGGTGGCCCTGCTCAGAGCCCATGCTGGCGAGCACCTGCTGCTCGG
AGCCACCAAGAGATCCATGGTGTTCAAGGACGTGCTGCTCCTAGGCAATGACTACATTGTCCCTCGGCAC
TGCCCGGAGCTGGCGGAGATGAGCCGGGTGTCCATACGCATCCTTGACGAGCTGGTGCTGCCCTTCCAGG
AGCTGCAGATCGATGACAATGAGTATGCCTACCTCAAAGCCATCATCTTCTTTGACCCAGATGCCAAGGG
GCTGAGCGATCCAGGGAAGATCAAGCGGCTGCGTTCCCAGGTGCAGGTGAGCTTGGAGGACTACATCAAC
GACCGCCAGTATGACTCGCGTGGCCGCTTTGGAGAGCTGCTGCTGCTGCTGCCCACCTTGCAGAGCATCA
CCTGGCAGATGATCGAGCAGATCCAGTTCATCAAGCTCTTCGGCATGGCCAAGATTGACAACCTGTTGCA
GGAGATGCTGCTGGGAGGGTCCCCCAGCGATGCACCCCATGCCCACCACCCCTGCACCCTCACCTGATG
CAGGAACATATGGGAACCAACGTCATCGTTGCCAACACAATGCCCACTCACCTCAGCAACGGACAGATGT
CCACCCCTGAGACCCCACAGCCCTCACCGCCAGGTGGCTCAGGGTCTGAGCCCTATAAGCTCCTGCCGGG
AGCCGTCGCCACAATCGTCAAGCCCCTCTCTGCCATCCCCCAGCCGACCATCACCAAGCAGGAAGTTATC
TAGCAAGCCGCTGGGGCTTGGGGGCTCCACTGGCTCCCCCAGCCCCTAAGAGAGCACCTGGTGATCAC
GTGGTCACGGCAAAGGAAGACGTGATGCCAGGACCAGTCCCAGAGCAGGAATGGGAAGGATGAAGGGCCC
GAGAACATGGCCTAAGGGCCACATCCCACTGCCACCCTTGACGCCCTGCTCTGGATAACAAGACTTTGAC
TTGGGGAGACCTCTACTGCCTTGGACAACTTTTCTCATGTTGAAGCCACTGCCTTCACCTTCACCTTCAT
CCATGTCCAACCCCCGACTTCATCCCAAAGGACAGCCGCCTGGAGATGACTTGAGGCCTTACTTAAACCC
AGCTCCCTTCTTCCCTAGCCTGGTGCTTCTCCTCTCCTAGCCCCTGTCATGGTGTCCAGACAGAGCCCTG
TGAGGCTGGGTCCAATTGTGGCACTTGGGGCACCTTGCTCCTCCTTCTGCTGCTGCCCCACCTCTGCTG
CCTCCCTCTGCTGTCACCTTGCTCAGCCATCCCGTCTTCTCCAACACCACCTCTCCAGAGGCCAAGGAGG
CCTTGGAAACGATTCCCCCAGTCATTCTGGGAACATGTTGTAAGCACTGACTGGGACCAGGCACCAGGCA
GGGTCTAGAAGGCTGTGGTGAGGGAAGACGCCTTTCTCCTCCAACCCAACCTCATCCTCCTTCTTCAGGG
ACTTGGGTGGGTACTTGGGTGAGGATCCCTGAAGGCCTTCAACCCGAGAAAACAAACCCAGGTTGGCGAC
TGCAACAGGAACTTGGAGTGGAGAGGAAAAGCATCAGAAAGAGGCAGACCATCCACCAGGCCTTTGAGAA
AGGGTAGAATTCTGGCTGGTAGAGCAGGTGAGATGGGACATTCCAAAGAACAGCCTGAGCCAAGGCCTAG
TGGTAGTAAGAATCTAGCAAGAATTGAGGAAGAATGGTGTGGGAGAGGGATGATGAAGAGAGAGAGGGCC
TGCTGGAGAGCATAGGGTCTGGAACACCAGGCTGAGGTCCTGATCAGCTTCAAGGAGTATGCAGGGAGCT
GGGCTTCCAGAAAATGAACACAGCAGTTCTGCAGAGGACGGGAGGCTGGAAGCTGGGAGGTCAGGTGGGG
TGGATGATATAATGCGGGTGAGAGTAATGAGGCTTGGGGCTGGAGAGGACAAGATGGGTAAACCCTCACA
TCAGAGTGACATCCAGGAGGAATAAGCTCCCAGGGCCTGTCTCAAGCTCTTCCTTACTCCCAGGCACTGT
CTTAAGGCATCTGACATGCATCATCTCATTTAATCCTCCCTTCCTCCCTATTAACCTAGAGATTGTTTTT
GTTTTTTATTCTCCTCCTCCCTCCCCGCCCTCACCCGCCCCACTCCCTCCTAACCTAGAGATTGTTACAG
AAGCTGAAATTGCGTTCTAAGAGGTGAAGTGATTTTTTTCTGAAACTCACACAACTAGGAAGTGGCTGA
GTCAGGACTTGAACCCAGGTCTCCCTGGATCAGAACAGGAGCTCTTAACTACAGTGGCTGAATAGCTTCT
CCAAAGGCTCCCTGTGTTCTCACCGTGATCAAGTTGAGGGGCTTCCGGCTCCCTTCTACAGCCTCAGAAA
CCAGACTCGTTCTTCTGGGAACCCTGCCCACTCCCAGGACCAAGATTGGCCTGAGGCTGCACTAAAATTC
ACTTAGGGTCGAGCATCCTGTTTGCTGATAAATATTAAGGAGAATTCATGACTCTTGACAGCTTTTCTCT
CTTCACTCCCAAGTCAAGGGGAGGGGTGGCAGGGGTCTGTTTCCTGGAAGTCAGGCTCATCTGGCCTGT
TGGCATGGGGTGGGACAGTGTGCACAGTGTGGGGCAGGGGAGGGCTAAGCAGGCCTGGGTTTGAGGGC
TGCTCCGGAGACCGTCACTCCAGGTGCATTCTGGAAGCATTAGACCCCAGGATGGAGCGACCAGCATGTC
ATCCATGTGGAATCTTGGTGGCTTTGAGGACATTCTGGAAAATGCCACTGACCAGTGTGAACAAAGGGA
TGTGTTATGGGGCTGGAGGTGTGATTAGGTAGGAGGGAAACTGTTGGACCGACTCCTGCCCCCTGCTCAA
CACTGACCCCTCTGAGTGGTTGGAGGCAGTGCCCCAGTGCCCAGAAATCCCACCATTAGTGATTGTTTTT
TATGAGAAAGAGGCGTGGAGAAGTATTGGGGCAATGTGTCAGGGAGGAATCACCACATCCCTACGGCAGT
```

FIG. 5A

```
CCCAGCCAAGCCCCCAATCCCAGCGGAGACTGTGCCCTGCTCAGAGCTCCCAAGCCTTCCCCCACCACCT
CACTCAAGTGCCCCTGAAATCCCTGCCAGACGGCTCAGCCTGGTCTGCGGTAAGGCAGGGAGGCTGGAAC
CATTTCTGGGCATTGTGGTCATTCCCACTGTGTTCCTCCACCTCCTCCCTCCAGCGTTGCTCAGACCTCT
GTCTTGGGAGAAAGGTTGAGATAAGAATGTCCCATGGAGTGCCGTGGGCAACAGTGGCCCTTCATGGGAA
CAATCTGTTGGAGCAGGGGGTCAGTTCTCTGCTGGGAATCTACCCCTTTCTGGAGGAGAAACCCATTCCA
CCTTAATAACTTTATTGTAATGTGAGAAACACAAAACAAAGTTTACTTTTTTGACTCTAAGCTGACATGA
TATTAGAAAATCTCTCGCTCTCTTTTTTTTTTTTTTTTTTTTGGCTACTTGAGTTGTGGTCCTAAA
ACATAAAATCTGATGGACAAACAGAGGGTTGCTGGGGGGACAAGCGTGGGCACAATTTCCCCACCAAGAC
ACCCTGATCTTCAGGCGGGTCTCAGGAGCTTCTAAAAATCCGCATGGCTCTCCTGAGAGTGGACAGAGGA
GAGGAGAGGGTCAGAAATGAACGCTCTTCTATTTCTTGTCATTACCAAGCCAATTACTTTTGCCAAATTT
TTCTGTGATCTGCCCTGATTAAGATGAATTGTGAAATTTACATCAAGCAATTATCAAAGCGGGCTGGGTC
CCATCAGAACGACCCACATCTTTCTGTGGGTGTGAATGTCATTAGGTCTTGCGCTGACCCCTGAGCCCCC
ATCACTGCCGCCTGATGGGGCAAAGAAACAAAAAACATTTCTTACTCTTCTGTGTTTAACAAAAGTTTA
TAAAACAAAATAAATGGCGCATATGTTTCTAAAAAAAAAAAAAAAAAA
```

FIG. 5B

>NM_001030004.2 Homo sapiens hepatocyte nuclear factor 4 alpha (HNF4A),
transcript variant 6, mRNA (SEQ ID NO: 3)

```
GGCCATGGTCAGCGTGAACGCGCCCCTCGGGGCTCCAGTGGAGAGTTCTTACGACACGTCCCCATCAGAA
GGCACCAACCTCAACGCGCCCAACAGCCTGGGTGTCAGCGCCCTGTGTGCCATCTGCGGGGACCGGGCCA
CGGGCAAACACTACGGTGCCTCGAGCTGTGACGGCTGCAAGGGCTTCTTCCGGAGGAGCGTGCGGAAGAA
CCACATGTACTCCTGCAGATTTAGCCGGCAGTGCGTGGTGGACAAAGACAAGAGGAACCAGTGCCGCTAC
TGCAGGCTCAAGAAATGCTTCCGGGCTGGCATGAAGAAGGAAGCCGTCCAGAATGAGCGGGACCGGATCA
GCACTCGAAGGTCAAGCTATGAGGACAGCAGCCTGCCCTCCATCAATGCGCTCCTGCAGGCGGAGGTCCT
GTCCCGACAGATCACCTCCCCCGTCTCCGGGATCAACGGCGACATTCGGGCGAAGAAGATTGCCAGCATC
GCAGATGTGTGTGAGTCCATGAAGGAGCAGCTGCTGGTTCTCGTTGAGTGGGCCAAGTACATCCCAGCTT
TCTGCGAGCTCCCCCTGGACGACCAGGTGGCCCTGCTCAGAGCCCATGCTGGCGAGCACCTGCTGCTCGG
AGCCACCAAGAGATCCATGGTGTTCAAGGACGTGCTGCTCCTAGGCAATGACTACATTGTCCCTCGGCAC
TGCCCGGAGCTGGCGGAGATGAGCCGGGTGTCCATACGCATCCTTGACGAGCTGGTGCTGCCCTTCCAGG
AGCTGCAGATCGATGACAATGAGTATGCCTACCTCAAAGCCATCATCTTCTTTGACCCAGATGCCAAGGG
GCTGAGCGATCCAGGGAAGATCAAGCGGCTGCGTTCCCAGGTGCAGGTGAGCTTGGAGGACTACATCAAC
GACCGCCAGTATGACTCGCGTGGCCGCTTTGGAGAGCTGCTGCTGCTGCTGCCCACCTTGCAGAGCATCA
CCTGGCAGATGATCGAGCAGATCCAGTTCATCAAGCTCTTCGGCATGGCCAAGATTGACAACCTGTTGCA
GGAGATGCTGCTGGGAGGTCCGTGCCAAGCCCAGGAGGGGCGGGGTTGGAGTGGGGACTCCCCAGGAGAC
AGGCCTCACACAGTGAGCTCACCCCTCAGCTCCTTGGCTTCCCCACTGTGCCGCTTTGGGCAAGTTGCTT
AACCTGTCTGTGCCTCAGTTTCCTCACCAGAAAAATGGGAACAAGGCAATGGTCTATTTGTTCAGGCACC
GAGAACCTAGCACGTGCCAGTCACTGTTCTAAGTGCTGGCAATTCAGCAAAGAACAAGATCTTTGCCCTC
GGGGAGGCTGTGTGTGTGTGAGTATGTATGGATGCGTGGATATCTGTGTATATGCCCGTATGTGCGTGCA
TGTGTATATAAAGCCTCACATTTTATGATTTTGAAATAAACAGGTAATA
```

FIG. 6

MODIFIED siRNA

| siRNA sense (SEQ ID NO:) | siRNA antisense (SEQ ID NO:) |
| --- | --- |
| gsasggacCfuGfAfAfgaaggugauaL96 (4) | usAfsucaCfcUfUfcuucAfgGfuccucscsu (5) |
| gscstccaGfTfGfGfAfgagttcttL96 (6) | asAfsgaaCfuCfUfccacUfgGfagcscsc (7) |
| gscstccaGfTfGfGfAfgagttcttaL96 (8) | usAfsagaAfcUfCfuccaCfuGfgagcscsc (9) |
| gscstccaGfTfGfGfAfgagttcttacL96 (10) | gsUfsaagAfaCfUfcuccAfcUfggagcscsc (11) |
| cstsccagTfgGfAfGfagttcttaL96 (12) | usAfsagaAfcUfCfuccaCfuGfgagscsc (13) |
| cstsccagTfgGfAfGfagttcttacL96 (14) | gsUfsaagAfaCfUfcuccAfcUfggagscsc (15) |
| cstsccagTfgGfAfGfagttcttacgL96 (16) | csGfsuaaGfaAfCfucucCfaCfuggagscsc (17) |
| tscscagtGfgAfGfAfgttcttacL96 (18) | gsUfsaagAfaCfUfcuccAfcUfggasgsc (19) |
| tscscagtGfgAfGfAfgttcttacgL96 (20) | csGfsuaaGfaAfCfucucCfaCfuggasgsc (21) |
| tscscagtGfgAfGfAfgttcttacgtL96 (22) | usCfsguaAfgAfAfcucuCfcAfcuggasgsc (23) |
| gsgsagagTftCfTfTfacgacacgL96 (24) | csGfsuguCfgUfAfagaaCfuCfuccsasc (25) |
| gsgsagagTftCfTfTfacgacacgtL96 (26) | asCfsgugUfcGfUfaagaAfcUfcuccsasc (27) |
| gsgsagagTftCfTfTfacgacacgtcL96 (28) | gsAfscguGfuCfGfuaagAfaCfucuccsasc (29) |

NAKED siRNA

| siRNA sense (SEQ ID NO:) | siRNA antisense (SEQ ID NO:) |
| --- | --- |
| GCTCCAGTGGAGAGTTCTTdTdT (30) | CGTGTCGTAAGAACTCTCCdTdT (31) |
| CTCCAGTGGAGAGTTCTTAdTdT (32) | GTAAGAACTCTCCACTGGAdTdT (33) |
| TCCAGTGGAGAGTTCTTACdTdT (34) | TAAGAACTCTCCACTGGAGdTdT (35) |
| GGAGAGTTCTTACGACACGdTdT (36) | AAGAACTCTCCACTGGAGCdTdT (37) |

FIG. 7A

| Abbreviation | Nucleotide monomer |
| --- | --- |
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |
| dT | 2'-deoxythymidine-3'-phosphate |

FIG. 7B

SEQUENCE LISTING

```
<160> NUMBER OF SEQ ID NOS: 44

<210> SEQ ID NO 1
<211> LENGTH: 4558
<212> TYPE: DNA
<213> ORGANISM: Homo sapiens

<400> SEQUENCE: 1
ggccatggtc agcgtgaacg cgcccctcgg ggctccagtg gagagttctt acgacacgtc      60
cccatcagaa ggcaccaacc tcaacgcgcc caacagcctg ggtgtcagcg ccctgtgtgc     120
catctgcggg gaccgggcca cgggcaaaca ctacggtgcc tcgagctgtg acggctgcaa     180
gggcttcttc cggaggagcg tgcggaagaa ccacatgtac tcctgcagat ttagccggca     240
gtgcgtggtg gacaaagaca agaggaacca gtgccgctac tgcaggctca agaaatgctt     300
ccgggctggc atgaagaagg aagccgtcca gaatgagcgg gaccggatca gcactcgaag     360
gtcaagctat gaggacagca gcctgccctc catcaatgcg ctcctgcagg cggaggtcct     420
gtcccgacag atcacctccc ccgtctccgg gatcaacggc gacattcggg cgaagaagat     480
tgccagcatc gcagatgtgt gtgagtccat gaaggagcag ctgctggttc tcgttgagtg     540
ggccaagtac atcccagctt tctgcgagct cccctggac gaccaggtgg ccctgctcag     600
agcccatgct ggcgagcacc tgctgctcgg agccaccaag agatccatgg tgttcaagga     660
cgtgctgctc ctaggcaatg actacattgt ccctcggcac tgcccggagc tggcggagat     720
```

```
gagccgggtg tccatacgca tccttgacga gctggtgctg cccttccagg agctgcagat    780
cgatgacaat gagtatgcct acctcaaagc catcatcttc tttgacccag atgccaaggg    840
gctgagcgat ccagggaaga tcaagcggct gcgttcccag gtgcaggtga gcttggagga    900
ctacatcaac gaccgccagt atgactcgcg tggccgcttt ggagagctgc tgctgctgct    960
gcccaccttg cagagcatca cctggcagat gatcgagcag atccagttca tcaagctctt   1020
cggcatggcc aagattgaca acctgttgca ggagatgctg ctgggagggt ccccagcga   1080 tgcaccccat gcccaccacc cctgcaccc tcacctgatg caggaacata tgggaaccaa    1140
cgtcatcgtt gccaacacaa tgcccactca cctcagcaac ggacagatgt gtgagtggcc    1200
ccgacccagg ggacaggcag ccaccccctga ccccacag ccctcaccgc caggtggctc    1260
agggtctgag ccctataagc tcctgccggg agccgtcgcc acaatcgtca agccctctc     1320 tgccatcccc cagccgacca tcaccaagca ggaagttatc tagcaagccg ctggggcttg    1380
ggggctccac tggctccccc cagccccta agagagcacc tggtgatcac gtggtcacgg    1440
caaaggaaga cgtgatgcca ggaccagtcc cagagcagga atgggaagga tgaagggccc    1500
gagaacatgg cctaagggcc catcccact gccacccttg acgccctgct ctggataaca    1560
agactttgac ttggggagac ctctactgcc ttggacaact tttctcatgt tgaagccact    1620
gccttcacct tcaccttcat ccatgtccaa ccccgactt catcccaaag acagccgcc    1680 tggagatgac ttgaggcctt acttaaaccc agctcccttc ttccctagcc tggtgcttct    1740
cctctcctag cccctgtcat ggtgtccaga cagagccctg tgaggctggg tccaattgtg    1800
gcacttgggg caccttgctc ctccttctgc tgctgccccc acctctgctg cctccctctg    1860
ctgtcacctt gctcagccat cccgtcttct ccaacaccac ctctccagag gccaaggagg    1920
ccttggaaac gattcccca gtcattctgg gaacatgttg taagcactga ctgggaccag    1980
gcaccaggca gggtctagaa ggctgtggtg agggaagacg cctttctcct ccaacccaac    2040
ctcatcctcc ttcttcaggg acttgggtgg gtacttgggt gaggatccct gaaggccttc    2100
aacccgagaa aacaaaccca ggttggcgac tgcaacagga acttggagtg gagaggaaaa    2160
gcatcagaaa gaggcagacc atccaccagg cctttgagaa agggtagaat tctggctggt    2220
agagcaggtg agatgggaca ttccaaagaa cagcctgagc caaggcctag tggtagtaag    2280
aatctagcaa gaattgagga agaatggtgt gggagaggga tgatgaagag agagagggcc    2340
tgctggagag catagggtct ggaacaccag gctgaggtcc tgatcagctt caaggagtat    2400
gcagggagct gggcttccag aaaatgaaca cagcagttct gcagaggacg ggaggctgga    2460
agctgggagg tcaggtgggg tggatgatat aatgcgggtg agagtaatga ggcttggggc    2520
tggagaggac aagatgggta aaccctcaca tcagagtgac atccaggagg aataagctcc    2580
cagggcctgt ctcaagctct tccttactcc caggcactgt cttaaggcat ctgacatgca    2640
tcatctcatt taatcctccc ttcctcccta ttaacctaga gattgttttt gttttttatt    2700
ctcctcctcc ctccccgccc tcacccgccc cactccctcc taacctagag attgttacag    2760
aagctgaaat tgcgttctaa gaggtgaagt gatttttttt ctgaaactca cacaactagg    2820
aagtggctga gtcaggactt gaaccccaggt ctccctggat cagaacagga gctcttaact    2880
acagtggctg aatagcttct ccaaaggctc cctgtgttct caccgtgatc aagttgaggg    2940
gcttccggct cccttctaca gcctcagaaa ccagactcgt tcttctggga accctgccca    3000
ctcccaggac caagattggc ctgaggctgc actaaaattc acttagggtc gagcatcctg    3060
```

```
tttgctgata aatattaagg agaattcatg actcttgaca gcttttctct cttcactccc     3120
caagtcaagg ggaggggtgg caggggtctg tttcctggaa gtcaggctca tctggcctgt     3180
tggcatgggg gtgggacagt gtgcacagtg tgggggcagg ggagggctaa gcaggcctgg     3240
gtttgagggc tgctccggag accgtcactc caggtgcatt ctggaagcat tagaccccag     3300
gatggagcga ccagcatgtc atccatgtgg aatcttggtg gctttgagga cattctggaa     3360
aatgccactg accagtgtga acaaaaggga tgtgttatgg ggctggaggt gtgattaggt     3420
aggagggaaa ctgttggacc gactcctgcc ccctgctcaa cactgacccc tctgagtggt     3480
tggaggcagt gccccagtgc ccagaaatcc accattagt  gattgttttt tatgagaaag     3540
aggcgtggag aagtattggg gcaatgtgtc agggaggaat caccacatcc ctacggcagt     3600
cccagccaag cccccaatcc cagcggagac tgtgccctgc tcagagctcc caagccttcc     3660
cccaccacct cactcaagtg cccctgaaat ccctgccaga cggctcagcc tggtctgcgg     3720
taaggcaggg aggctggaac catttctggg cattgtggtc attcccactg tgttcctcca     3780
cctcctccct ccagcgttgc tcagacctct gtcttggaga aaaggttgag ataagaatgt     3840
cccatggagt gccgtgggca acagtggccc ttcatgggaa caatctgttg gagcagggg     3900 tcagttctct gctgggaatc taccccttc tggaggagaa acccattcca ccttaataac      3960
tttattgtaa tgtgagaaac acaaaacaaa gtttactttt ttgactctaa gctgacatga     4020
tattagaaaa tctctcgctc tcttttttttt tttttttttt tttttttggct acttgagttg   4080 tggtcctaaa acataaaatc tgatggacaa acagagggtt gctgggggga caagcgtggg     4140
cacaatttcc ccaccaagac accctgatct tcaggcgggt tcaggagct tctaaaaatc      4200 cgcatggctc tcctgagagt ggacagagga gaggagaggg tcagaaatga acgctcttct     4260
atttcttgtc attaccaagc caattacttt tgccaaattt ttctgtgatc tgccctgatt     4320
aagatgaatt gtgaaatttta catcaagcaa ttatcaaagc gggctgggtc ccatcagaac    4380
gacccacatc tttctgtggg tgtgaatgtc attaggtctt cgctgacccc ctgagccccc    4440
atcactgccg cctgatgggg caaagaaaca aaaaacattt cttactcttc tgtgttttaa    4500
caaaagttta taaacaaaa taatggcgc atatgttttc taaaaaaaaa aaaaaaa        4558
```

<210> SEQ ID NO 2
<211> LENGTH: 4528
<212> TYPE: DNA
<213> ORGANISM: Homo sapiens

<400> SEQUENCE: 2

```
ggccatggtc agcgtgaacg cgcccctcgg ggctccagtg gagagttctt acgacacgtc      60
cccatcagaa ggcaccaacc tcaacgcgcc aacagcctg ggtgtcagcg ccctgtgtgc     120
catctgcggg gaccgggcca cgggcaaaca ctacggtgcc tcgagctgtg acggctgcaa    180
gggcttcttc cggaggagcg tgcggaagaa ccacatgtac tcctgcagat ttagccggca    240
gtgcgtggtg gacaaagaca agaggaacca gtgccgctac tgcaggctca gaaatgcttt    300
ccgggctggc atgaagaagg aagccgtcca gaatgagcgg gaccggatca gcactcgaag    360
gtcaagctat gaggacagca gcctgccctc catcaatgcg ctcctgcagg cggaggtcct    420
gtcccgacag atcacctccc ccgtctccgg gatcaacggc gacattcggg cgaagaagat    480
tgccagcatc gcagatgtgt gtgagtccat gaaggagcag ctgctggttc tcgttgagtg    540
ggccaagtac atcccagctt tctgcgagct ccccctggac gaccaggtgg ccctgctcag    600
agcccatgct ggcgagcacc tgctgctcgg agccaccaag agatccatgg tgttcaagga    660
```

-continued

```
cgtgctgctc ctaggcaatg actacattgt ccctcggcac tgcccggagc tggcggagat    720
gagccgggtg tccatacgca tccttgacga gctggtgctg cccttccagg agctgcagat    780
cgatgacaat gagtatgcct acctcaaagc catcatcttc tttgacccag atgccaaggg    840
gctgagcgat ccaggaaga tcaagcggct gcgttccag gtgcaggtga gcttggagga    900
ctacatcaac gaccgccagt atgactcgcg tggccgcttt ggagagctgc tgctgctgct    960
gcccaccttg cagagcatca cctggcagat gatcgagcag atccagttca tcaagctctt   1020
cggcatggcc aagattgaca acctgttgca ggagatgctg ctgggagggt ccccagcga    1080
tgcaccccat gccaccacc ccctgcaccc tcacctgatg caggaacata tgggaaccaa   1140
cgtcatcgtt gccaacacaa tgcccactca cctcagcaac ggacagatgt ccacccctga   1200
gaccccacag ccctcaccgc caggtggctc agggtctgag ccctataagc tcctgccggg   1260
agccgtcgcc acaatcgtca agcccctctc tgccatcccc cagccgacca tcaccaagca   1320
ggaagttatc tagcaagccg ctggggcttg ggggctccac tggctccccc agcccccta   1380
agagagcacc tggtgatcac gtggtcacgg caaaggaaga cgtgatgcca ggaccagtcc   1440
cagagcagga tgggaagga tgaagggccc gagaacatgg cctaagggcc acatcccact   1500
gccacccttg acgccctgct ctggataaca agactttgac ttggggagac ctctactgcc   1560
ttggacaact tttctcatgt tgaagccact gccttcacct tccacttcat ccatgtccaa   1620
cccccgactt catcccaaag gacagccgcc tggagatgac ttgaggcctt acttaaaccc   1680
agctcccttc ttccctagcc tggtgcttct cctctcctag ccctgtcat ggtgtccaga   1740
cagagccctg tgaggctggg tccaattgtg gcacttgggg caccttgctc ctccttctgc   1800
tgctgccccc acctctgctg cctccctctg ctgtcacctt gctcagccat cccgtcttct   1860
ccaacaccac ctctccagag gccaaggagg ccttggaaac gattccccca gtcattctgg   1920
gaacatgttg taagcactga ctgggaccag gcaccaggca gggtctagaa ggctgtggtg   1980
agggaagacg cctttctcct ccaacccaac ctcatcctcc ttcttcaggg acttgggtgg   2040
gtacttgggt gaggatccct gaaggccttc aacccgagaa aacaaaccca ggttggcgac   2100
tgcaacagga acttggagtg gagaggaaaa gcatcagaaa gaggcagacc atccaccagg   2160
cctttgagaa agggtagaat tctggctggt agagcaggtg agatgggaca ttccaaagaa   2220
cagcctgagc caaggcctag tggtagtaag aatctagcaa gaattgagga agaatggtgt   2280
gggagaggga tgatgaagag agagagggcc tgctggagag catagggtct ggaacaccag   2340
gctgaggtcc tgatcagctt caaggagtat gcagggagct gggcttccag aaaatgaaca   2400
cagcagttct gcagaggacg ggaggctgga agctgggagg tcaggtgggg tggatgatat   2460
aatgcgggtg agagtaatga ggcttgggc tggagaggac aagatgggta aaccctcaca   2520
tcagagtgac atccaggagg aataagctcc cagggcctgt ctcaagctct tccttactcc   2580
caggcactgt cttaaggcat ctgacatgca tcatctcatt taatcctccc ttcctcccta   2640
ttaacctaga gattgttttt gttttttatt ctcctcctcc ctccccgccc tcacccgccc   2700
cactccctcc taacctagag attgttacag aagctgaaat tgcgttctaa gaggtgaagt   2760
gatttttttt ctgaaactca cacaactagg aagtggctga gtcaggactt gaacccaggt   2820
ctccctggat cagaacagga gctcttaact acagtggctg aatagcttct ccaaaggctc   2880
cctgtgttct caccgtgatc aagttgaggg gcttccggct cccttctaca gcctcagaaa   2940
ccagactcgt tcttctggga accctgccca ctcccaggac caagattggc ctgaggctgc   3000
```

```
actaaaattc acttagggtc gagcatcctg tttgctgata aatattaagg agaattcatg    3060
actcttgaca gctttctct cttcactccc caagtcaagg ggaggggtgg caggggtctg    3120
tttcctggaa gtcaggctca tctggcctgt tggcatgggg gtgggacagt gtgcacagtg    3180
tgggggcagg ggagggctaa gcaggcctgg gtttgagggc tgctccggag accgtcactc    3240
caggtgcatt ctggaagcat tagaccccag gatggagcga ccagcatgtc atccatgtgg    3300
aatcttggtg gctttgagga cattctggaa aatgccactg accagtgtga acaaaaggga    3360
tgtgttatgg ggctggaggt gtgattaggt aggagggaaa ctgttggacc gactcctgcc    3420
ccctgctcaa cactgacccc tctgagtggt tggaggcagt gccccagtgc ccagaaatcc    3480
caccattagt gattgttttt tatgagaaag aggcgtggag aagtattggg gcaatgtgtc    3540
agggaggaat caccacatcc ctacggcagt cccagccaag cccccaatcc cagcggagac    3600
tgtgccctgc tcagagctcc caagccttcc cccaccacct cactcaagtg cccctgaaat    3660
ccctgccaga cggctcagcc tggtctgcgg taaggcaggg aggctggaac catttctggg    3720
cattgtggtc attcccactg tgttcctcca cctcctccct ccagcgttgc tcagacctct    3780
gtcttgggag aaaggttgag ataagaatgt cccatggagt gccgtgggca acagtggccc    3840
ttcatgggaa caatctgttg gagcagggggg tcagttctct gctgggaatc tacccctttc    3900
tggaggagaa acccattcca ccttaataac tttattgtaa tgtgagaaac acaaaacaaa    3960
gtttactttt ttgactctaa gctgacatga tattagaaaa tctctcgctc tcttttttt    4020
tttttttt ttttttggct acttgagttg tggtcctaaa acataaaatc tgatggacaa    4080
acagagggtt gctggggga caagcgtggg cacaatttcc ccaccaagac accctgatct    4140
tcaggcgggt ctcaggagct tctaaaaatc cgcatggctc tcctgagagt ggacagagga    4200
gaggagaggg tcagaaatga acgctcttct atttcttgtc attaccaagc caattacttt    4260
tgccaaattt ttctgtgatc tgccctgatt aagatgaatt gtgaaattta catcaagcaa    4320
ttatcaaagc gggctgggtc ccatcagaac gaccccacatc tttctgtggg tgtgaatgtc    4380
attaggtctt gcgctgaccc ctgagccccc atcactgccg cctgatgggg caaagaaaca    4440
aaaaacattt cttactcttc tgtgttttaa caaaagttta taaacaaaa taaatggcgc    4500
atatgttttc taaaaaaaaa aaaaaaa                                        4528

<210> SEQ ID NO 3
<211> LENGTH: 1449
<212> TYPE: DNA
<213> ORGANISM: Homo sapiens

<400> SEQUENCE: 3
ggccatggtc agcgtgaacg cgcccctcgg ggctccagtg gagagttctt acgacacgtc     60
cccatcagaa ggcaccaacc tcaacgcgcc caacagcctg ggtgtcagcg ccctgtgtgc    120
catctgcggg gaccgggcca cgggcaaaca ctacggtgcc tcgagctgtg acggctgcaa    180
gggcttcttc cggaggagcg tgcggaagaa ccacatgtac tcctgcagat ttagccggca    240
gtgcgtggtg gacaaagaca agaggaacca gtgccgctac tgcaggctca agaaatgctt    300
ccggggctggc atgaagaagg aagccgtcca gaatgagcgg gaccggatca gcactcgaag    360
gtcaagctat gaggacagca gcctgccctc catcaatgcg ctcctgcagg cggaggtcct    420
gtcccgacag atcacctccc ccgtctccgg gatcaacggc gacattcggg cgaagaagat    480
tgccagcatc gcagatgtgt gtgagtccat gaaggagcag ctgctggttc tcgttgagtg    540
ggccaagtac atcccagctt tctgcgagct cccccctggac gaccaggtgg ccctgctcag    600
```

```
agcccatgct ggcgagcacc tgctgctcgg agccaccaag agatccatgg tgttcaagga    660
cgtgctgctc ctaggcaatg actacattgt ccctcggcac tgcccggagc tggcggagat    720
gagccgggtg tccatacgca tccttgacga gctggtgctg cccttccagg agctgcagat    780
cgatgacaat gagtatgcct acctcaaagc catcatcttc tttgacccag atgccaaggg    840
gctgagcgat ccagggaaga tcaagcggct gcgttcccag gtgcaggtga gcttggagga    900
ctacatcaac gaccgccagt atgactcgcg tggccgcttt ggagagctgc tgctgctgct    960
gcccaccttg cagagcatca cctggcagat gatcgagcag atccagttca tcaagctctt   1020
cggcatggcc aagattgaca acctgttgca ggagatgctc tgggaggtc cgtgccaagc    1080 ccaggagggg cggggttgga gtggggactc cccaggagac aggcctcaca cagtgagctc   1140 accccctcagc tccttggctt ccccactgtg ccgctttggg caagttgctt aacctgtctg   1200
tgcctcagtt tcctcaccag aaaaatggga acaaggcaat ggtctatttg ttcaggcacc   1260
gagaacctag cacgtgccag tcactgttct aagtgctggc aattcagcaa agaacaagat   1320
ctttgccctc ggggaggctg tgtgtgtgtg agtatgtatg gatgcgtgga tatctgtgta   1380
tatgcccgta tgtgcgtgca tgtgtatata aagcctcaca ttttatgatt ttgaaataaa   1440
caggtaata                                                           1449

<210> SEQ ID NO 4
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylguanosine-3'-phosphorothioate
<220> FEATURE:
<221> NAME/KEY: modified_base
<222> LOCATION: (2)..(2)
<223> OTHER INFORMATION: 2'-O-methyladenosine-3'-phosphorothioate
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluoroguanosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
```

```
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyladenosine-3'-phosphate
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: N-[tris(GalNAc-alkyl)-amidodecanoyl]-4-
    hydroxyprolinol
<220> FEATURE:
<221> NAME/KEY: modified_base
<222> LOCATION: (21)..(21)
<223> OTHER INFORMATION: 2'-O-methyladenosine-3'-phosphate

<400> SEQUENCE: 4
gaggaccuga agaaggugau a                                              21

<210> SEQ ID NO 5
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
```

```
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluorocytidine-3'-phosphate
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(9)
<223> OTHER INFORMATION: 2'-fluorouridine-3'-phosphate
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoroguanosine-3'-phosphate
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(19)
<223> OTHER INFORMATION: cm
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(22)
<223> OTHER INFORMATION: 2'-O-methylcytidine-3'-phosphorothioate
<220> FEATURE:
<221> NAME/KEY: modified_base
<222> LOCATION: (23)..(23)
<223> OTHER INFORMATION: um

<400> SEQUENCE: 5
uaucaccuuc uucagguccu ccu                                              23

<210> SEQ ID NO 6
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylguanosine-3'-phosphorothioate
<220> FEATURE:
<221> NAME/KEY: modified_base
<222> LOCATION: (2)..(2)
<223> OTHER INFORMATION: 2'-O-methylcytidine-3'-phosphorothioate
<220> FEATURE:
<221> NAME/KEY: modified_base
```

<222> LOCATION: (3)..(3)
<223> OTHER INFORMATION: tm
<220> FEATURE:
<221> NAME/KEY: modified_base
<222> LOCATION: (4)..(5)
<223> OTHER INFORMATION: cm
<220> FEATURE:
<221> NAME/KEY: modified_base
<222> LOCATION: (6)..(6)
<223> OTHER INFORMATION: 2'-O-methyladenosine-3'-phosphate
<220> FEATURE:
<221> NAME/KEY: modified_base
<222> LOCATION: (7)..(7)
<223> OTHER INFORMATION: 2'-fluoroguanosine-3'-phosphate
<220> FEATURE:
<221> NAME/KEY: modified_base
<222> LOCATION: (8)..(8)
<223> OTHER INFORMATION: tm
<220> FEATURE:
<221> NAME/KEY: modified_base
<222> LOCATION: (9)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(16)
<223> OTHER INFORMATION: tm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: tm
<220> FEATURE:
<221> NAME/KEY: modified_base
<222> LOCATION: (19)..(19)
<223> OTHER INFORMATION: N-[tris(GalNAc-alkyl)-amidodecanoyl]-4-
     hydroxyprolinol Hyp-(GalNAc-alkyl)3
<220> FEATURE:
<221> NAME/KEY: modified_base
<222> LOCATION: (19)..(19)
<223> OTHER INFORMATION: tm

<400> SEQUENCE: 6
gcuccagugg agaguucuu                                              19

<210> SEQ ID NO 7
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methyladenosine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate

```
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluorocytidine-3'-phosphate
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-fluorouridine-3'-phosphate
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: 2'-O-methyladenosine-3'-phosphate
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoroguanosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(20)
<223> OTHER INFORMATION: 2'-O-methylcytidine-3'-phosphorothioate
<220> FEATURE:
<221> NAME/KEY: modified_base
<222> LOCATION: (21)..(21)
<223> OTHER INFORMATION: cm

<400> SEQUENCE: 7
aagaacucuc cacuggagcc c                                              21

<210> SEQ ID NO 8
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
```

```
<223> OTHER INFORMATION: 2'-O-methylguanosine-3'-phosphorothioate
<220> FEATURE:
<221> NAME/KEY: modified_base
<222> LOCATION: (2)..(2)
<223> OTHER INFORMATION: 2'-O-methylcytidine-3'-phosphorothioate
<220> FEATURE:
<221> NAME/KEY: modified_base
<222> LOCATION: (3)..(3)
<223> OTHER INFORMATION: tm
<220> FEATURE:
<221> NAME/KEY: modified_base
<222> LOCATION: (4)..(5)
<223> OTHER INFORMATION: cm
<220> FEATURE:
<221> NAME/KEY: modified_base
<222> LOCATION: (6)..(6)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: tm
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(16)
<223> OTHER INFORMATION: tm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(19)
<223> OTHER INFORMATION: tm
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: N-[tris(GalNAc-alkyl)-amidodecanoyl]-4-
      hydroxyprolinol Hyp-(GalNAc-alkyl)3

<400> SEQUENCE: 8
gcuccagugg agaguucuua                                                   20

<210> SEQ ID NO 9
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: gm
<220> FEATURE:
```

```
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluorouridine-3'-phosphate
<220> FEATURE:
<221> NAME/KEY: modified_base
<222> LOCATION: (9)..(9)
<223> OTHER INFORMATION: 2'-fluorocytidine-3'-phosphate
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoroguanosine-3'-phosphate
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(21)
<223> OTHER INFORMATION: 2'-O-methylcytidine-3'-phosphorothioate
<220> FEATURE:
<221> NAME/KEY: modified_base
<222> LOCATION: (22)..(22)
<223> OTHER INFORMATION: cm

<400> SEQUENCE: 9
uaagaacucu ccacuggagc cc                                            22

<210> SEQ ID NO 10
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylguanosine-3'-phosphorothioate
```

```
<220> FEATURE:
<221> NAME/KEY: modified_base
<222> LOCATION: (2)..(2)
<223> OTHER INFORMATION: 2'-O-methylcytidine-3'-phosphorothioate
<220> FEATURE:
<221> NAME/KEY: modified_base
<222> LOCATION: (3)..(3)
<223> OTHER INFORMATION: tm
<220> FEATURE:
<221> NAME/KEY: modified_base
<222> LOCATION: (4)..(5)
<223> OTHER INFORMATION: cm
<220> FEATURE:
<221> NAME/KEY: modified_base
<222> LOCATION: (6)..(6)
<223> OTHER INFORMATION: 2'-O-methyladenosine-3'-phosphate
<220> FEATURE:
<221> NAME/KEY: modified_base
<222> LOCATION: (7)..(7)
<223> OTHER INFORMATION: 2'-fluoroguanosine-3'-phosphate
<220> FEATURE:
<221> NAME/KEY: modified_base
<222> LOCATION: (8)..(8)
<223> OTHER INFORMATION: tm
<220> FEATURE:
<221> NAME/KEY: modified_base
<222> LOCATION: (9)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(16)
<223> OTHER INFORMATION: tm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(19)
<223> OTHER INFORMATION: tm
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: N-[tris(GalNAc-alkyl)-amidodecanoyl]-4-
     hydroxyprolinol Hyp-(GalNAc-alkyl)3

<400> SEQUENCE: 10
gcuccagugg agaguucuua c                                            21

<210> SEQ ID NO 11
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: modified_base
```

```
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-fluorouridine-3'-phosphate
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(13)
<223> OTHER INFORMATION: cm
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (17)..(18)
<223> OTHER INFORMATION: gm
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: gm
<220> FEATURE:
<221> NAME/KEY: modified_base
<222> LOCATION: (21)..(22)
<223> OTHER INFORMATION: 2'-O-methylcytidine-3'-phosphorothioate
<220> FEATURE:
<221> NAME/KEY: modified_base
<222> LOCATION: (23)..(23)
<223> OTHER INFORMATION: cm

<400> SEQUENCE: 11
guaagaacuc uccacuggag ccc                                           23

<210> SEQ ID NO 12
<211> LENGTH: 19
<212> TYPE: RNA
<213> ORGANISM: Artificial Sequence
<220> FEATURE:
<223> OTHER INFORMATION: siRNA
<220> FEATURE:
```

```
<221> NAME/KEY: modified_base
<222> LOCATION: (1)..(1)
<223> OTHER INFORMATION: 2'-O-methylcytidine-3'-phosphorothioate
<220> FEATURE:
<221> NAME/KEY: modified_base
<222> LOCATION: (2)..(2)
<223> OTHER INFORMATION: 2'-O-methyl-5-methyluridine-3'-phosphorothioate
<220> FEATURE:
<221> NAME/KEY: modified_base
<222> LOCATION: (3)..(4)
<223> OTHER INFORMATION: cm
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-5-methyluridine-3'-phosphate
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoroguanosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluoroguanosine-3'-phosphate
<220> FEATURE:
<221> NAME/KEY: modified_base
<222> LOCATION: (12)..(12)
<223> OTHER INFORMATION: 2'-O-methyladenosine-3'-phosphate
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(15)
<223> OTHER INFORMATION: tm
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(18)
<223> OTHER INFORMATION: tm
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: N-[tris(GalNAc-alkyl)-amidodecanoyl]-4-
      hydroxyprolinol Hyp-(GalNAc-alkyl)3

<400> SEQUENCE: 12
cuccagugga gaguucuua                                                  19

<210> SEQ ID NO 13
<211> LENGTH: 21
<212> TYPE: RNA
<213> ORGANISM: Artificial Sequence
<220> FEATURE:
```

```
<223> OTHER INFORMATION: siRNA
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluorouridine-3'-phosphate
<220> FEATURE:
<221> NAME/KEY: modified_base
<222> LOCATION: (9)..(9)
<223> OTHER INFORMATION: 2'-fluorocytidine-3'-phosphate
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoroguanosine-3'-phosphate
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methylguanosine-3'-phosphorothioate
<220> FEATURE:
<221> NAME/KEY: modified_base
<222> LOCATION: (20)..(20)
<223> OTHER INFORMATION: 2'-O-methylcytidine-3'-phosphorothioate
<220> FEATURE:
<221> NAME/KEY: modified_base
<222> LOCATION: (21)..(21)
<223> OTHER INFORMATION: cm

<400> SEQUENCE: 13
```
uaagaacucu ccacuggagc c					21

<210> SEQ ID NO 14
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylcytidine-3'-phosphorothioate
<220> FEATURE:
<221> NAME/KEY: modified_base
<222> LOCATION: (2)..(2)
<223> OTHER INFORMATION: 2'-O-methyl-5-methyluridine-3'-phosphorothioate
<220> FEATURE:
<221> NAME/KEY: modified_base
<222> LOCATION: (3)..(4)
<223> OTHER INFORMATION: cm
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-5-methyluridine-3'-phosphate
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoroguanosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluoroguanosine-3'-phosphate
<220> FEATURE:
<221> NAME/KEY: modified_base
<222> LOCATION: (12)..(12)
<223> OTHER INFORMATION: 2'-O-methyladenosine-3'-phosphate
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(15)
<223> OTHER INFORMATION: tm
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(18)
<223> OTHER INFORMATION: tm
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: cm
<220> FEATURE:

<221> NAME/KEY: modified_base
<222> LOCATION: (20)..(20)
<223> OTHER INFORMATION: N-[tris(GalNAc-alkyl)-amidodecanoyl]-4-
    hydroxyprolinol Hyp-(GalNAc-alkyl)3

<400> SEQUENCE: 14
cuccagugga gaguucuuac                                                   20

<210> SEQ ID NO 15
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylguanosine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-fluorouridine-3'-phosphate
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(13)
<223> OTHER INFORMATION: cm
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(18)
<223> OTHER INFORMATION: gm
<220> FEATURE:
<221> NAME/KEY: modified_base
<222> LOCATION: (19)..(19)

```
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methylguanosine-3'-phosphorothioate
<220> FEATURE:
<221> NAME/KEY: modified_base
<222> LOCATION: (21)..(21)
<223> OTHER INFORMATION: 2'-O-methylcytidine-3'-phosphorothioate
<220> FEATURE:
<221> NAME/KEY: modified_base
<222> LOCATION: (22)..(22)
<223> OTHER INFORMATION: cm

<400> SEQUENCE: 15
guaagaacuc uccacuggag cc                                              22

<210> SEQ ID NO 16
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylcytidine-3'-phosphorothioate
<220> FEATURE:
<221> NAME/KEY: modified_base
<222> LOCATION: (2)..(2)
<223> OTHER INFORMATION: 2'-O-methyl-5-methyluridine-3'-phosphorothioate
<220> FEATURE:
<221> NAME/KEY: modified_base
<222> LOCATION: (3)..(4)
<223> OTHER INFORMATION: cm
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoroguanosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluoroguanosine-3'-phosphate
<220> FEATURE:
<221> NAME/KEY: modified_base
<222> LOCATION: (12)..(12)
<223> OTHER INFORMATION: 2'-O-methyladenosine-3'-phosphate
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(15)
<223> OTHER INFORMATION: tm
<220> FEATURE:
<221> NAME/KEY: modified_base
<222> LOCATION: (16)..(16)
<223> OTHER INFORMATION: cm
<220> FEATURE:
<221> NAME/KEY: modified_base
```

<222> LOCATION: (17)..(18)
<223> OTHER INFORMATION: tm
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (21)..(21)
<223> OTHER INFORMATION: N-[tris(GalNAc-alkyl)-amidodecanoyl]-4-
      hydroxyprolinol Hyp-(GalNAc-alkyl)3

<400> SEQUENCE: 16
cuccagugga gaguucuuac g                                              21

<210> SEQ ID NO 17
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylcytidine-3'-phosphorothioate
<220> FEATURE:
<221> NAME/KEY: modified_base
<222> LOCATION: (2)..(2)
<223> OTHER INFORMATION: 2'-fluoroguanosine-3'-phosphorothioate
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroguanosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-fluorocytidine-3'-phosphate
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm

```
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (21)..(21)
<223> OTHER INFORMATION: 2'-O-methylguanosine-3'-phosphorothioate
<220> FEATURE:
<221> NAME/KEY: modified_base
<222> LOCATION: (22)..(22)
<223> OTHER INFORMATION: 2'-O-methylcytidine-3'-phosphorothioate
<220> FEATURE:
<221> NAME/KEY: modified_base
<222> LOCATION: (23)..(23)
<223> OTHER INFORMATION: cm

<400> SEQUENCE: 17
cguaagaacu cuccacugga gcc                                             23

<210> SEQ ID NO 18
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methyl-5-methyluridine-3'-phosphorothioate
<220> FEATURE:
<221> NAME/KEY: modified_base
<222> LOCATION: (2)..(2)
<223> OTHER INFORMATION: 2'-O-methylcytidine-3'-phosphorothioate
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: tm
<220> FEATURE:
<221> NAME/KEY: modified_base
<222> LOCATION: (7)..(7)
<223> OTHER INFORMATION: 2'-fluoroguanosine-3'-phosphate
<220> FEATURE:
<221> NAME/KEY: modified_base
<222> LOCATION: (8)..(8)
```

```
<223> OTHER INFORMATION: gm
<220> FEATURE:
<221> NAME/KEY: modified_base
<222> LOCATION: (9)..(9)
<223> OTHER INFORMATION: 2'-fluoroadenosine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(14)
<223> OTHER INFORMATION: tm
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(17)
<223> OTHER INFORMATION: tm
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (19)..(19)
<223> OTHER INFORMATION: N-[tris(GalNAc-alkyl)-amidodecanoyl)]-4-
     hydroxyprolinol Hyp-(GalNAc-alkyl)3

<400> SEQUENCE: 18
uccaguggag aguucuuac                                                  19

<210> SEQ ID NO 19
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylguanosine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
```

```
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-fluorouridine-3'-phosphate
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(13)
<223> OTHER INFORMATION: cm
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(18)
<223> OTHER INFORMATION: gm
<220> FEATURE:
<221> NAME/KEY: modified_base
<222> LOCATION: (19)..(19)
<223> OTHER INFORMATION: 2'-O-methyladenosine-3'-phosphorothioate
<220> FEATURE:
<221> NAME/KEY: modified_base
<222> LOCATION: (20)..(20)
<223> OTHER INFORMATION: 2'-O-methylguanosine-3'-phosphorothioate
<220> FEATURE:
<221> NAME/KEY: modified_base
<222> LOCATION: (21)..(21)
<223> OTHER INFORMATION: cm

<400> SEQUENCE: 19
guaagaacuc uccacuggag c                                        21

<210> SEQ ID NO 20
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methyl-5-methyluridine-3'-phosphorothioate
<220> FEATURE:
<221> NAME/KEY: modified_base
<222> LOCATION: (2)..(2)
<223> OTHER INFORMATION: 2'-O-methylcytidine-3'-phosphorothioate
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: gm
```

-continued

```
<220> FEATURE:
<221> NAME/KEY: modified_base
<222> LOCATION: (6)..(6)
<223> OTHER INFORMATION: tm
<220> FEATURE:
<221> NAME/KEY: modified_base
<222> LOCATION: (7)..(7)
<223> OTHER INFORMATION: 2'-fluoroguanosine-3'-phosphate
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoroadenosine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(14)
<223> OTHER INFORMATION: tm
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(17)
<223> OTHER INFORMATION: tm
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: gm
<220> FEATURE:
<221> NAME/KEY: modified_base
<222> LOCATION: (20)..(20)
<223> OTHER INFORMATION: N-[tris(GalNAc-alkyl)-amidodecanoyl]-4-
      hydroxyprolinol Hyp-(GalNAc-alkyl)3

<400> SEQUENCE: 20
uccaguggag aguucuuacg                                              20

<210> SEQ ID NO 21
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylcytidine-3'-phosphorothioate
<220> FEATURE:
<221> NAME/KEY: modified_base
<222> LOCATION: (2)..(2)
<223> OTHER INFORMATION: 2'-fluoroguanosine-3'-phosphorothioate
<220> FEATURE:
<221> NAME/KEY: modified_base
```

```
<222> LOCATION: (3)..(3)
<223> OTHER INFORMATION: um
<220> FEATURE:
<221> NAME/KEY: modified_base
<222> LOCATION: (4)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroguanosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-fluorocytidine-3'-phosphate
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine-3'-phosphorothioate
<220> FEATURE:
<221> NAME/KEY: modified_base
<222> LOCATION: (21)..(21)
<223> OTHER INFORMATION: 2'-O-methylguanosine-3'-phosphorothioate
<220> FEATURE:
<221> NAME/KEY: modified_base
<222> LOCATION: (22)..(22)
<223> OTHER INFORMATION: cm

<400> SEQUENCE: 21
cguaagaacu cuccacugga gc                                              22

<210> SEQ ID NO 22
<211> LENGTH: 21
<212> TYPE: RNA
```

```
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methyl-5-methyluridine-3'-phosphorothioate
<220> FEATURE:
<221> NAME/KEY: modified_base
<222> LOCATION: (2)..(2)
<223> OTHER INFORMATION: 2'-O-methylcytidine-3'-phosphorothioate
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: tm
<220> FEATURE:
<221> NAME/KEY: modified_base
<222> LOCATION: (7)..(7)
<223> OTHER INFORMATION: 2'-fluoroguanosine-3'-phosphate
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoroadenosine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(14)
<223> OTHER INFORMATION: tm
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(17)
<223> OTHER INFORMATION: tm
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: gm
<220> FEATURE:
<221> NAME/KEY: modified_base
<222> LOCATION: (21)..(21)
<223> OTHER INFORMATION: tm
```

-continued

```
<220> FEATURE:
<221> NAME/KEY: modified_base
<222> LOCATION: (21)..(21)
<223> OTHER INFORMATION: N-[tris(GalNAc-alkyl)-amidodecanoyl]-4-
      hydroxyprolinol Hyp-(GalNAc-alkyl)3

<400> SEQUENCE: 22
uccaguggag aguucuuacg u                                              21

<210> SEQ ID NO 23
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(9)
<223> OTHER INFORMATION: 2'-fluoroadenosine-3'-phosphate
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
```

```
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(20)
<223> OTHER INFORMATION: gm
<220> FEATURE:
<221> NAME/KEY: modified_base
<222> LOCATION: (21)..(21)
<223> OTHER INFORMATION: 2'-O-methyladenosine-3'-phosphorothioate
<220> FEATURE:
<221> NAME/KEY: modified_base
<222> LOCATION: (22)..(22)
<223> OTHER INFORMATION: 2'-O-methylguanosine-3'-phosphorothioate
<220> FEATURE:
<221> NAME/KEY: modified_base
<222> LOCATION: (23)..(23)
<223> OTHER INFORMATION: cm

<400> SEQUENCE: 23
ucguaagaac ucuccacugg agc                                              23

<210> SEQ ID NO 24
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(2)
<223> OTHER INFORMATION: 2'-O-methylguanosine-3'-phosphorothioate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-5-methyluridine-3'-phosphate
<220> FEATURE:
<221> NAME/KEY: modified_base
<222> LOCATION: (8)..(8)
<223> OTHER INFORMATION: tm
<220> FEATURE:
<221> NAME/KEY: modified_base
<222> LOCATION: (9)..(9)
<223> OTHER INFORMATION: 2'-fluorocytidine-3'-phosphate
<220> FEATURE:
<221> NAME/KEY: modified_base
<222> LOCATION: (10)..(11)
<223> OTHER INFORMATION: 2'-fluoro-5-methyluridine-3'-phosphate
<220> FEATURE:
<221> NAME/KEY: modified_base
<222> LOCATION: (12)..(12)
<223> OTHER INFORMATION: 2'-O-methyladenosine-3'-phosphate
<220> FEATURE:
<221> NAME/KEY: modified_base
<222> LOCATION: (13)..(13)
<223> OTHER INFORMATION: cm
<220> FEATURE:
```

```
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (19)..(19)
<223> OTHER INFORMATION: N-[tris(GalNAc-alkyl)-amidodecanoyl)]-4-
      hydroxyprolinol Hyp-(GalNAc-alkyl)3

<400> SEQUENCE: 24
ggagaguucu uacgacacg                                              19

<210> SEQ ID NO 25
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylcytidine-3'-phosphorothioate
<220> FEATURE:
<221> NAME/KEY: modified_base
<222> LOCATION: (2)..(2)
<223> OTHER INFORMATION: 2'-fluoroguanosine-3'-phosphorothioate
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluorocytidine-3'-phosphate
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-fluorouridine-3'-phosphate
<220> FEATURE:
<221> NAME/KEY: modified_base
<222> LOCATION: (9)..(9)
<223> OTHER INFORMATION: 2'-fluoroadenosine-3'-phosphate
<220> FEATURE:
<221> NAME/KEY: modified_base
<222> LOCATION: (10)..(10)
```

```
<223> OTHER INFORMATION: 2'-O-methyladenosine-3'-phosphate
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-O-methylcytidine-3'-phosphorothioate
<220> FEATURE:
<221> NAME/KEY: modified_base
<222> LOCATION: (20)..(20)
<223> OTHER INFORMATION: 2'-O-methyladenosine-3'-phosphorothioate
<220> FEATURE:
<221> NAME/KEY: modified_base
<222> LOCATION: (21)..(21)
<223> OTHER INFORMATION: cm

<400> SEQUENCE: 25
cgugucguaa gaacucucca c                                              21

<210> SEQ ID NO 26
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(2)
<223> OTHER INFORMATION: 2'-O-methylguanosine-3'-phosphorothioate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-5-methyluridine-3'-phosphate
<220> FEATURE:
<221> NAME/KEY: modified_base
```

```
<222> LOCATION: (8)..(8)
<223> OTHER INFORMATION: tm
<220> FEATURE:
<221> NAME/KEY: modified_base
<222> LOCATION: (9)..(9)
<223> OTHER INFORMATION: 2'-fluorocytidine-3'-phosphate
<220> FEATURE:
<221> NAME/KEY: modified_base
<222> LOCATION: (10)..(11)
<223> OTHER INFORMATION: 2'-fluoro-5-methyluridine-3'-phosphate
<220> FEATURE:
<221> NAME/KEY: modified_base
<222> LOCATION: (12)..(12)
<223> OTHER INFORMATION: 2'-O-methyladenosine-3'-phosphate
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: tm
<220> FEATURE:
<221> NAME/KEY: modified_base
<222> LOCATION: (20)..(20)
<223> OTHER INFORMATION: N-[tris(GalNAc-alkyl)-amidodecanoyl)]-4-
      hydroxyprolinol Hyp-(GalNAc-alkyl)3

<400> SEQUENCE: 26
ggagaguucu uacgacacgu                                            20

<210> SEQ ID NO 27
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methyladenosine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: um
```

```
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-fluorouridine-3'-phosphate
<220> FEATURE:
<221> NAME/KEY: modified_base
<222> LOCATION: (10)..(11)
<223> OTHER INFORMATION: 2'-O-methyladenosine-3'-phosphate
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: 2'-O-methylcytidine-3'-phosphorothioate
<220> FEATURE:
<221> NAME/KEY: modified_base
<222> LOCATION: (21)..(21)
<223> OTHER INFORMATION: 2'-O-methyladenosine-3'-phosphorothioate
<220> FEATURE:
<221> NAME/KEY: modified_base
<222> LOCATION: (22)..(22)
<223> OTHER INFORMATION: cm

<400> SEQUENCE: 27
acgugucgua agaacucucc ac                                             22

<210> SEQ ID NO 28
<211> LENGTH: 21
<212> TYPE: RNA
<213> ORGANISM: Artificial Sequence
<220> FEATURE:
```

```
<223> OTHER INFORMATION: siRNA
<220> FEATURE:
<221> NAME/KEY: modified_base
<222> LOCATION: (1)..(2)
<223> OTHER INFORMATION: 2'-O-methylguanosine-3'-phosphorothioate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-5-methyluridine-3'-phosphate
<220> FEATURE:
<221> NAME/KEY: modified_base
<222> LOCATION: (8)..(8)
<223> OTHER INFORMATION: tm
<220> FEATURE:
<221> NAME/KEY: modified_base
<222> LOCATION: (9)..(9)
<223> OTHER INFORMATION: 2'-fluorocytidine-3'-phosphate
<220> FEATURE:
<221> NAME/KEY: modified_base
<222> LOCATION: (10)..(11)
<223> OTHER INFORMATION: 2'-fluoro-5-methyluridine-3'-phosphate
<220> FEATURE:
<221> NAME/KEY: modified_base
<222> LOCATION: (12)..(12)
<223> OTHER INFORMATION: 2'-O-methyladenosine-3'-phosphate
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: tm
<220> FEATURE:
<221> NAME/KEY: modified_base
<222> LOCATION: (21)..(21)
<223> OTHER INFORMATION: cm
<220> FEATURE:
<221> NAME/KEY: modified_base
```

```
<222> LOCATION: (21)..(21)
<223> OTHER INFORMATION: N-[tris(GalNAc-alkyl)-amidodecanoyl]-4-
      hydroxyprolinol Hyp-(GalNAc-alkyl)3

<400> SEQUENCE: 28
ggagaguucu uacgacacgu c                                              21

<210> SEQ ID NO 29
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylguanosine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoroguanosine-3'-phosphate
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-fluoroguanosine-3'-phosphate
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: 2'-O-methyladenosine-3'-phosphate
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: um
```

```
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: 2'-O-methylcytidine-3'-phosphorothioate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: cm

<400> SEQUENCE: 29
gacgugucgu aagaacucuc cac                                               23

<210> SEQ ID NO 30
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: t
<220> FEATURE:
<221> NAME/KEY: modified_base
<222> LOCATION: (8)..(8)
<223> OTHER INFORMATION: t
<220> FEATURE:
<221> NAME/KEY: modified_base
<222> LOCATION: (15)..(16)
<223> OTHER INFORMATION: t
<220> FEATURE:
<221> NAME/KEY: modified_base
<222> LOCATION: (18)..(19)
<223> OTHER INFORMATION: t

<400> SEQUENCE: 30
gcuccagtgg agaguucuut t                                                 21

<210> SEQ ID NO 31
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: t
<220> FEATURE:
<221> NAME/KEY: modified_base
<222> LOCATION: (5)..(5)
<223> OTHER INFORMATION: t
<220> FEATURE:
<221> NAME/KEY: modified_base
<222> LOCATION: (8)..(8)
<223> OTHER INFORMATION: t
<220> FEATURE:
<221> NAME/KEY: modified_base
<222> LOCATION: (15)..(15)
```

```
<223> OTHER INFORMATION: t
<220> FEATURE:
<221> NAME/KEY: modified_base
<222> LOCATION: (17)..(17)
<223> OTHER INFORMATION: t

<400> SEQUENCE: 31
cgugucguaa gaacucucct t                                              21

<210> SEQ ID NO 32
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (2)..(2)
<223> OTHER INFORMATION: t
<220> FEATURE:
<221> NAME/KEY: modified_base
<222> LOCATION: (7)..(7)
<223> OTHER INFORMATION: t
<220> FEATURE:
<221> NAME/KEY: modified_base
<222> LOCATION: (14)..(15)
<223> OTHER INFORMATION: t
<220> FEATURE:
<221> NAME/KEY: modified_base
<222> LOCATION: (17)..(18)
<223> OTHER INFORMATION: t

<400> SEQUENCE: 32
cuccagugga gaguucuuat t                                              21

<210> SEQ ID NO 33
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (2)..(2)
<223> OTHER INFORMATION: t
<220> FEATURE:
<221> NAME/KEY: modified_base
<222> LOCATION: (9)..(9)
<223> OTHER INFORMATION: t
<220> FEATURE:
<221> NAME/KEY: modified_base
<222> LOCATION: (11)..(11)
<223> OTHER INFORMATION: t
<220> FEATURE:
<221> NAME/KEY: modified_base
<222> LOCATION: (16)..(16)
<223> OTHER INFORMATION: t

<400> SEQUENCE: 33
guaagaacuc uccacuggat t                                              21

<210> SEQ ID NO 34
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: t
<220> FEATURE:
<221> NAME/KEY: modified_base
```

```
<222> LOCATION: (6)..(6)
<223> OTHER INFORMATION: t
<220> FEATURE:
<221> NAME/KEY: modified_base
<222> LOCATION: (13)..(14)
<223> OTHER INFORMATION: t
<220> FEATURE:
<221> NAME/KEY: modified_base
<222> LOCATION: (16)..(17)
<223> OTHER INFORMATION: t

<400> SEQUENCE: 34
uccaguggag aguucuuact t                                              21

<210> SEQ ID NO 35
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: t
<220> FEATURE:
<221> NAME/KEY: modified_base
<222> LOCATION: (8)..(8)
<223> OTHER INFORMATION: t
<220> FEATURE:
<221> NAME/KEY: modified_base
<222> LOCATION: (10)..(10)
<223> OTHER INFORMATION: t
<220> FEATURE:
<221> NAME/KEY: modified_base
<222> LOCATION: (15)..(15)
<223> OTHER INFORMATION: t

<400> SEQUENCE: 35
uaagaacucu ccacuggagt t                                              21

<210> SEQ ID NO 36
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (7)..(8)
<223> OTHER INFORMATION: t
<220> FEATURE:
<221> NAME/KEY: modified_base
<222> LOCATION: (10)..(11)
<223> OTHER INFORMATION: t

<400> SEQUENCE: 36
ggagaguucu uacgacacgt t                                              21

<210> SEQ ID NO 37
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (7)..(7)
<223> OTHER INFORMATION: t
<220> FEATURE:
<221> NAME/KEY: modified_base
<222> LOCATION: (9)..(9)
<223> OTHER INFORMATION: t
<220> FEATURE:
```

```
<221> NAME/KEY: modified_base
<222> LOCATION: (14)..(14)
<223> OTHER INFORMATION: t

<400> SEQUENCE: 37
aagaacucuc cacuggagct t                                              21

<210> SEQ ID NO 38
<211> LENGTH: 53
<212> TYPE: DNA
<213> ORGANISM: homo sapiens

<400> SEQUENCE: 38
ggccatggtc agcgtgaacg cgcccctcgg ggctccagtg gagagttctt acg           53

<210> SEQ ID NO 39
<211> LENGTH: 27
<212> TYPE: DNA
<213> ORGANISM: homo sapiens

<400> SEQUENCE: 39
gctccagtgg agagttctta cgacacg                                        27

<210> SEQ ID NO 40
<211> LENGTH: 19
<212> TYPE: DNA
<213> ORGANISM: homo sapeins

<400> SEQUENCE: 40
gctccagtgg agagttctt                                                 19

<210> SEQ ID NO 41
<211> LENGTH: 19
<212> TYPE: DNA
<213> ORGANISM: homo sapeins

<400> SEQUENCE: 41
ctccagtgga gagttctta                                                 19

<210> SEQ ID NO 42
<211> LENGTH: 19
<212> TYPE: DNA
<213> ORGANISM: homo sapeins

<400> SEQUENCE: 42
tccagtggag agttcttac                                                 19

<210> SEQ ID NO 43
<211> LENGTH: 18
<212> TYPE: DNA
<213> ORGANISM: homo sapiens

<400> SEQUENCE: 43
ggagagttct tacgacac                                                  18

<210> SEQ ID NO 44
<211> LENGTH: 63
<212> TYPE: DNA
```

```
<213> ORGANISM: homo sapiens

<400> SEQUENCE: 44
ggccatggtc agcgtgaacg cgcccctcgg ggctccagtg gagagttctt acgacacgtc    60
ccc                                                                  63
```

SILENCING OF HNF4α-P2 ISOFORMS WITH SIRNA TO IMPROVE HEPATOCYTE FUNCTION IN LIVER FAILURE

CROSS REFERENCE TO RELATED APPLICATIONS

This application is a Divisional of U.S. patent application Ser. No. 16/670,122 filed Oct. 31, 2019, which claims the benefit of U.S. Provisional Patent Application No. 62/753, 299, filed Oct. 31, 2018 and U.S. Provisional Patent Application No. 62/757,944, filed Nov. 9, 2018, each of which is incorporated herein by reference in its entirety.

STATEMENT REGARDING FEDERAL FUNDING

This invention was made with government support under Grant Nos. AA021908 and AA026972 awarded by the National Institutes of Health. The government has certain rights in the invention.

SEQUENCE LISTING

The Sequence Listing associated with this application is filed in electronic format via EFS-Web and is hereby incorporated by reference into the specification in its entirety. The name of the text file containing the Sequence Listing is 2006790_ST25.txt. The size of the text file is 62,080 bytes, and the text file was created on Sep. 21, 2023.

Liver-related mortality has increased in the last decade, partially due to the higher incidence of addictions in the form of alcohol-related cirrhosis. The prognosis of alcohol-related liver disease (ALD) depends on the development of liver failure, mainly in the form of alcoholic hepatitis (AH). The burden of AH has increased in many countries and represents an important public health problem. The genetic and epigenetic factors involved in the development of AH in heavy drinkers are not well known. Genome-wide association studies (GWAS) have shown that variations in PNPLA3 (patatin like phospholipase domain containing 3), MBOAT7 (membrane-bound O-acetyltransferase domain-containing protein 7), and TM6SF2 (transmembrane 6 superfamily member 2) loci confer risk for alcohol-related cirrhosis, but the association of specific loci with AH is unknown. Because alcohol abuse has been associated with DNA methylation changes in humans and epigenetic dysregulation in experimental liver injury, it is conceivable that epigenetic factors play a role in AH. Liver failure in the setting of AH was traditionally considered to be secondary to a flare in intrahepatic inflammation. Consequently, therapies have been directed towards decreasing inflammatory mediators (e.g., prednisolone), with limited efficacy. Bilirubinostasis, inefficient regeneration of hepatocytes and a compensatory ductular reaction may play a pathogenic role in AH. However, the mechanisms of liver failure in the setting of AH remain obscure.

Liver failure is a common cause of morbidity and mortality. There are no targeted therapies to improve liver function. Alcoholic hepatitis (AH), a common cause of liver failure, is a life-threatening condition characterized by profound hepatocellular dysfunction for which targeted treatments are urgently needed.

SUMMARY

Provided herein is a method of treating a patient having liver damage or liver failure. The method comprises knocking down or inhibiting expression of a hepatocyte nuclear factor 4 alpha mRNA transcribed from its P2 promoter (HNF4α-P2 isoform mRNA) in the patient, or reducing activity of the protein encoded by the HNF4α-P2 isoform mRNA, thereby treating the liver damage or liver failure in the patient.

Also provided herein is a method of knocking down expression of an HNF4α-P2 isoform mRNA in a cell. The method comprises contacting the cell with an RNAi agent for selectively knocking down expression of an HNF4α-P2 isoform mRNA, in an amount effective to reduce production of the protein product of the HNF4α-P2 isoform mRNA in a cell.

Also provided herein is an RNAi agent targeting exon 1D of HFN4α.

BRIEF DESCRIPTION OF THE DRAWINGS

(FIG. 1A) Transcription factor footprint analysis between early ASH and AH patient livers. Most significant differentially expressed (DE) genes in the comparison between early ASH and AH patients. Predicted activation by IPA expressed as ZS (left) and motif enrichment by Opossum as ZS and FS (right). Left, TF binding motif enrichment by Opossum analysis is expressed as ZS and Fisher test Score (FS). Right, predicted activation by IPA analysis expressed as ZS. (FIG. 1B) Selected target genes of HNF4a identified by IPA analysis. Fold Change (FC) in Normal vs Early ASH and between Early ASH and AH are presented. All genes in (b) had a $FDR<10^{-6}$ in DE analysis.

FIGS. 2A-2S. Fetal HNF4a-P2 isoform is increased in patients with AH-related liver failure and its inhibition increases HNF4a-P1 expression and function. (FIG. 2A) Combined graph showing levels of bilirubin, INR, and albumin levels in serum along ALD progression (values expressed as Mean+/−SEM) and HNF4a footprint for each comparison against control group (values expressed as ZScore from Ingenuity Pathway Analysis). (FIG. 2I) Pearson correlation index among mRNA levels of HNF4A-P1 dependent genes (PCK1, CYP2E1, ALB) and of non-hepatocyte genes related to ductular metaplasia (EPCAM, KRT7), epithelial-to-mesenchymal transition (VIM) and hepatocyte pro-inflammatory genes (IL8). (FIGS. 2J and 2K) HepG2 cells were transfected with plasmids encoding P1 (HNF4a2) and P2

(HNF4a8) variants. P1 was maintained at the same dose while P2 was increased as indicated. RNA was extracted 12 h and 24 h after transfection (n=3 for each group). qPCR of (FIG. 2J) HNF4a-P2 isoform and (FIG. 2K) PCK1. (FIGS. 2L-2Q) HepG2 cells were transfected with siRNA complementary to the first exon (1E) of HNF4a-P2 isoforms (n=3 for each group), and RNA and protein was extracted at 48 h after transfection. (1-m) levels of HNF4a-P2 (FIG. 2L) mRNA and (FIG. 2M) protein. (FIGS. 2N-2Q) mRNA levels of (FIG. 2N) HNF4a-P1, (FIG. 2O) HNF4A-AS1 lncRNA and of HNF4a-P1 targets (FIG. 2P) biosynthetic-related genes PCK1, ALB, F7 and (FIG. 2Q) bile acid synthesis and transport genes CYP7A1, BSEP, and CYP27A1. (FIGS. 2R and 2S) Primary hepatocytes were silenced with siRNA-HNF4A-P2 and supernatant was collected 48 h after transfection (n=3 for each group). Total bile acids (FIG. 2R) and glucose production (FIG. 2S) were quantified. Significance was determined by unpaired, two-tailed Student's test in FIGS. 2A and 2C, by Fisher exact probability test in FIG. 2D and by two-tailed Mann-Whitney U test in FIGS. 2F-2H, 2J-2K, 2L, and 2N-2S: *P<0.05, P<0.01, *P<0.001. Pearson Correlation test was applied in FIG. 2I, values inside the box indicate R coefficient for each correlation. For box-and-whisker plots: perimeters, 25th-75th percentile; midline, median; whiskers, minimum to maximum values; individual data points are represented. Gene expression are presented as relative values normalized to the mean of the control. Western blot in (FIG. 2M) was performed in different experiments in HepG2 (n=3) and in Hep3B (n=3) cells, representative blot is presented here.

(FIGS. 3A-3F) HepG2 cells were transfected with siRNA complementary to the first exon (1E) of HNF4a-P2 isoforms, and RNA and nuclear proteins were extracted at 48 h after transfection and 8 h (RNA) or 24 h (Nuclei) after TGFb1 treatment (5 ng/ml) (n=4 for each condition). (FIGS. 3A and 3B) levels of HNF4a-P2 (FIG. 3A) mRNA and (FIG. 3B) protein. (FIGS. 3C and 3D) mRNA levels of HNF4a-P1 targets (FIG. 3C) biosynthetic-related genes PCK1, ALB, F7 and (FIG. 3D) bile acid synthesis and transport genes CYP7A1, BSEP. (FIGS. 3E and 3F) Primary human hepatocytes were silenced with siRNA-HNF4a-P2 and supernatant was collected 48 h after transfection and 8 h after TGFb1 treatment (5 ng/ml) (n=3 for each condition). Total bile acids (FIG. 3E) and Glucose production (FIG. 3F) were quantified. Significance was determined by two-tailed Mann-Whitney U test in a, c, d, and e: *P<0.05, **P<0.01. For box-and-whisker plots: perimeters, 25th-75th percentile; midline, median; whiskers, minimum to maximum values; individual data points are represented. Gene expression is presented as relative values normalized to the mean of the control.

FIGS. 4A and 4B (continuous) provide an exemplary nucleotide sequence for an HNF4A transcript variant (NM_175914.4 Homo sapiens hepatocyte nuclear factor 4 alpha (HNF4A), transcript variant 5, mRNA (SEQ ID NO: 1)).

FIGS. 5A, 5B, and 6 provide non-limiting additional examples of HNFA isoforms initiating from the P2 promoter, including HNF4 alpha7 (NM_001030003.2, FIGS. 5A and 5B, continuous, SEQ ID NO: 2) and HNF4 alpha9 (NM_001030004.2, FIG. 6, SEQ ID NO: 3).

FIG. 7A provide exemplary additional oligomers useful as RNAi agents for inhibition of HNF4α-P2 isoforms based on GenBank accession No. NM_175914.4. FIG. 7B provides a legend for nucleotide modifications shown in FIG. 7A (SEQ ID NOS: 4-37).

DETAILED DESCRIPTION

Figure 1A:
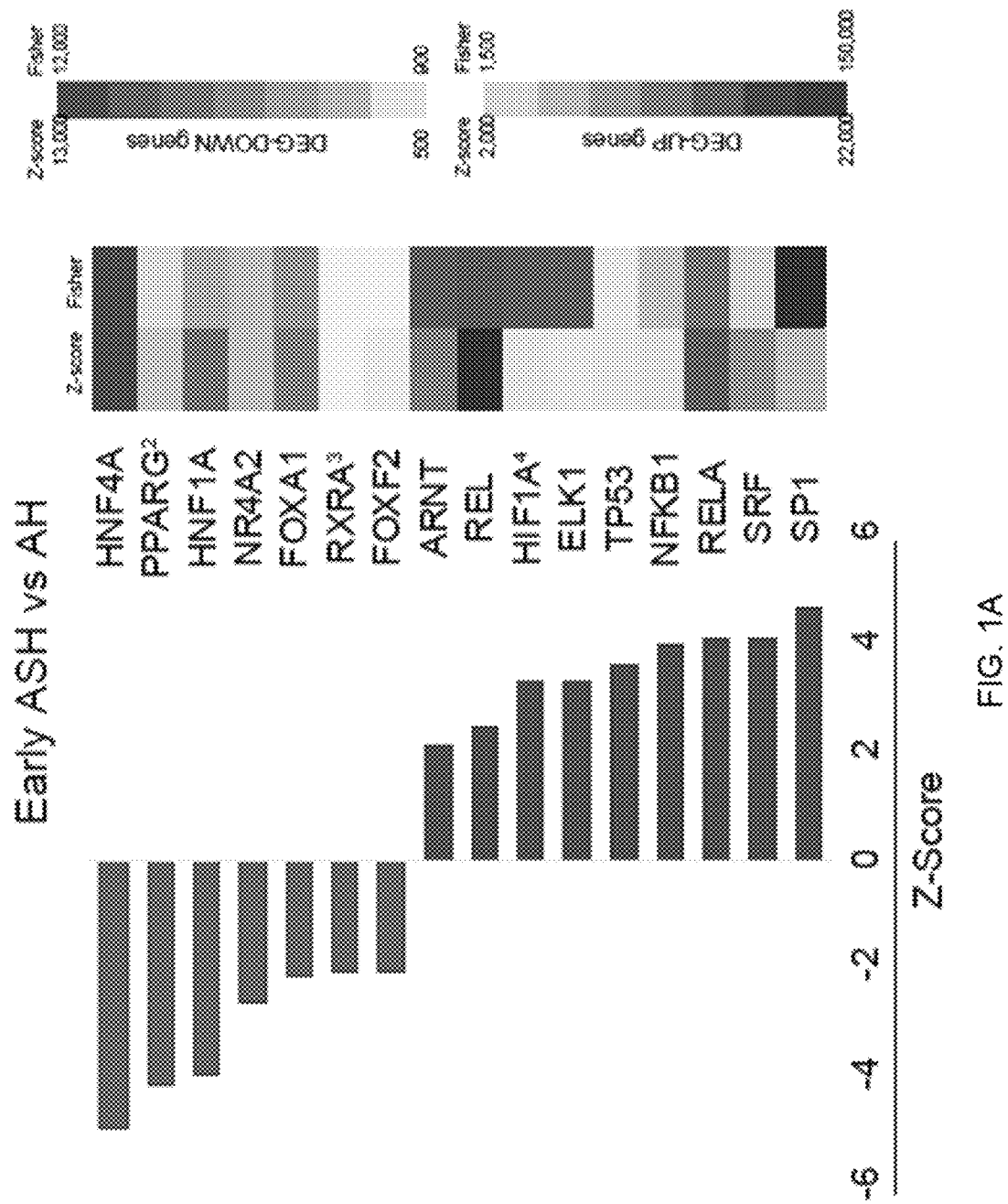
FIGS. 1A and 1B. Liver transcriptome analysis in patients with ALD show deficient predicted activity of LETFs in AH.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

As used herein, the term "patient" or "subject" refers to members of the animal kingdom including but not limited to human beings and "mammal" refers to all mammals, including, but not limited to human beings.

As used herein, the "treatment" or "treating" of liver disease, liver damage, liver inflammation, or liver failure, such as acute liver failure, ALD, AH, or Acute-on-Chronic Liver Failure (ACLF), means administration to a patient by any suitable dosage regimen, procedure and/or administration route of a composition, device, or structure with the object of achieving a beneficial or desirable clinical/medical end-point, including but not limited to, preventing, reducing, and/or eliminating any symptom of liver disease, liver damage, liver cirrhosis, liver inflammation, or liver failure, such as acute liver failure, ALD, AH, or ACLF, such as liver damage or liver inflammation. An amount of any agent, administered by any suitable route, effective to treat a patient is an amount capable of preventing, reducing, and/or eliminating any symptom of liver disease, liver damage, liver inflammation, or liver failure, such as acute liver failure, ALD, AH, or ACLF, such as liver damage or liver failure in a patient. Liver damage and Liver failure, as well as, ALD, AH, or ACLF, are accompanied by, and can be identified by increased blood bilirubin levels, increased prothrombin time, and/or reduced serum albumin levels, which can be tested by well-known clinical assays. As such, "treatment" of liver injury, liver damage, liver inflammation, liver failure, cirrhosis, ALD, AH, or ACLF, may result in decreased blood bilirubin levels, decreased prothrombin time, or increased serum albumin. Clinical assay results, such as blood bilirubin levels, decreased prothrombin time, or increased serum albumin can be said to "normalize" when such levels approach or enter a normal or healthy range for a patient.

Provided herein is a method of treating liver disease, liver damage, or liver failure, such as acute liver failure, ALD, AH, or ACLF in a patient that comprises selectively decreasing expression of HNF4A-P2 (fetal) isoform, preferably without significantly decreasing expression of the HNF4A-P1 (mature) isoform in a patient, e.g., in a patient's liver. To selectively decrease expression of the HNF4A-P2 isoform, expression of that isoform may be knocked down or knocked out in some manner. There are a number of ways to decrease expression or activity of a gene in a patient, including, for example, and without limitation: RNA interference, antisense technology, and inhibition of the transcriptional activation activity of HNF4A-P2 isoform through use of, e.g., small molecules or agents that interfere with activity of the HNF4A-P2 isoform, such as decoys, binding reagents, antagonists, etc. However, a goal of the method provided herein is to reduce one specific isoform, and, as such, only that isoform may be targeted. As shown herein, RNA interference (RNAi) is one method by which expression of the HNF4A-P2 isoform can be specifically knocked down without significantly knocking down expression of the HNF4A-P1 isoform. Treatment of a patient results in a decrease in one or more symptoms of liver disease, liver damage, liver failure, such as acute liver failure, ALD, AH, or ACLF in a patient, such as liver damage and liver inflammation. Suitable markers for successful treatment include, without limitation, decreased or normalized blood bilirubin levels, decreased or normalized prothrombin time, or increased or normalized serum albumin in a patient with liver damage, liver failure, liver inflammation, liver disease, cirrhosis, ALD, AH, or ACLF.

The compositions described herein can be administered by any effective route, such as parenteral, e.g., intravenous, intramuscular, subcutaneous, intradermal, etc., formulations of which are described below and in the below-referenced publications, as well as are broadly-known to those of ordinary skill in the art.

Suitable dosage forms may include single-dose, or multiple-dose vials or other containers, such as medical syringes, containing a composition comprising an active ingredient useful for treatment of liver disease, liver damage, liver failure, such as acute liver failure, ALD, AH, or ACLF, as described herein.

Drug products, or pharmaceutical compositions comprising an active agent (e.g., drug), for example, an active agent that decreases HNF4A-P2 isoform activity, may be prepared by any method known in the art of pharmacy, for example, by bringing into association the active ingredient with the carrier(s) or excipient(s). As used herein, a "pharmaceutically acceptable excipient", "carrier" or "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable excipients include one or more of water, saline, phosphate buffered saline, dextrose, glycerol, ethanol, and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active agent. The active agent may be prepared with a carrier that will protect the compound against rapid release, such as a controlled release formulation, including implants, transdermal patches, and microencapsulated delivery systems. Biodegradable, biocompatible polymers can be used in delivery systems, such as ethylene vinyl acetate, polyanhydrides, polyglycolic acid, collagen, polyorthoesters, and polylactic acid. Methods for the preparation of such formulations are broadly-known to those skilled in the art.

Additionally, active agent-containing compositions may be in a variety of forms. The preferred form depends on the intended mode of administration and therapeutic application, which will in turn dictate the types of carriers/excipients. Suitable forms include, but are not limited to, liquid, semi-solid and solid dosage forms.

Pharmaceutical formulations adapted for oral administration may be presented, for example and without limitation, as discrete units such as capsules or tablets; powders or granules; solutions or suspensions in aqueous or non-aqueous liquids; edible foams or whips; or oil-in-water liquid emulsions or water-in-oil liquid emulsions. In certain embodiments, the active agent may be contained in a formulation such that it is suitable for oral administration, for example, by combining the active agent with an inert diluent or an assimilable edible carrier. The active agent (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical formulations adapted for transdermal administration may be presented, for example and without limitation, as discrete patches intended to remain in intimate contact with the epidermis of the recipient for a prolonged period of time or electrodes for iontophoretic delivery.

Pharmaceutical formulations adapted for topical administration may be formulated, for example and without limitation, as ointments, creams, suspensions, lotions, powders, solutions, pastes, gels, sprays, aerosols, or oils. Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents, and other suitable additives. Pharmaceutically acceptable organic or inorganic excipients suitable for non-parenteral administration which do not deleteriously react with nucleic acids can be used.

Pharmaceutical formulations adapted for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include, without limitation, fine particle dusts or mists which may be generated by means of various types of metered dose pressurized aerosols, nebulizers, or insufflators. In the context of delivery of the active agents described herein by inhalation, inhalation drug products, such as metered-dose inhalers, as are broadly-known in the pharmaceutical arts, are used. Metered dose inhalers are configured to deliver a single dose of an active agent per actuation, though multiple actuations may be needed to effectively treat a given patient.

Pharmaceutical formulations adapted for parenteral administration include aqueous and non-aqueous sterile injection solutions which may contain, for example and without limitation, anti-oxidants, buffers, bacteriostats, lipids, liposomes, emulsifiers, also suspending agents and rheology modifiers. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets.

Therapeutic compositions typically must be sterile and stable under the conditions of manufacture and storage. For example, sterile injectable solutions may be prepared by incorporating the active agent in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A "therapeutically effective amount" refers to an amount of a drug product or active agent effective, at dosages and for periods of time necessary, to achieve the desired therapeutic result. An "amount effective" for treatment of a condition is an amount of an active agent or dosage form, such as a single or multiple metered doses from a metered-dose inhaler, effective to achieve a determinable end-point. The "amount effective" is preferably safe—at least to the extent the benefits of treatment outweighs the detriments and/or the detriments are acceptable to one of ordinary skill and/or to an appropriate regulatory agency, such as the U.S. Food and Drug Administration. A therapeutically effective amount of an active agent may vary according to factors such as the disease state, age, sex, and weight of the individual, and the ability of the active agent to elicit a desired response in the individual. A therapeutically effective amount is also one in which any toxic or detrimental effects of the active agent are outweighed by the therapeutically beneficial effects. A "prophylactically effective amount" refers to an amount effective, at dosages and for periods of time necessary, to achieve a desired prophylactic result. Typically, since a prophylactic dose is used in subjects prior to or at an earlier stage of disease, the prophylactically effective amount may be less than the therapeutically effective amount.

Dosage regimens may be adjusted to provide the optimum desired response (e.g., a therapeutic or prophylactic response). For example, a single bolus may be administered, several divided doses may be administered over time, or the composition may be administered continuously or in a pulsed fashion with doses or partial doses being administered at regular intervals, for example, every 10, 15, 20, 30, 45, 60, 90, or 120 minutes, every 2 through 12 hours daily, or every other day, etc. The dosage may be proportionally reduced or increased as indicated by the exigencies of the therapeutic situation. In some instances, it may be especially advantageous to formulate parenteral or inhaled compositions in dosage unit form for ease of administration and uniformity of dosage. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

By "target-specific" or reference to the ability of one compound to bind another target compound specifically, it is meant that the compound binds to the target compound to the exclusion of others in a given reaction system, e.g., in vitro, or in vivo, to acceptable tolerances, permitting a sufficiently specific diagnostic or therapeutic effect according to the standards of a person of skill in the art, a medical community, and/or a regulatory authority, such as the U.S. Food and Drug Agency (FDA). The active agent described herein may be target specific in the context of targeting HNF4A-P2 isoform, down-regulating HNF4A-P2 isoform activity, and effectively treating liver disease, liver damage, or liver failure, such as acute liver failure, ALD, AH, or ACLF, as described herein.

A "gene" is a sequence of DNA or RNA which codes for a molecule, such as a protein or a functional RNA that has a function. Nucleic acids are biopolymers, or small biomolecules, essential to all known forms of life. They are composed of nucleotides, which are monomers made of three components: a 5-carbon sugar, a phosphate group and a nitrogenous base. If the sugar is a simple ribose, the polymer is RNA; if the sugar is derived from ribose as deoxyribose, the polymer is DNA. DNA uses the nitrogenous bases guanine, thymine, adenine, and cytosine. RNA uses the nitrogenous bases guanine, uracil, adenine, and cytosine.

Complementary refers to the ability of polynucleotides (nucleic acids) to hybridize to one another, forming interstrand base pairs. Base pairs are formed by hydrogen bonding between nucleotide units in antiparallel polynucleotide strands. Complementary polynucleotide strands can base pair (hybridize) in the Watson-Crick manner (e.g., A to T, A to U, C to G), or in any other manner that allows for the formation of duplexes. When using RNA as opposed to DNA, uracil rather than thymine is the base that is considered to be complementary to adenosine. Two sequences comprising complementary sequences can hybridize if they form duplexes under specified conditions, such as in water, saline (e.g., normal saline, or 0.9% w/v saline) or phosphate-buffered saline), or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be fully complementary, or have 100% sequence identity (gaps are not counted and the measurement is in relation to the shorter of the two sequences). In one example, a sequence that "specifically hybridizes" to another sequence, does so in a hybridization solution containing 0.5M sodium phosphate buffer, pH 7.2, containing 7% SDS, 1 mM EDTA, and 100 mg/ml of salmon sperm DNA at 65° C. for 16 hours and washing twice at 65° C. for twenty minutes in a washing solution containing 0.5×SSC and 0.1% SDS, or does so under conditions more stringent than 2×SSC at 65° C., for example, in 0.2×SSC at 55° C. A sequence that specifically hybridizes to another typically has at least 80%, 85%, 90%, 95%, OR 99% sequence identity with the other sequence.

"Expression" of a gene refers to the conversion of a DNA sequence of a gene, e.g., the HNF4A gene, to an active, mature gene product such as a polypeptide/protein, or a functional nucleic acid, and includes, for example, transcription, post-transcriptional modification (e.g., splicing) translation, and post-translational processing and/or modification of a protein. Expression of a gene can be reduced by any effective mechanism at any stage of the gene expression process, such as by affecting transcriptional activation, transcription, post-transcriptional RNA processing, translation, and post-translational processing or modification. Expression of an mRNA, such as the HNF4α-P2 isoform mRNA, described herein refers to, without limitation, any aspect of transcription of, splicing of, translation of, and post-translational processing, stability, and activity of the protein product of the mRNA, e.g., the protein product of the HNF4α-P2 isoform mRNA of the HFN4A gene. Activity of a gene product may be decreased not only by decreasing expression of the active protein product, but by affecting the mature protein product, such as by blocking, decoying, or otherwise interfering with the binding of the active product, or a complex containing the active product, to prevent its activity.

Transcription is the process by which the DNA gene sequence is transcribed into pre-mRNA (messenger RNA). The steps include: RNA polymerase, together with one or more general transcription factors, binds to promoter DNA. Transcription factors (TFs) are proteins that control the rate of transcription of genetic information from DNA to messenger RNA, by binding to a specific DNA sequence (i.e., the promoter region). The function of TFs is to regulate genes in order to make sure that they are expressed in the right cell at the right time and in the right amount throughout the life of the cell and the organism. The promoter region of a gene is a region of DNA that initiates transcription of that particular gene. Promoters are located near the transcription start sites of genes, on the same strand, and often, but not exclusively, are upstream (towards the 5' region of the sense strand) on the DNA. Promoters can be about 100-1000 base pairs long. Additional sequences and non-coding elements can affect transcription rates. If the cell has a nucleus (eukaryotes), the RNA is further processed. This includes polyadenylation, capping, and splicing. Polyadenylation is the addition of a poly(A) tail to a messenger RNA. Capping refers to the process wherein the 5' end of the pre-mRNA has a specially altered nucleotide. During RNA splicing, pre-mRNA is edited. Specifically, during this process introns are removed and exons are joined together. The resultant product is known as mature mRNA. The RNA may remain in the nucleus or exit to the cytoplasm through the nuclear pore complex.

RNA levels in a cell, e.g., mRNA levels, can be controlled post-transcriptionally. Native mechanisms, including: endogenous gene silencing mechanisms, interference with translational mechanisms, interference with RNA splicing mechanisms, and destruction of duplexed RNA by RNAse H, or RNAse H-like, activity. As is broadly-recognized by those of ordinary skill in the art, these endogenous mechanisms can be exploited to decrease or silence mRNA activity in a cell or organism in a sequence-specific, targeted manner. Antisense technology typically involves administration of a single-stranded antisense oligonucleotide (ASO) that is chemically-modified, e.g., as described herein, for stability, and is administered in sufficient amounts to effectively penetrate the cell and bind in sufficient quantities to target mRNAs in cells. RNA interference (RNAi) harnesses an endogenous and catalytic gene silencing mechanism, which means that once, e.g., a microRNA, or double-stranded siRNA has been delivered, they are efficiently recognized and stably incorporated into the RNA-induced silencing complex (RiSC) to achieve prolonged gene silencing. Both antisense technologies and RNAi have their strengths and weaknesses, either may be used effectively to decrease or silence expression of a gene or gene product, such as HNF4A-P2 isoform (see, e.g., Watts, J. K., et al. Gene silencing by siRNAs and antisense oligonucleotides in the laboratory and the clinic (2012) 226(2):365-379).

As used herein, "agent" or "RNAi agent", when used in the context of an antisense, RNAi, or ribozyme, or other single-stranded or double-stranded RNA interfering nucleic acids, refers not only to RNA structures, but effective nucleic acid analog structures. In antisense and RNAi technologies, use of RNA poses significant delivery issues due to the lability of RNA molecules. As such, RNA is commonly chemically-modified to produce nucleic acid analogs, not only to enhance stability of the nucleic acid molecules, but often resulting in increased binding affinity, and with reduced toxicity. Such modifications are broadly-known to those of ordinary skill in the art, and are available commercially (see, e.g., Corey, D. R., Chemical modification: the key to clinical application of RNA interference? (2007) *J Clin Invest.* 117(12):3615-3622, also describing RNAi, and United States Patent Application Publication No. 2017/0081667). Non-limiting examples of modifications to the nucleic acid structure in nucleic acid analogs include: modifications to the phosphate linkage, such as phosphoramidates or phosphorothioates; sugar modification, such as 2'-O, 4'-C methylene bridged, locked nucleic acid (LNA), 2'-methoxy, 2'-O-methoxyethyl (MOE), 2'-fluoro, S-constrained-ethyl (cEt), and tricyclo-DNA (tc-DNA); and non-ribose structures, such as phosphorodiamidate morpholino (PMO) and peptide-nucleic acids (PNA).

In addition to those HNF4A-P2 isoform-active RNAi agents described herein, antisense reagents (ASOs), other RNAi agents, ribozyme reagents, and other nucleic acid-based methods of reducing gene expression, may be designed and tested, based on known sequences of HNF4A P2 and P1 isoform RNAs and gene structure (exemplary sequences are provided herein, and the HNF4A gene is well-studied). Based on the present disclosure, one of ordinary skill can design, and/or produce an active agent capable of knocking down HNF4A-P2 isoform expression. Of note, a number of publications describe algorithms for generating candidate iRNA sequences, and publically-available software can be used to implement those algorithms. As such, typically, one only needs to enter a mRNA sequence into a calculator to produce candidate iRNAs. In the present case, because the HNF4A-P2 isoform target shares significant sequence identity with the HNF4A-P1 isoform, those methods and software platforms could not be used to generate candidate sequences. As described herein, HNF4A is transcribed from two different promotors, one expressed in the fetus, and one in adults. As such, the HNF4A P1 and P2 transcripts comprise different 5' ends, with different 5' UTRs (untranslated regions) and different 5' sequences in their ORF (open-reading frame) upstream from the first splice site. The full sequence of the HNF4A-P2 isoform could not be used to generate an iRNA candidate within the 5' sequences unique to the P2 isoform. Also, the sequences specific to the P2 isoform could not be used by themselves to generate an effective iRNA sequence. Only when the sequences specific to the P2 isoform were combined with partial sequences of the sequences common to both the P1 and P2 isoform, could a candidate iRNA sequence be determined—hybridizing to the unique P2 sequence. Exemplary sequences of iRNA specific to the HNF4A-P2 isoform are provided below.

By "reducing activity" of a gene or gene product, e.g., an HNF4α-P2 isoform mRNA, it is meant, by any method of specifically decreasing, suppressing, or silencing expression of the gene, decreasing activity of the gene product, and/or reducing available levels of the gene product in the patient. Activity of an HNF4α-P2 isoform mRNA can be reduced, e.g., by use of antisense nucleic acids, or by use of RNAi agents. Activity of an HNF4α-P2 isoform mRNA also can be reduced by antagonism, or otherwise blocking or interfering with the activity of an HNF4α-P2 isoform mRNA, or by mutation. Available levels of the gene product may be reduced in a patient, for example, either systemically, or locally in the liver, by binding of the an HNF4α-P2 isoform mRNA with an HNF4α-P2 isoform mRNA-binding reagent, such as an antibody, and antibody fragment, or an anti-HNF4α-P2 isoform mRNA paratope-containing polypeptide compositions, or a nucleic acid decoy comprising an HNF4α-P2 isoform mRNA nucleotide binding sequence motif acting to competitively bind an HNF4α-P2 isoform mRNA.

By decreasing, down-regulating, or knocking down an HNF4α-P2 isoform mRNA expression or activity, it is meant any action that results in lower activity of an HNF4α-P2 isoform mRNA in a cell or patient—typically by use of a therapeutic agent. Useful therapeutic agents include, without limitation, antisense or RNAi agents; binding reagents, such as antibodies (including antibody fragments or antibody-based polypeptide ligands), and aptamers; antagonists; decoys; and peptide-based therapies.

The terms "HNF4α" and "hepatocyte nuclear factor 4 alpha" refer to a nuclear transcription factor which binds DNA as a homodimer. The encoded protein controls the expression of several genes, including hepatocyte nuclear factor 1 alpha, a transcription factor which regulates the expression of several hepatic genes. This gene may play a role in development of the liver, kidney, and intestines. Mutations in this gene have been associated with monogenic autosomal dominant non-insulin-dependent diabetes mellitus type I. Alternative splicing of this gene results in multiple transcript variants encoding several different isoforms, including the P2 isoforms, and having an amino acid sequence from any vertebrate or mammalian source, including, but not limited to, human, bovine, chicken, rodent, mouse, rat, porcine, ovine, primate, monkey, and guinea pig, unless specified otherwise. The term also refers to fragments and variants of native HNF4α that maintain at least one in vivo or in vitro activity of a native HNF4α. The term encompasses full-length unprocessed precursor forms of HNF4α as well as mature forms resulting from, e.g., post-translational processing.

The sequence of an exemplary human HNF4α mRNA transcript corresponding to an HNF4α-P2 isoform is provided herein as SEQ ID NO: 1. The "target sequence" within that HNF4α-P2 isoform mRNA sequence refers to a contiguous portion of the nucleotide sequence of human HNF4α mRNA molecule formed during the transcription of an HNF4α gene that is present in HNF4α-P2 isoform mRNA, but not in HNF4α-P1 isoform mRNA, and therefore includes at least a portion of the sequence of exon 1D, including the 5' UTR and 5' portion of the ORF, for example and without limitation, extending from, or including contiguous sequences of from about 15-30 bases of bases 1-53 of SEQ ID NO: 1 (underlined in FIG. 4) and having the sequence: 5'-GGCCATGGTC AGCGTGAACG CGCCCCTCGG GGCTCCAGTG GAGAGTTCTT ACG-3' (SEQ ID NO: 1, bases 1-58). This sequence is an exemplary human sequence, and is taken from Genbank Accession No. NM_175914.4 (Homo sapiens hepatocyte nuclear factor 4 alpha (HNF4A), transcript variant 5, mRNA, FIG. 4). Additional exemplary HNF4α-P2 isoforms initiating from the P2 promoter include HNF4 alpha7 (NM_001030003.2, FIG. 5) and HNF4 alpha9 (NM_001030004.2, FIG. 6). The target portion of the sequence may be at least long enough to serve as a substrate for iRNA-directed cleavage at or near that portion of the nucleotide sequence of an mRNA molecule formed during the transcription of an HNF4α gene, e.g., from the HNF4α-P2 isoform promoter. The target sequence may extend up to 1, 2, 3, 4, 5, 6, 7, 8, 9, or 10 bases 3' to exon 1D, e.g., is a contiguous sequence of at least about 15 bases within GGCCATGGTCAGCGT-GAACGCGCCCCTCGGGGCTCCAGTGGAGAGTTCT-TAC GACACGTCCCC (SEQ ID NO: 1, bases 1-63). The target sequence may be 15 or more contiguous bases of GCTCCAGTGGAGAGTTCTTACGACACG (SEQ ID NO: 1, bases 32-58), such as GCTCCAGTGGAGAGTTCTT (SEQ ID NO: 1, bases 32-50), CTCCAGTG-GAGAGTTCTTA (SEQ ID NO: 1, bases 33-51), TCCAGTGGAGAGTTCTTAC (SEQ ID NO: 1, bases 34-52), or GGAGAGTTCTTACGACAC (SEQ ID NO: 1, bases 40-57). All nucleotide sequences are shown in a 5' to 3' direction unless indicated to the contrary. FIGS. 7A and 7B provide exemplary additional oligomers useful as RNAi agents for inhibition of HNF4α-P2 isoforms based on GenBank accession No. NM_175914.4. The target sequence may be present in HNF4α-P2 isoforms and not in HNF4α-P1 isoforms, and thus can selectively decrease or knock down HNF4α-P2 isoform mRNAs and not HNF4α-P1 isoform mRNAs, at least not to any significant extent in the context of the methods described herein.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated.

As used herein, the term "strand comprising a sequence" refers to an oligonucleotide comprising a chain of nucleotides that is described by the sequence referred to using the standard nucleotide nomenclature. "G," "C," "A," "T," and "U" each generally stand for a nucleotide that contains guanine, cytosine, adenine, thymidine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil can be replaced by other moieties without substantially altering, or improving in the context of RNA interference, the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods described herein.

The terms "iRNA," "RNAi agent," and "RNA interference agent" as used interchangeably herein, refer to an agent that contains RNA or modified RNA that mediates the targeted cleavage of an RNA transcript via an RNA-induced silencing complex (RISC) pathway. RNAi agents direct the sequence-specific degradation of mRNA through a process known as RNA interference (RNAi). The iRNA modulates, e.g., inhibits or knocks down, the expression of HNF4α-P2 isoform mRNA in a cell, e.g., a cell within a subject, such as a mammalian subject.

An RNAi agent may be a single stranded RNA or modified RNA that interacts with a target RNA sequence, e.g., an HNF4α-P2 isoform target mRNA sequence, to direct the cleavage of the target RNA. Without wishing to be bound by theory it is believed that long double stranded RNA introduced into cells is broken down into double stranded short interfering RNAs (siRNAs) comprising a sense strand and an antisense strand by a Type III endonuclease known as Dicer. Dicer, a ribonuclease-III-like enzyme, processes these dsRNA into 19-23 base pair short interfering RNAs with characteristic two base 3' overhangs. These siRNAs are then incorporated into an RNA-induced silencing complex (RISC) where one or more helicases unwind the siRNA duplex, enabling the complementary antisense strand to guide target recognition. Upon binding to the appropriate target mRNA, one or more endonucleases within the RISC cleave the target to induce silencing. Thus, in one aspect, the invention relates to a single stranded RNA (ssRNA) (the antisense strand of an siRNA duplex) generated within a cell and which promotes the formation of a RISC complex to effect silencing of the target gene. Accordingly, the term "siRNA" is also used herein to refer to an interfering RNA (iRNA).

The RNAi agent may be a single-stranded RNA or modified RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348 and in Lima et al., (2012) Cell 150:883-894. Any of the RNAi agents described herein may be used as a single-stranded siRNA as described herein or as chemically modified by the methods described in Lima et al., (2012) Cell 150:883-894.

An "iRNA" or RNAi agent" for use in the compositions and methods described herein may be a double stranded RNA and can be referred to herein as a "double stranded RNAi agent," "double stranded RNA (dsRNA) molecule," "dsRNA agent," or "dsRNA". The term "dsRNA", refers to a complex of ribonucleic acid molecules or modified RNAs, having a duplex structure comprising two anti-parallel and substantially complementary nucleic acid strands, referred to as having "sense" and "antisense" orientations with respect to a target RNA, e.g., an HNF4α-P2 isoform mRNA.

The majority of nucleotides of each strand of an RNA agent may be ribonucleotides, but each or both strands may include one or more non-ribonucleotides, e.g., a deoxyribonucleotide and/or a modified nucleotide. In addition, an RNAi agent may include ribonucleotides with chemical modifications at one or more nucleotides. As used herein, the term "modified nucleotide" refers to a nucleotide having, independently, a modified sugar moiety, a modified internucleotide linkage, and/or a modified nucleobase. Thus, the term "modified nucleotide" encompasses substitutions, additions or removal of, e.g., a functional group or atom, to inter-nucleoside linkages, sugar moieties, or nucleobases. The modifications suitable for use in the reagents described herein include any type of modification resulting in a functional RNAi agent, ASO, or other functional oligonucleotide. Any such modifications, as used in an siRNA-type molecule, are encompassed by "RNAi agent" for the purposes of this disclosure. International Patent Application Publication No. WO 2016/209862 is incorporated herein by reference in its entirety for the disclosure of various exemplary RNAi agent compositions and modifications thereof, and delivery methods and compositions for RNAi agents, useful in the implementation of the present invention.

In an RNAi agent, the duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. The hairpin loop may comprise at least 2, at least 3, at least 4, at least 5, at least 6, at least 7, at least 8, at least 9, at least 10, at least 20, at least 23, or more unpaired nucleotides. The hairpin loop may be 10 or fewer nucleotides, 8 or fewer unpaired nucleotides, from 4-10 unpaired nucleotides, or from 4-8 nucleotides.

Where the two substantially complementary strands of a dsRNA are comprised by separate RNA molecules, those molecules need not be, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

An RNAi agent may be a dsRNA, each strand of which comprises 19-23 nucleotides, that interacts with a target RNA sequence, e.g., an HNF4α-P2 isoform mRNA. Without wishing to be bound by theory, long double stranded RNA introduced into cells is broken down into siRNA by a Type III endonuclease known as Dicer. Dicer, a ribonuclease-III-like enzyme, processes the dsRNA into 19-23 base pair short interfering RNAs with characteristic two base 3' overhangs.

The siRNAs are then incorporated into an RNA-induced silencing complex (RISC) where one or more helicases unwind the siRNA duplex, enabling the complementary antisense strand to guide target recognition. Upon binding to the appropriate target mRNA, one or more endonucleases within the RISC cleave the target to induce silencing. An RNAi agent may be a dsRNA of 24-30 nucleotides that interacts with a target RNA sequence to direct the cleavage of the target RNA. A dsRNA may comprise an overhang of at least one nucleotide; alternatively the overhang can comprise at least two nucleotides, at least three nucleotides, at least four nucleotides, at least five nucleotides, or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA. Alternatively, both ends of a dsRNA may be blunt at both ends (blunt-ended), with no nucleotide overhang at either end of the molecule. Most often such a molecule will be double stranded over its entire length.

The term "antisense strand" or "guide strand" refers to the strand of an iRNA, e.g., a dsRNA, which includes a region that is substantially complementary to a target sequence, e.g., an HNF4α-P2 isoform mRNA. As used herein, the term "region of complementarity" refers to the region on the antisense strand that is substantially complementary to a sequence, for example, a target sequence, e.g., an HNF4α-P2 isoform mRNA sequence, as described herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA. The term "sense strand" or "passenger strand" as used herein, refers to the strand of an iRNA that includes a region that is substantially complementary to a region of the antisense strand as that term is defined herein.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing. The terms "complementary," "fully complementary" and "substantially complementary" herein can be used with respect to the base matching between the sense strand and the antisense strand of a dsRNA, or between the antisense strand of an RNAi agent and a target sequence, as will be understood from the context of their use.

As used herein, a polynucleotide that is "substantially complementary to at least part of a messenger RNA (mRNA) refers to a polynucleotide that is substantially complementary to a contiguous portion of the mRNA of interest (e.g., an HNF4α-P2 isoform mRNA). For example, a polynucleotide is complementary to at least a part of an HNF4α-P2 isoform mRNA that is not preset in HNF4α-P1 isoform mRNA if the sequence is substantially complementary to a non-interrupted portion of an HNF4α-P2 isoform mRNA, e.g., bases 1-63 of SEQ ID NO: 1.

The antisense strand polynucleotides disclosed herein may be fully complementary to the target HNF4α-P2 isoform mRNA sequence. The antisense strand polynucleotides disclosed herein may be substantially complementary to the target HNF4α-P2 isoform mRNA sequence and comprise a contiguous nucleotide sequence which is at least about 80% complementary over its entire length to the equivalent region of bases 1-53 or bases 1-63 of the nucleotide sequence of SEQ ID NO: 1, or a fragment thereof, such as about 85%, about 86%, about 87%, about 88%, about 89%, about 90%, about 91%, about 92%, about 93%, about 94%, about 95%, about 96%, about 97%, about 98%, or about 99% complementary.

The antisense polynucleotides disclosed herein may substantially complementary to the target HNF4α-P2 isoform mRNA sequence and comprise a contiguous nucleotide sequence which is at least about 80% complementary over its entire length to any one of the sense strand nucleotide sequences above or in FIG. 7A, or a fragment of any one of the sense strand nucleotide sequences above or in FIG. 7A, such as at least 85%, 90%, 95% complementary, or 100% complementary.

An RNAi agent may include a sense strand that is substantially complementary to an antisense polynucleotide which, in turn, is substantially or fully complementary to a target HNF4α-P2 isoform mRNA sequence, and wherein the sense strand polynucleotide comprises a contiguous nucleotide sequence which is at least about 80% complementary over its entire length to the equivalent region of a sense nucleotide sequence provided above or in FIG. 7A, or a fragment of a sense nucleotide sequence provided above or in FIG. 7A or 7B, such as about 85%, about 86%, about 87%, about 88%, about 89%, about 90%, about 91%, about 92%, about 93%, about 94%, about 95%, about 96%, about 97%, about 98%, or about 99% complementary.

The term "inhibiting," as used herein, is used interchangeably with "reducing," "silencing," "downregulating," "suppressing", "knocking down", and other similar terms, and includes any level of inhibition. The phrase "inhibiting expression of an HNF4α-P2 isoform mRNA," as used herein, includes inhibition of expression of any HNF4α gene (such as, e.g., a mouse HNF4α gene, a rat HNF4α gene, a monkey HNF4α gene, or a human HNF4α gene) as well as variants or mutants of an HNF4α gene that encode an HNF4α protein, in its production of HNF4α-P2 isoform mRNA, affecting the stability of HNF4α-P2 isoform mRNA, such as by antisense or RNAi technologies, or inhibiting translation of HNF4α-P2 isoform mRNA. By "inhibiting expression of an HNF4α-P2 isoform mRNA", expression of, stability of, translation of, or activity of HNF4α-P1 isoform mRNA and/or the HNF4α-P1 isoform protein product is not affected to an clinically-relevant or clinically-significant level.

"Inhibiting expression of an HNF4α-P2 isoform mRNA" includes any level of inhibition of an HNF4α-P2 isoform mRNA, e.g., at least partial suppression of the expression of an HNF4α-P2 isoform mRNA, such as an inhibition by at least about 20%. Inhibition may be by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of an HNF4α-P2 isoform mRNA may be assessed based on the level of any variable associated with HNF4α-P2 isoform mRNA expression, e.g., HNF4α-P2 isoform mRNA level or HNF4α-P2 isoform protein level. The expression of an HNF4α-P2 isoform mRNA may also be assessed indirectly based on, e.g., expression of genes and gene products controlled by the HNF4α P1 or P2 gene product(s), or by assay of physiological markers associated with over-expression of the HNF4α-P2 isoform mRNA, or normal activity of the HNF4α-P1 isoform mRNA in a patient.

At least partial suppression of the expression of an HNF4α-P2 isoform mRNA, may be assessed by a reduction of the amount of HNF4α-P2 isoform mRNA which can be isolated from or detected in a first cell or group of cells, e.g., liver cells or tissue, in which an HNF4α gene is transcribed and which has or have been treated such that the expression of an HNF4α-P2 isoform mRNA is inhibited, as compared to a second cell or group of cells substantially identical to the first cell or group of cells but which has or have not been so treated (control cells). The degree of inhibition may be expressed in terms of:

$$\frac{(mRNA \text{ in control cells}) \cdot (mRNA \text{ in treated cells})}{(mRNA \text{ in control cells})} \cdot 100\%.$$

The phrase "contacting a cell with an RNAi agent," such as a dsRNA, as used herein, includes contacting a cell by any possible means. Contacting a cell with an RNAi agent includes contacting a cell in vitro with the RNAi agent, or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

Contacting a cell with an RNAi agent may include "introducing" or "delivering" the RNAi agent into the cell by facilitating or effecting uptake or absorption into the cell. Absorption or uptake of an RNAi agent can occur through unaided diffusive or active cellular processes, or by auxiliary agents or devices. Introducing an RNAi agent into a cell may be in vitro and/or in vivo. For example, for in vivo introduction, RNAi agent can be injected into a tissue site or administered systemically. In vivo delivery can also be done by a beta-glucan delivery system, such as those described in U.S. Pat. Nos. 5,032,401 and 5,607,677, and U.S. Patent Application Publication No. 2005/0281781, the technical disclosure of which are hereby incorporated herein by reference. In vitro introduction into a cell includes methods known in the art such as electroporation and lipofection. Further approaches are described herein below and/or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858,225, 6,815,432, 8,158,601, and 8,058,069, the technical disclosure of which are hereby incorporated herein by reference.

As above, a "patient" or "subject" is an animal, such as a mammal, including a primate (such as a human, a non-human primate, e.g., a monkey and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). It is understood that the sequence of the HNF4α-P2 isoform mRNA must be sufficiently complementary to the antisense strand of the RNAi agent for the agent to be used in the indicated species.

The patient may be a human, such as a human being treated or assessed for a disease, disorder or condition that would benefit from reduction in HNF4α-P2 isoform mRNA expression; a human at risk for a disease, disorder or condition that would benefit from reduction in HNF4α-P2 isoform mRNA expression; a human having a disease, disorder or condition that would benefit from reduction in HNF4α-P2 isoform mRNA expression; and/or human being treated for a disease, disorder or condition that would benefit from reduction in HNF4α-P2 isoform mRNA expression as described herein.

By "lower" in the context of a disease marker or symptom is meant a clinically-relevant and/or a statistically significant decrease in such level. The decrease can be, for example, at least 10%, at least 20%, at least 30%, at least 40%, or more, down to a level accepted as within the range of normal for an individual without such disorder, or to below the level of detection of the assay. The decrease may be down to a level accepted as within the range of normal for an individual without such disorder which can also be referred to as a normalization of a level. For example, lowering bilirubin to within a range of from 0.3-1 mg/dL (5.1-17 micromol/L) would be considered to be within the range of normal for a subject. The reduction may be the normalization of the level of a sign or symptom of a disease, a reduction in the difference between the subject level of a sign of the disease and the normal level of the sign for the disease (e.g., to the upper level of normal when the value for the subject must be decreased to reach a normal value, and to the lower level of normal when the value for the subject must be increased to reach a normal level). The methods may include a clinically relevant inhibition of expression of an HNF4α-P2 isoform mRNA, e.g., as demonstrated by a clinically relevant outcome after treatment of a subject with an agent to reduce the expression of an HNF4α-P2 isoform mRNA.

As used herein, "prevention" or "preventing," when used in reference to a disease, disorder or condition thereof, that would benefit from a reduction in expression of an HNF4α-P2 isoform mRNA, refers to a reduction in the likelihood that a subject will develop a symptom associated with such disease, disorder, or condition, e.g., liver disease, liver damage, liver inflammation, or liver failure, such as acute liver failure, ALD, AH, or ACLF. The likelihood of developing liver disease, liver damage, liver inflammation, or liver failure, such as acute liver failure, ALD, AH, or ACLF is reduced, for example, when an individual having one or more risk factors for liver disease, liver damage, liver inflammation, or liver failure, such as acute liver failure, ALD, AH, or ACLF, e.g., a genetic disorder, either fails to develop liver disease, liver damage, liver inflammation, or liver failure, such as acute liver failure, ALD, AH, or ACLF, or signs or symptoms thereof, or develops liver disease, liver damage, liver inflammation, or liver failure, such as acute liver failure, ALD, AH, or ACLF, or signs or symptoms thereof, with less severity relative to a population having the same risk factors and not receiving treatment as described herein. The failure to develop a disease, disorder or condition, or the reduction in the development of a symptom associated with such a disease, disorder or condition (e.g., by at least about 10% on a clinically accepted scale for that disease or disorder), or the exhibition of delayed symptoms (e.g., by days, weeks, months, or years) is considered effective prevention. Prevention can require administration of more than one dose of an agent described herein.

As used herein, a "disease or disorder that would benefit from reduction in HNF4α-P2 isoform mRNA levels" may be a disease or disorder associated with liver disease, liver damage, or liver failure. For example, this term includes any disorder, disease or condition resulting in one or more signs or symptoms of acute liver failure, ALD, AH, or ACLF.

"Therapeutically effective amount," as used herein, is intended to include the amount of an RNAi agent that, when administered to a subject having liver disease, liver damage, liver inflammation, or liver failure, such as acute liver failure, ALD, AH, or ACLF, is sufficient to effect treatment of the disease (e.g., by diminishing, ameliorating or maintaining the existing disease or one or more symptoms of disease). The "therapeutically effective amount" may vary depending on the sequence and chemical composition of the RNAi agent, how the agent is administered, the disease and its severity, the patient's history, age, weight, family history, genetic makeup, the types of preceding or concomitant treatments, if any, and other individual characteristics of the subject to be treated.

"Prophylactically effective amount," as used herein, is intended to include the amount of an RNAi agent that, when administered to a subject having liver disease, liver damage, liver inflammation, or liver failure, such as acute liver failure, ALD, AH, or ACLF, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the disease and its severity, the patient's history, age, weight, family history, genetic makeup, the types of preceding or concomitant treatments, if any, and other individual characteristics of the subject to be treated.

A "therapeutically-effective amount" or "prophylactically effective amount" also includes an amount of an RNAi agent that produces some desired local or systemic effect at a reasonable benefit/risk ratio applicable to any treatment. RNAi agents employed in the methods described herein may be administered in a sufficient amount to produce a reasonable benefit/risk ratio applicable to such treatment.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. Samples may be derived from the liver (e.g., whole liver or certain segments of liver or certain types of cells in the liver, such as, e.g., hepatocytes). A "sample derived from a subject" may refer to blood drawn from the subject or plasma isolated therefrom, saliva, or urine, typically a 24 hour urine sample.

Described herein are RNAi agents that inhibit the expression of an HNF4α-P2 isoform mRNA. The RNAi agent may include double stranded ribonucleic acid (dsRNA) molecules for inhibiting the expression of an HNF4α-P2 isoform mRNA in a cell, such as a cell within a subject, e.g., a mammal, such as a human having liver disease, liver damage, liver inflammation, or liver failure, such as acute liver failure, ALD, AH, or ACLF. The dsRNA includes an antisense strand having a region of complementarity which is complementary to at least a part of an mRNA formed in the expression of an HNF4α-P2 isoform mRNA. The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the HNF4α-P2 isoform mRNA, the iRNA inhibits the expression of the HNF4α-P2 isoform mRNA (e.g., a human, a primate, a non-primate, or a bird HNF4α-P2 isoform mRNA) by at least about 10% as assayed by, for example, a PCR-based method, or by a protein-based method, such as by immunofluorescence analysis, using, for example, western blotting, or flowcytometric techniques. Inhibition of expression may determined by the qPCR method provided in the examples. For in vitro assessment of activity, percent inhibition is determined using the methods provided herein at a single dose at, for example, a 10 nM duplex final concentration. For in vivo studies, the level after treatment can be compared to, for example, an appropriate historical control or a pooled population sample control to determine the level of reduction, e.g., when a baseline value is no available for the subject.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an HNF4α-P2 isoform mRNA. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

The dsRNA may be between about 15 and about 23 nucleotides in length, or between about 25 and about 30 nucleotides in length. In general, the dsRNA is long enough to serve as a substrate for the Dicer enzyme. For example, it is well known in the art that dsRNAs longer than about 21-23 nucleotides can serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, to the extent that it becomes processed to a functional duplex, of e.g., 15-30 base pairs, that targets a desired RNA for cleavage, an RNA molecule or complex of RNA molecules having a duplex region greater than 30 base pairs may be a dsRNA. Thus, an ordinarily skilled artisan will recognize that an miRNA is a dsRNA. A dsRNA may not be a naturally occurring miRNA. An RNAi agent useful to target HNF4α-P2 isoform mRNA expression may not be generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end, or both ends of either an antisense or sense strand of a dsRNA. Longer, extended overhangs are possible.

A dsRNA can be synthesized by standard methods known in the art as further discussed below, e.g., by use of an automated DNA synthesizer, such as are commercially available from, for example, Biosearch™, Applied Biosystems™, Inc. iRNA compounds may be prepared using a two-step procedure.

First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides can be prepared using solution-phase or solid-phase organic synthesis or both.

A dsRNA may include at least two nucleotide sequences, a sense sequence and an antisense sequence. The sense strand sequence is selected from the group of sequences provided above or in FIG. 7A, and the corresponding nucleotide sequence of the antisense strand of the sense strand is selected from the group of sequences provided in above or in FIG. 7A. One of the two sequences may be complementary to the other of the two sequences, with one of the sequences being substantially complementary to a sequence of an HNF4α-P2 isoform mRNA. As such, a dsRNA may include two oligonucleotides, where one oligonucleotide is described as the sense strand in above or in FIG. 7A, and the second oligonucleotide is described as the corresponding antisense strand of the sense strand in above or in FIG. 7A. The substantially complementary sequences of the dsRNA may be contained on separate oligonucleotides or on a single oligonucleotide.

It will be understood that, although the sequences in FIG. 7A are described as modified and/or conjugated sequences, the RNA of the iRNA described herein, e.g., a dsRNA, may comprise any one of the sequences set forth in any one of FIG. 7A that is un-modified, un-conjugated, and/or modified and/or conjugated differently than described therein.

A double stranded ribonucleic acid (dsRNA) for inhibiting expression of HNF4α-P2 isoform mRNA may comprise, consist essentially of, or consist of a sense strand and an antisense strand, wherein the sense strand comprises the nucleotide sequence of a sense strand (e.g., as in FIG. 7A) and the antisense strand comprises the nucleotide sequence of the corresponding antisense strand (e.g., as in FIG. 7A).

The skilled person is well aware that dsRNAs having a duplex structure of between about 20 and 23 base pairs, e.g., 21, base pairs have been hailed as particularly effective in inducing RNA interference. However, others have found that shorter or longer RNA duplex structures can also be effective. In the aspects described above, by virtue of the nature of the oligonucleotide sequences provided herein, dsRNAs described herein can include at least one strand of a length of minimally 21 nucleotides. It can be reasonably expected that shorter duplexes minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences provided herein, and differing in their ability to inhibit the expression of an HNF4α-P2 isoform mRNA by not more than about 5, 10, 15, 20, 25, or 30% inhibition from a dsRNA comprising the full sequence, are contemplated to be within the scope of the present disclosure.

In addition, the RNAs described herein identify a site in an HNF4α-P2 isoform mRNA that is susceptible to RISC-mediated cleavage. As such, the present invention further features iRNAs that target within this site. As used herein, an iRNA is said to target within a particular site of an RNA transcript if the RNAi agent promotes selective cleavage of the transcript anywhere within that particular site. Such an RNAi agent will generally include at least about 15 contiguous nucleotides from one of the sequences provided herein coupled to additional nucleotide sequences taken from the region contiguous to the selected sequence in an HNF4α gene.

While a target sequence is generally about 15-30 nucleotides in length, there can be variation in the suitability of particular sequences in this range for directing cleavage of any given target RNA. Various software packages may provide guidance for the identification of optimal target sequences for any given gene target, but an empirical approach may also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an RNAi agent, mediate the best inhibition of target gene expression. Thus, while the sequences identified herein represent effective target sequences, it is contemplated that further optimization of inhibition efficiency can be achieved by progressively "walking the window" one nucleotide upstream or downstream of the given sequences to identify sequences with equal or better inhibition characteristics.

Further, based on the present disclosure, it is contemplated that for any sequence identified herein, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An RNAi agent as described herein can contain one or more mismatches to the target sequence. In one aspect, an RNAi agent as described herein contains no more than 3 mismatches. If the antisense strand of the RNAi agent contains mismatches to a target sequence, it may be preferable that the area of mismatch is not located in the center of the region of complementarity. If the antisense strand of the RNAi agent contains mismatches to the target sequence, it may be preferable that the mismatch be restricted to be within the last 5 nucleotides from either the 5'- or 3'-end of the region of complementarity. For example, for a 23 nucleotide RNAi agent the strand which is complementary to a region of an HNF4α-P2 isoform mRNA, generally does not contain any mismatch within the central 13 nucleotides. The methods described herein or methods known in the art can be used to determine whether an RNAi agent containing a mismatch to a target sequence is effective in inhibiting the expression of an HNF4α-P2 isoform mRNA. Consideration of the efficacy of iRNAs with mismatches in inhibiting expression of an HNF4α-P2 isoform mRNA is important, especially if the particular region of complementarity in an HNF4α-P2 isoform mRNA is known to have polymorphic sequence variation within the population.

The RNA of the RNAi agent described herein, e.g., a dsRNA, may be un-modified, and does not comprise, e.g., chemical modifications and/or conjugations known in the art and described herein. The RNA of an RNAi agent described herein, e.g., a dsRNA, may be chemically modified to enhance stability or other beneficial characteristics. Substantially all of the nucleotides of an RNAi agent may be modified. All of the nucleotides of an RNAi agent may be modified. RNAi agents in which "substantially all of the nucleotides are modified" are largely but not wholly modified and can include not more than 5, 4, 3, 2, or 1 unmodified nucleotides.

The nucleic acids described herein may be synthesized and/or modified by methods well established in the art. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA agents useful in the methods described herein include, but are not limited to RNAs containing modified backbones or no natural internucleoside linkages. RNAs having modified backbones include, among others, those that do not have a phosphorus atom in the backbone. Modified RNAs that do not have a phosphorus atom in their internucleoside backbone are also be considered to be oligonucleosides.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and RE39464, the technical disclosure of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and C component parts.

Suitable RNA mimetics in RNAi agents in which both the sugar and the internucleoside linkage, i.e., the backbone, of the nucleotide units may be replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA), which includes chiral γ-PNAs. In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the technical disclosure of each of which are hereby incorporated herein by reference. Additional PNA compounds suitable for use in the iRNAs are described in, for example, in Nielsen et al., Science, 1991, 254, 1497-1500. Additional nucleic acid modifications are broadly-known.

An iRNA may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C., and are exemplary base substitutions, even more particularly when combined with 2'-O-methoxyethyl sugar modifications.

The RNA of an RNAi agent can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects.

The RNAi agent may comprise one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e., the covalent carbon-oxygen-carbon bond between the C1' and C4' carbons). In another example, the C2'-C3' bond (i.e., the covalent carbon-carbon bond between the C2' and C3' carbons) of the sugar has been removed). Representative U.S. publications that teach the preparation of UNA include, but are not limited to, U.S. Pat. No. 8,314,227; and US Patent Application Publication Nos. 2013/0096289; 2013/0011922; and 2011/0313020, the technical disclosure of each of which are hereby incorporated herein by reference.

An RNAi agent may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering. Representative publications that teach the preparation of certain of the above noted CRN include, but are not limited to, US Patent Application Publication No. 2013/0190383; and PCT Publication No. WO 2013/036868, the technical disclosure of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-0-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of the nucleotides of an iRNA include a 5' phosphate or 5' phosphate mimic, e.g., a 5'-terminal phosphate or phosphate mimic on the antisense strand of an RNAi agent. Suitable phosphate mimics are disclosed in, for example US Patent Application Publication No. 2012/0157511, the technical disclosure of which are incorporated herein by reference.

Another possible modification of an iRNA involves chemically linking to the RNA one or more ligands, moieties or conjugates that enhance the activity, cellular distribution or cellular uptake of the iRNA. Such moieties include but are not limited to lipid moieties such as a cholesterol moiety, cholic acid, a thioether, e.g., beryl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-phosphonate, a polyamine or a polyethylene glycol chain, or adamantane acetic acid, a palmityl moiety, or an octadecylamine or hexylamino-carbonyloxycholesterol moiety.

A ligand may alter the distribution, targeting or lifetime of an RNAi agent into which it is incorporated. A ligand may provide an enhanced affinity for a selected target, e.g., molecule, cell or cell type, compartment, e.g., a cellular or organ compartment, tissue, organ or region of the body, as, e.g., compared to a species absent such a ligand. It may be preferable that ligands will not take part in duplex pairing in a duplexed nucleic acid. Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands may also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, monovalent or multivalent galactose, N-acetyl-galactosamine, N-acetyl-glucosamine multivalent mannose, multivalent fucose, glycosylated polyaminoacids, transferrin, bisphosphonate, polyglutamate, polyaspartate, a lipid, cholesterol, a steroid, bile acid, folate, vitamin B 12, vitamin A, biotin, or an RGD peptide or RGD peptide mimetic. Ligands may include monovalent or multivalent galactose. Ligands may include cholesterol.

Other examples of ligands include dyes, intercalating agents (e.g. acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-0 (hexadecyl)glycerol, geranyloxyhexyl group, hexadecylglycerol, borneol, menthol, 1,3-propanediol, heptadecyl group, palmitic acid, myristic acid, 03-(oleoyl) lithocholic acid, 03-(oleoyl)cholenoic acid, dimethoxytrityl, or phenoxazine), and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands may be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They may also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand may be, for example, a lipopolysaccharide, an activator of p38 MAP kinase, or an activator of NF-KB.

The ligand may be a substance, e.g., a drug, which can increase the uptake of the RNAi agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

A ligand attached to an iRNA may act as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g., as PK modulating ligands). In addition, aptamers that bind serum components (e.g., serum proteins) are also suitable for use as PK modulating ligands.

The ligand may be a cell-permeation agent, such as a helical cell-permeation agent. The agent may be amphipathic. An exemplary agent is a peptide such as that or antennopedia. If the agent is a peptide, it can be modified, including a peptidylmimetic, invertomers, non-peptide or pseudo-peptide linkages, and use of D-amino acids. The helical agent may be an alpha-helical agent, which may have a lipophilic and a lipophobic phase.

The ligand may be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to RNAi agents can affect pharmacokinetic distribution of the RNAi agent, such as by enhancing cellular recognition and absorption.

The peptide or peptidomimetic moiety may be about 5-50 amino acids long, e.g., about 5, 10, 15, 20, 25, 30, 35, 40, 45, or 50 amino acids long.

A peptide or peptidomimetic may be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). RFGF. The peptide moiety can be a "delivery" peptide, which can carry large polar molecules including peptides, oligonucleotides, and protein across cell membranes. For example, sequences from the HIV Tat protein) and the Drosophila Antennapedia protein (have been found to be capable of functioning as delivery peptides. A peptide or peptidomimetic can be encoded by a random sequence of DNA, such as a peptide identified from a phage-display library, or one-bead-one-compound (OBOC) combinatorial library. Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

A "cell permeation peptide" is capable of permeating a cell, e.g., a microbial cell, such as a bacterial or fungal cell, or a mammalian cell, such as a human cell. A microbial cell-permeating peptide can be, for example, a a-helical linear peptide (e.g., LL-37 or Ceropin PI), a disulfide bond-containing peptide (e.g., a-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen.

Ligand-conjugated oligonucleotides may be synthesized by the use of an oligonucleotide that bears a pendant reactive functionality, such as that derived from the attachment of a linking molecule onto the oligonucleotide. This reactive oligonucleotide may be reacted directly with commercially-available ligands, ligands that are synthesized bearing any of a variety of protecting groups, or ligands that have a linking moiety attached thereto.

The RNAi agents may be conveniently and routinely made through the well-known technique of solid-phase synthesis. Equipment for such synthesis is sold by several vendors including, for example, Applied Biosystems™ (Foster City, Calif.). Any other means for such synthesis known in the art may additionally or alternatively be employed. It is also known to use similar techniques to prepare other oligonucleotides, such as the phosphorothioates and alkylated derivatives. In ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks. When using nucleotide-conjugate precursors that already bear a linking moiety, the synthesis of an oligonucleotide comprising a linker may be first completed, and the ligand molecule may then be reacted with the linking moiety to form the ligand-conjugated oligonucleotide. Oligonucleotides or linked nucleosides may be synthesized by an automated synthesizer using phosphoramidites derived from ligand-nucleoside conjugates in addition to the standard phosphoramidites and non-standard phosphoramidites that are commercially available and routinely used in oligonucleotide synthesis.

An iRNA agent may further comprises a carbohydrate. Carbohydrate-conjugated RNAi agent are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen, or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen, or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8). A carbohydrate conjugate may be or may comprise a monosaccharide.

One or more GalNAc (N-Acetylgalactosamine) or GalNAc derivative moieties may be attached to an RNAi agent by a linker, such as a monovalent, bivalent, or trivalent linker. An example of a GalNAc-containing moiety is L96 (N-[tris(GalNAc-alkyl)-amidodecanoyl)]-4-hydroxyprolinol (Hyp-(GalNAc-alkyl)$_3$). Additional carbohydrate conjugates (and linkers) suitable for use include those described in PCT Publication Nos. WO 2014/179620, WO 2014/179627, and WO 2016/209862, each of which is incorporated herein by reference. An RNAi agent may comprise an oligonucleotide conjugated to a bivalent or trivalent branched linker selected from the structures of formula (XXIV)-(XXXV) depicted in International Patent Application Publication No. WO 2016/209862.

The conjugate or ligand described herein can be attached to an iRNA oligonucleotide with a linker that can be cleavable or non-cleavable. The term "linker" or "linking group" means an organic moiety that connects two parts of a compound, e.g., covalently attaches two parts of a compound. Linkers typically comprise a direct bond or an atom such as oxygen, nitrogen, or sulfur, a unit such as NH, C(O), C(O)NH, SO, SO$_2$, SO$_2$NH, or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO$_2$, N(H), C(O), substituted or unsubstituted aryl, substituted or unsubstituted heteroaryl, substituted or unsubstituted heterocyclic; where R8 is hydrogen, acyl, aliphatic or substituted aliphatic. The linker may consist of between about 1-24 atoms, 2-24, 3-24, 4-24, 5-24, 6-24, 6-18, 7-18, 8-18, 7-17, 8-17, 6-16, 7-17, or 8-16 atoms.

A cleavable linking group is one which is sufficiently stable outside the cell, but which upon entry into a target cell is cleaved to release the two parts the linker is holding together. The cleavable linking group may be cleaved at least about 10 times, 20, times, 30 times, 40 times, 50 times, 60 times, 70 times, 80 times, 90 times, or 100 times faster in a target cell or under a first reference condition (which, e.g., may be selected to mimic or represent intracellular conditions) than in the blood of a subject, or under a second reference condition (which can, e.g., be selected to mimic or represent conditions found in the blood or serum). Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond may be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker may include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds may be used when targeting cell types rich in peptidases, such as liver cells and synoviocytes. In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals.

It is not necessary for all positions in a given compound to be uniformly modified, and in fact more than one of the aforementioned modifications can be incorporated in a single compound or even at a single nucleoside within an iRNA. The iRNA agents may be chimeric compounds. "Chimeric" iRNA compounds or "chimeras," are iRNA agents, e.g., dsRNAs, which contain two or more chemically distinct regions, each made up of at least one monomer unit, e.g., a nucleotide in the case of a dsRNA compound. These RNAi agents typically contain at least one region wherein the RNA is modified so as to confer upon the RNAi agent increased resistance to nuclease degradation, increased cellular uptake, and/or increased binding affinity for the target nucleic acid. An additional region of the RNAi agent can serve as a substrate for enzymes capable of cleaving RNA: DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

The RNA of an RNAi agent may be modified by a non-ligand group. Non-ligand molecules may be conjugated to RNAi agents in order to enhance the activity, cellular distribution or cellular uptake of the iRNA, and procedures for performing such conjugations are available in the scientific literature. Such non-ligand moieties include lipid moieties, such as cholesterol, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Typical conjugation protocols involve the synthesis of an RNA bearing an amino linker at one or more positions of the sequence. The amino group is then reacted with the molecule being conjugated using appropriate coupling or activating reagents. The conjugation reaction can be performed either with the RNA still bound to a solid support or following cleavage of the RNA, in solution phase. Purification of the RNA conjugate by HPLC typically affords the pure conjugate.

The delivery of an RNAi agent to a cell e.g., a cell within a subject, such as a human subject (e.g., a subject in need thereof) can be achieved in a number of different ways. For example, delivery may be performed by contacting a cell with an RNAi agent either in vitro or in vivo. In vivo delivery may also be performed directly by administering a composition comprising an RNAi agent, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an RNAi agent (see e.g., WO 94/02595, which is incorporated herein by reference). For in vivo delivery, factors to consider in order to deliver an iRNA molecule include, for example, biological stability of the delivered molecule, prevention of non-specific effects, and accumulation of the delivered molecule in the target tissue. The non-specific effects of an RNAi agent can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the RNAi agent to be administered. Local administration of an RNAi agent has resulted in successful knockdown of gene products. For example, intraocular delivery of a VEGF dsRNA by intravitreal injection in cynomolgus monkeys and subretinal injections in mice were both shown to prevent neovascularization in an experimental model of age-related macular degeneration. In addition, direct intratumoral injection of a dsRNA in mice reduces tumor volume and can prolong survival of tumor-bearing mice. RNA interference has also shown success with local delivery to the CNS by direct injection, and to the lungs by intranasal administration.

For administering an RNAi agent systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. RNAi agents can be modified by chemical conjugation to lipophilic groups such as cholesterol to enhance cellular uptake and prevent degradation. For example, an RNAi agent directed against ApoB conjugated to a lipophilic cholesterol moiety was injected systemically into mice and resulted in knockdown of apoB mRNA in both the liver and jejunum. Conjugation of an RNAi agent to an aptamer has been shown to inhibit tumor growth and mediate tumor regression in a mouse model of prostate cancer. Alternatively, the RNAi agent may be delivered using drug delivery systems such as a nanoparticle, a dendrimer, a polymer, liposomes, or a cationic delivery system.

Positively charged cationic delivery systems facilitate binding of an iRNA molecule (negatively charged) and also enhance interactions at the negatively charged cell membrane to permit efficient uptake of an RNAi agent by the cell. Cationic lipids, dendrimers, or polymers can either be bound to an iRNA, or induced to form a vesicle or micelle that encases an RNAi agent. The formation of vesicles or micelles further prevents degradation of the RNAi agent when administered systemically. Methods for making and administering cationic-iRNA complexes are well within the abilities of one skilled in the art. Some non-limiting examples of drug delivery systems useful for systemic delivery of RNAi agents include DOTAP, Oligofectamine, "solid nucleic acid lipid particles", cardiolipin, polyethyleneimine, and polyamidoamines. An RNAi agent may form a complex with cyclodextrin for systemic administration. Methods for administration and pharmaceutical compositions of RNAi agents and cyclodextrins are described, for example, in U.S. Pat. No. 7,427,605.

An RNAi agent targeting the HNF4α-P2 isoform mRNA can be expressed from genes inserted into DNA or RNA vectors. Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid. The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively, each individual strand of a dsRNA can be transcribed by promoters both of which are located on the same expression plasmid. A dsRNA may be expressed as inverted repeat polynucleotides joined by a linker polynucleotide sequence such that the dsRNA has a stem and loop structure.

Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA-expressing vectors can be systemic, such as by intravenous or intramuscular administration, by administration to target cells ex-planted from the patient followed by reintroduction into the patient, or by any other means that allows for introduction into a desired target cell.

Viral vector systems which can be utilized with the methods and compositions described herein include, but are not limited to: (a) adenovirus vectors; (b) retrovirus vectors, including, but not limited to, lentiviral vectors, moloney murine leukemia virus, etc.; (c) adeno-associated virus vectors; (d) herpes simplex virus vectors; (e) SV40 vectors; (f) polyoma virus vectors; (g) papilloma virus vectors; (h) picornavirus vectors; (i) pox virus vectors such as an orthopox, e.g., vaccinia virus vectors or avipox, e.g., canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g., EPV and EBV vectors. Constructs for the recombinant expression of an iRNA will generally require regulatory elements, e.g., promoters, enhancers, etc., to ensure the expression of the iRNA in target cells. Other factors to consider for vectors and constructs are known in the art.

Also provided herein are pharmaceutical compositions and formulations which include the RNAi agents. In one aspect, provided herein are pharmaceutical compositions containing an RNAi agent, as described herein, and a pharmaceutically acceptable carrier. The pharmaceutical compositions containing the RNAi agent are useful for treating a disease or disorder associated with the expression or activity of an HNF4α-P2 isoform mRNA, such as, liver disease, liver damage, liver inflammation, or liver failure, such as acute liver failure, ALD, AH, or ACLF.

Such pharmaceutical compositions are formulated based on the mode of delivery. One example is compositions that are formulated for systemic administration via parenteral delivery, e.g., by intravenous (IV) or for subcutaneous delivery. Another example is compositions that are formulated for direct delivery into the liver, e.g., by infusion into the liver, such as by continuous pump infusion.

The pharmaceutical compositions may be formulated and/or administered in dosages sufficient to inhibit expression of an HNF4α-P2 isoform mRNA. In general, a suitable dose of an RNAi agent will be in the range of from about 0.001 to about 200.0 milligrams per kilogram body weight of the recipient per day, generally in the range of from about 1 to 50 mg per kilogram body weight per day. A suitable dose of an RNAi agent may be in the range of from about 0.1 mg/kg to about 5.0 mg/kg, e.g., about 0.3 mg/kg and about 3.0 mg/kg. A repeat-dose regimen may include administration of a therapeutic amount of RNAi agent on a regular basis, such as every other day or once a year. The RNAi agent may be administered from about once per month to about once per quarter (e.g., about once every three months). After an initial treatment regimen, the treatments may be administered on a less frequent basis.

The methods herein may include administering a composition featured herein such that expression of the target HNF4α-P2 isoform mRNA is decreased, such as for about 1, 2, 3, 4, 5, 6, 7, 8, 12, 16, 18, 24 hours, 28, 32, or about 36 hours. Expression of the target HNF4α-P2 isoform mRNA may be decreased for an extended duration, e.g., at least about two, three, four days or more, e.g., about one week, two weeks, three weeks, or four weeks or longer.

Before administration of a full dose of the RNAi agent, patients can be administered a smaller dose, such as a 5% infusion reaction, and monitored for adverse effects, such as an allergic reaction. In another example, the patient can be monitored for unwanted immune-stimulatory effects, such as increased cytokine (e.g., TNF-alpha or INF-alpha) levels.

The skilled artisan will appreciate that certain factors can influence the dosage and timing required to effectively treat a subject, including, but not limited to, the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual RNAi agents encompassed herein can be made using conventional methodologies or on the basis of in vivo testing using an appropriate animal model, as described elsewhere herein.

The data obtained from cell culture assays and animal studies can be used in formulating a range of dosage for use in humans. The dosage of compositions featured herein lies generally within a range of circulating concentrations that include the $ED_{50}$ with little or no toxicity. The dosage can vary within this range depending upon the dosage form employed and the route of administration utilized. For any compound used in the methods described herein, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The pharmaceutical composition may be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration. The RNAi agent may be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids, and powders. Conventional pharmaceutical carriers, aqueous, powder, or oily bases, thickeners and the like can be necessary or desirable. Suitable topical formulations include those in which the RNAi agents featured herein are in admixture with a topical delivery agent such as lipids, liposomes, fatty acids, fatty acid esters, steroids, chelating agents, and surfactants. Suitable lipids and liposomes include neutral (e.g., dioleoylphosphatidyl DOPE ethanolamine, dimyristoylphosphatidyl choline DMPC, disteroylphosphatidyl choline), negative (e.g., dimyristoylphosphatidyl glycerol DMPG), and cationic (e.g., dioleoyltetramethylaminopropyl DOTAP and dioleoylphosphatidyl ethanolamine DOTMA). RNAi agents featured herein can be encapsulated within liposomes or can form complexes thereto, in particular to cationic liposomes. Alternatively, RNAi agents may be complexed with lipids, such as cationic lipids. Suitable fatty acids and esters include, but are not limited to, arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride or diglyceride; or pharmaceutically acceptable salt thereof. Topical formulations are described in detail in U.S. Pat. No. 6,747,014.

An RNAi agent for use in the methods described herein can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the RNAi agent composition. The lipophilic material isolates the aqueous interior from an aqueous exterior, which typically does not include the RNAi agent, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the RNAi agent are delivered into the cell where the RNAi agent can specifically bind to a target RNA and can mediate RNAi agent. In some cases, the liposomes are also specifically targeted, e.g., to direct the RNAi agent to particular cell types.

A liposome containing a RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary, a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the technical disclosure of which is incorporated herein by reference. Liposome formation also may prepared or used as described in U.S. Pat. No. 4,897,355 or 5,171,678. Commonly used techniques for preparing lipid aggregates of appropriate size for use as delivery vehicles include sonication and freeze-thaw plus extrusion. Microfluidization can be used when consistently small (50 to 200 nm) and relatively uniform aggregates are desired. These methods are readily adapted to packaging RNAi agent preparations into liposomes.

For delivery of the RNAi agent in a spray, a suitable formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray. Propellants may include hydrogen-containing chlorofluorocarbons, hydrogen-containing fluorocarbons, dimethyl ether, and diethyl ether. HFA 134a (1, 1,1,2 tetrafluoroethane) may be used.

Compositions and formulations for oral administration include powders or granules, microparticulates, nanoparticulates, suspensions, or solutions in water or nonaqueous media, capsules, gel capsules, sachets, tablets, or minitablets. Thickeners, flavoring agents, diluents, emulsifiers, dispersing aids, or binders can be desirable. Oral formulations may be those in which an RNAi agent is administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, gluchoic acid, glycholic acid, glycodeoxycholic acid, taurocholic acid, taurodeoxycholic acid, sodium tauro-24,25-dihydrofusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, l-dodecylazacycloheptan-2-one, an acylcarnitine, an acylcholine, or a monoglyceride or a diglyceride; or a pharmaceutically acceptable salt thereof (e.g., sodium). Combinations of penetration enhancers may be used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. RNAi agents may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, poly spermines, protamine, polyvinylpyridine, polythiodiethylaminomethylethylene P(TDAE), poly amino styrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Patent Application Publication No. 2003/0027780, and U.S. Pat. No. 6,747,014.

The compositions can be prepared and formulated as emulsions. Emulsions are typically heterogeneous systems of one liquid dispersed in another in the form of droplets usually exceeding 0.1 μm in diameter. Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise, a system of oil droplets enclosed in globules of water stabilized in an oily continuous phase provides an o/w/o emulsion.

An RNAi agent may be incorporated into a particle, e.g., a microparticle. Microparticles can be produced by spray-drying but may also be produced by other methods including lyophilization, evaporation, fluid bed drying, vacuum drying, or a combination of these techniques.

Penetration enhancers may be employed to affect the efficient delivery of nucleic acids, particularly RNAi agents, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs. Penetration enhancers can be classified as belonging to one of five broad categories, i.e., surfactants, fatty acids, bile salts, chelating agents, and non-chelating non-surfactants. Such compounds are well known in the art.

Certain compositions may also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney, or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4' isothiocyanostilbene-2,2'-disulfonic acid.

The compositions can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions, such as dyes, flavoring agents, preservatives, antioxidants, opacifiers, thickening agents, and stabilizers. However, such materials, when added, should not unduly interfere with the biological activities of the components of the compositions. The formulations can be sterilized and, if desired, mixed with auxiliary agents, e.g., lubricants, preservatives, stabilizers, wetting agents, emulsifiers, salts for influencing osmotic pressure, buffers, colorings, flavorings, and/or aromatic substances; and the like which do not deleteriously interact with the nucleic acid(s) of the formulation.

The RNAi agent and additional therapeutic agents may be administered at the same time and/or in the same combination, e.g., parenterally, or the additional therapeutic agent can be administered as part of a separate composition or at separate times and/or by another method known in the art or described herein.

The in vivo methods may include administering to a subject a composition containing an RNAi agent, where the RNAi agent includes a nucleotide sequence that is complementary to at least a part of an HNF4α-P2 isoform mRNA of the mammal to be treated. When the organism to be treated is a mammal such as a human, the composition can be administered by any means known in the art including, but not limited to oral, intraperitoneal, or parenteral routes, including intracranial, intraventricular, intraparenchymal, intrathecal, intravenous, intramuscular, subcutaneous, transdermal, airway (aerosol), nasal, rectal, and topical (including buccal and sublingual) administration. The compositions may be administered by intravenous infusion or injection. The compositions may be administered by subcutaneous injection. Administration may be via a depot injection. The administration may be via a pump. The pump may be an external pump or a surgically implanted pump, such as a subcutaneously implanted osmotic pump or an infusion pump. An infusion pump may be used for intravenous, subcutaneous, arterial, or epidural infusions. The infusion pump may be a subcutaneous infusion pump. The pump may be a surgically implanted pump that delivers the RNAi agent to the liver.

Pharmaceutical compositions described herein include (a) one or more iRNA compounds and (b) one or more agents which function by a non-RNAi mechanism and which are useful in treating an HNF4α-P2 isoform mRNA-associated disorder. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred.

Also described herein are methods of using an RNAi agent and/or a composition containing an RNAi agent to reduce and/or inhibit HNF4α-P2 isoform mRNA expression in a cell. The methods include contacting the cell with an RNAi agent described herein and maintaining the cell for a time sufficient to obtain degradation of the HNF4α-P2 isoform mRNA, thereby inhibiting expression HNF4α-P2 isoform mRNA in the cell. Reduction in gene expression can be assessed by any methods known in the art. For example, a reduction in the expression of HNF4α-P2 isoform mRNA may be determined by determining the mRNA expression level HNF4α-P2 isoform mRNA using methods routine to one of ordinary skill in the art, e.g., northern blotting, qRT-PCR; by determining the protein level of HNF4α-P2 isoform mRNA using methods routine to one of ordinary skill in the art, such as western blotting, immunological techniques. A reduction in the expression of HNF4α-P2 isoform mRNA may also be assessed indirectly by measuring a decrease in biological activity of HNF4α-P2 isoform mRNA.

In the methods, the cell may be contacted in vitro or in vivo, e.g., the cell may be within a subject. A cell suitable for treatment using the methods described herein may be any cell that expresses an HNF4α-P2 isoform mRNA. A cell suitable for use in the methods described herein may be a mammalian cell, e.g., a primate cell (such as a human cell or a non-human primate cell, e.g., a monkey cell or a chimpanzee cell), a non-primate cell (such as a cow cell, a pig cell, a camel cell, a llama cell, a horse cell, a goat cell, a rabbit cell, a sheep cell, a hamster, a guinea pig cell, a cat cell, a dog cell, a rat cell, a mouse cell, a lion cell, a tiger cell, a bear cell, or a buffalo cell), a bird cell (e.g., a duck cell or a goose cell), or a whale cell. The cell may be a human cell, e.g., a human liver cell.

HNF4α-P2 isoform mRNA expression is inhibited in the cell by at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100%. HNF4α-P2 isoform mRNA expression may be inhibited by at least 20%. The HNF4α-P2 isoform mRNA expression is inhibited selectively with respect to HNF4α-P1 isoform mRNA expression, meaning the expression of HNF4α-P2 isoform mRNA is inhibited to a greater extent, e.g., a statistically significantly greater extent, than expression of HNF4α-P1 isoform mRNA, e.g., by at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100%, such as at least 20% greater extent.

An RNAi agent described herein may be administered as a "free RNAi agent." A free RNAi agent is administered in the absence of a pharmaceutical composition. The naked RNAi agent may be in a suitable buffer solution. The buffer solution may comprise acetate, citrate, prolamine, carbonate, or phosphate, or any combination thereof. The buffer solution may be phosphate buffered saline (PBS). The pH and osmolarity of the buffer solution containing the RNAi agent can be adjusted such that it is suitable for administering to a subject.

Also provided herein are methods for the use of an RNAi agent or a pharmaceutical composition thereof, e.g., for treating a subject that would benefit from reduction and/or inhibition of HNF4α-P2 isoform mRNA expression, e.g., a subject having liver disease, liver damage, liver inflammation, or liver failure, such as acute liver failure, ALD, AH, or ACLF, in combination with other pharmaceuticals and/or other therapeutic methods, e.g., with known pharmaceuticals and/or known therapeutic methods, such as, for example, those which are currently employed for treating these disorders. For example, an RNAi agent targeting HNF4α-P2 isoform mRNA may be administered to a subject having a liver disease, liver damage, liver inflammation, or liver failure, such as acute liver failure, ALD, AH, or ACLF in combination with, e.g., antioxidant agents (such as N-Acetyl Cysteine), anti-inflammatory drugs (prednisolone, anakinra), liver-support devices (ELAD), high volume plasma exchange, human albumin, growth factors (G-CSF), or vitamins (vitamin K).

Examples

This human-based translational study combined integrated multi-OMICs from a large cohort of human samples along with in vitro and experimental animal models with a goal to address this knowledge gap.

Identification of molecular drivers is hampered by the lack of suitable animal models. By performing RNA-seq in livers from patients with different phenotypes of alcohol-induced liver disease (ALD), development of AH is seen to be characterized by defective activity of liver-enriched transcription factors (LETFs). AH was associated by a marked decrease in HNF4α-depending gene expression along with a marked expression of the fetal HNF4α isoform (P2). P2 isoforms have same DNA binding domain of P1 "adult type" HNF4α isoforms but lack the activation domain 1 (AF1). A competitive inhibition of P2 over P1 protein variants is shown. The inhibition of P2 isoforms with a novel siRNA molecule in primary human hepatocytes and in hepatocyte cell lines led to an improvement on main HNF4A-depending genes, which regulate essential liver functions such as gluconeogenesis, bile acid synthesis and secretion, clotting factor synthesis and the urea cycle. Modulation of HNF4α-depending gene expression by the silencing of P2 isoforms may be beneficial to improve hepatocellular function in patients with alcohol-related Liver Failure, but also for liver failure caused by different etiologies.

To uncover the mechanisms involved in progression to AH in patients with ALD, a comprehensive analysis of liver RNA sequencing (RNA-seq) data was performed from a large series of patients with different disease stages including normal liver, early alcoholic steatohepatitis (ASH), AH with liver failure and a unique set of explants from patients with AH that underwent urgent liver transplantation (Thursz, M. R., et al. Prednisolone or pentoxifylline for alcoholic hepatitis. N Engl J Med 372, 1619-1628 (2015)). As diseased controls, patients with non-alcoholic fatty liver disease (NAFLD), chronic hepatitis C and compensated HCV cirrhosis were included. The principal component analysis (PCA) showed patient clustering according to the progressive clinical phenotypes. Thus, while early ASH clustered along with chronic hepatitis C and NASH close to normal livers, patients with AH showed a much more deregulated transcriptome. A comparative analysis was performed between normal livers and different ALD phenotypes. Analytical parameters of liver injury (i.e., AST) and hepatocellular synthetic function (i.e., INR, serum bilirubin and albumin) as well as clinical scoring systems (i.e., Child-Pugh and MELD) were markedly impaired after the onset of AH. Unbiased clustering and Short Time Expression Miner (STEM) algorithm identified 13 profiles of gene expression across the 4 selected disease stages. These profiles were grouped into 4 main patterns along ALD progression including compensatory transient gene expression changes in early stages, genes progressively up or down-regulated along disease progression or genes up or down-regulated only after the onset of liver failure. A detailed gene set enrichment analysis revealed down-regulation of genes related to basic hepatocyte functions (i.e., metabolism of amino acids and lipids, biological oxidations, mitochondrial function and bile acid metabolism), while cell proliferation, extracellular matrix regulation and inflammation related pathways were enriched among up-regulated genes. To gain insight into the main drivers of gene expression that could result in the development of hepatocellular failure in AH, the predicted activity of transcription factors was analyzed using a complementary approach, by combining the search of transcription factor binding motifs in the promoter of differentially expressed genes (DEG) and by the use of Ingenuity Pathway Analysis (IPA) software to uncover predicted upstream transcription factor activity (see Material and Methods section). Early compensated state of ALD was characterized by an increased predicted activity of the hepatoprotective transcription factor PPAR-γ. In contrast, development of AH was associated with a profound decrease in the activity of LETFs, especially HNF4α (FIG. 1A). The results obtained in human livers were assessed in several animal models of early and advanced ALD. While a model of early experimental ALD (HFD plus intragastric EtOH for 3 weeks) showed a marked activation of PPAR-γ, a model of severe ALD (CCL4 plus intragastric EtOH for 9 weeks) was characterized by decreased predicted activation of FOXA-1, but not HNF4α. Preserved HNF4α function could explain the lack of liver failure (i.e., jaundice and coagulopathy) in mice models of severe ALD.

Figure 2A:
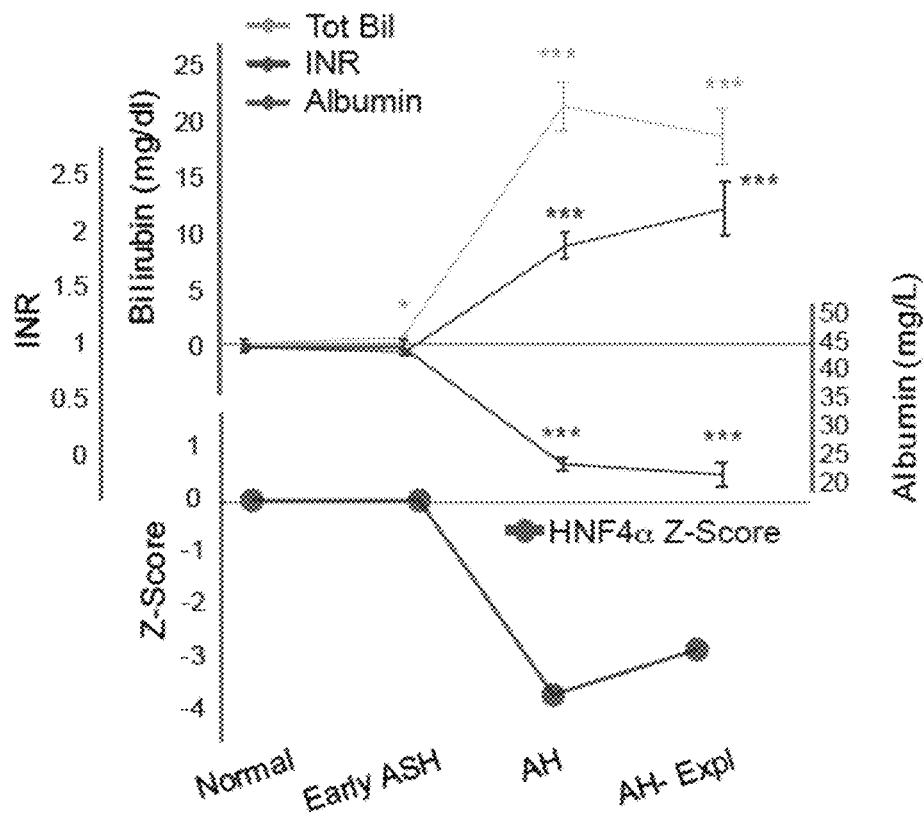
Figure 2B:
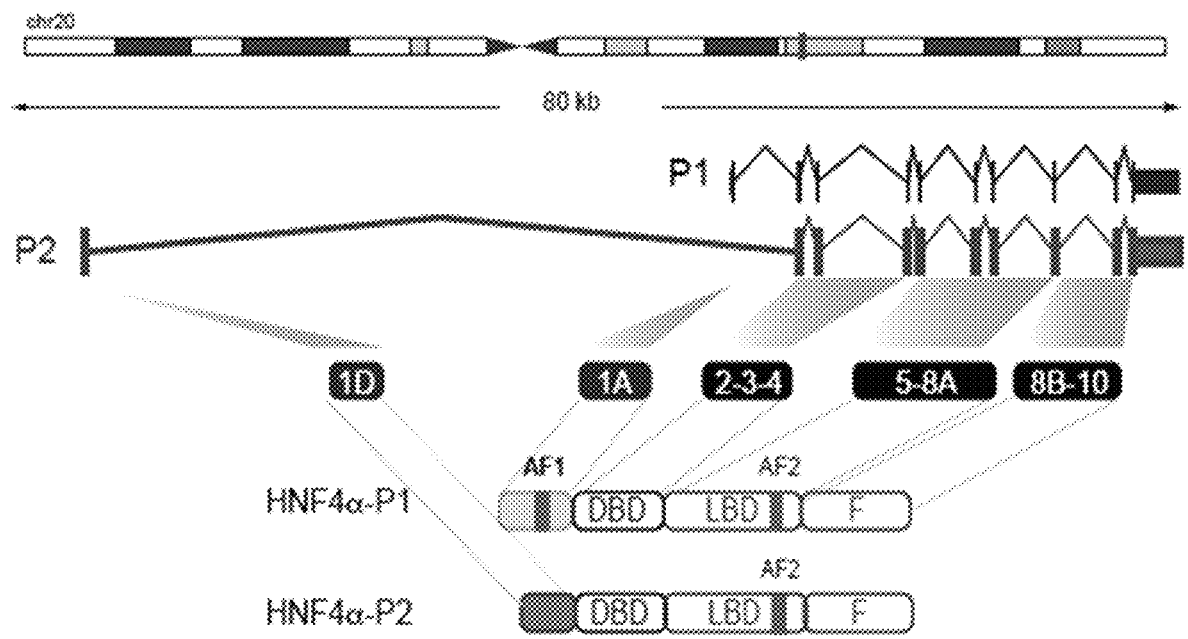
(FIG. 2B) Scheme of HNF4A gene fetal and adult isoforms structure and protein variants. During embryonic development, P2 promoter is used and alternative splicing of the first exon is produced, originating the fetal isoforms a7-12, who lack the AF-1 domain in the N-terminal of the protein. Alternative splicing of the 10th exon originates C-terminal variants (not presented here).
Figure 2C:
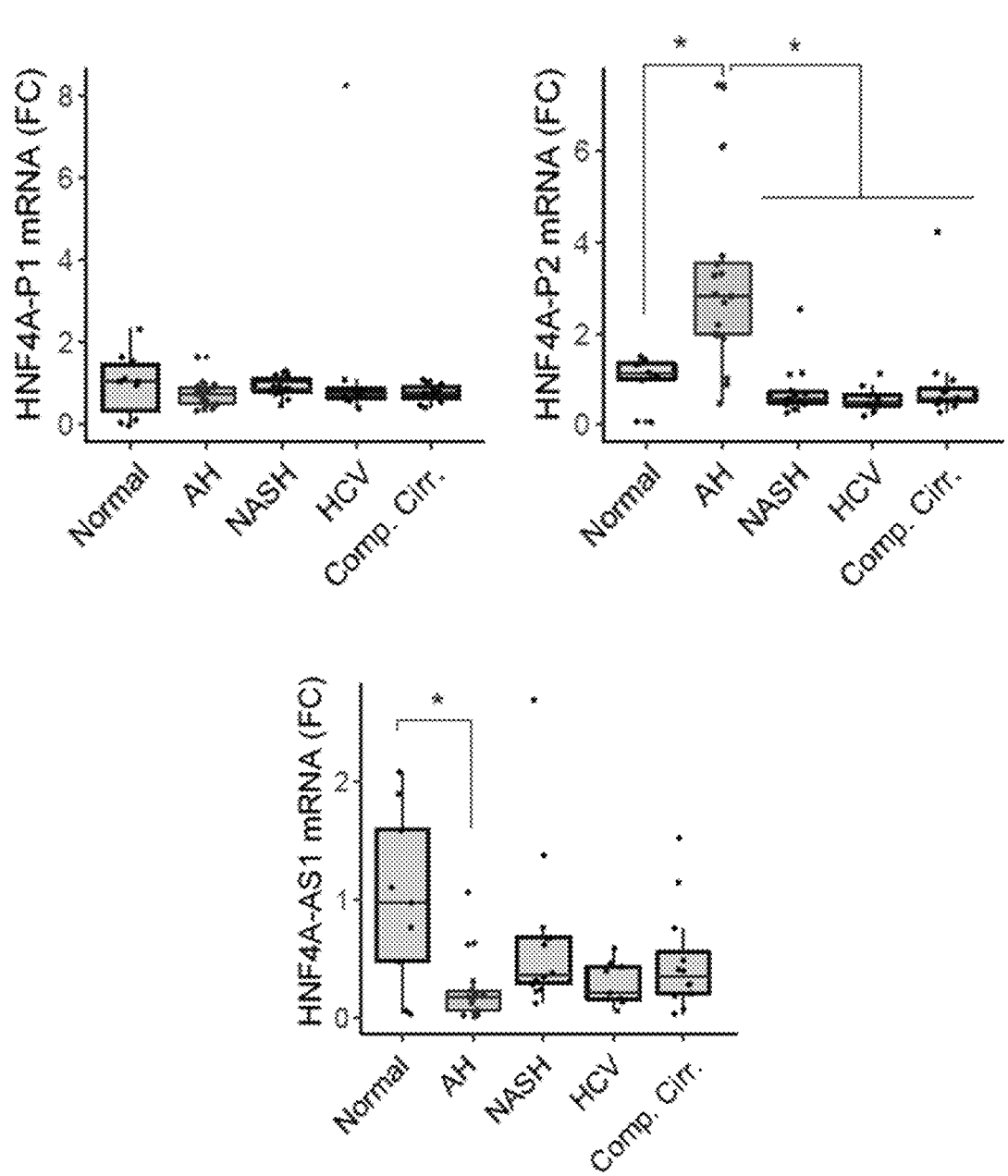
(FIG. 2C) Real-Time PCR of HNF4A-P1 and P2 dependent isoforms, and of the lncRNAN HNF4A-AS1, who shares promoter with HNF4A-P1 of the same patients in FIGS. 1A and 1B.
Figure 2D:
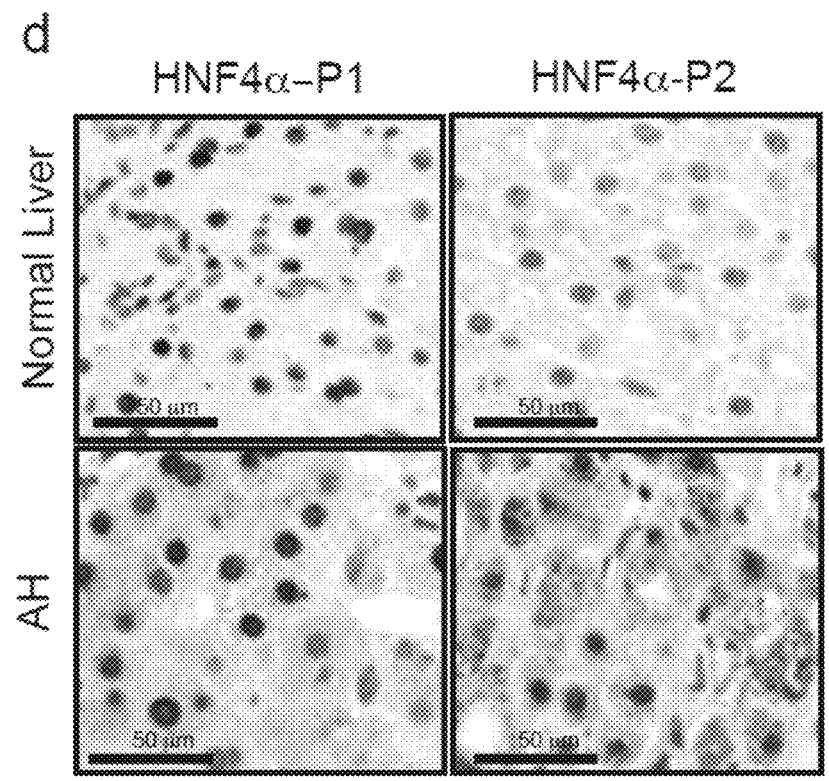
(FIG. 2D) Immunohistochemical detection of adult and fetal HNF4A protein variants (hereinafter P1 and P2) in patients with AH (n=9), and controls (n=9), using specific antibodies against the N-terminal residues.
Figure 2E:
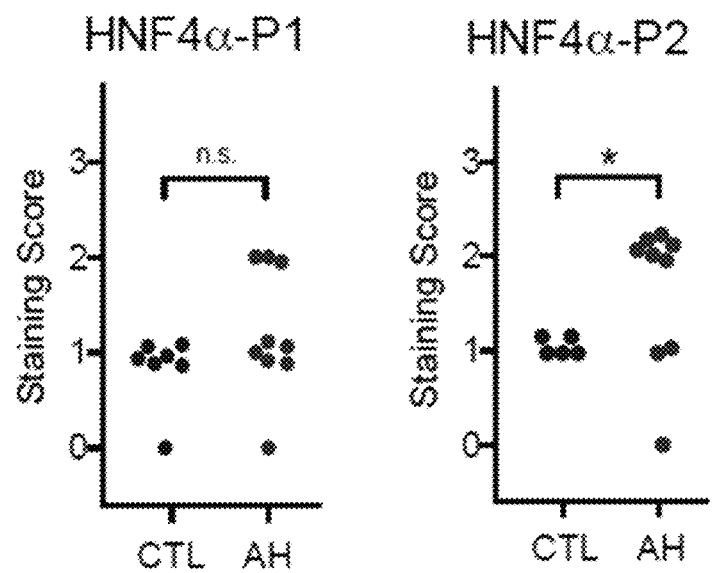
(FIG. 2E) Semi-quantitative assessment of IHC signal for each antibody for nuclear staining.

The correlation between parameters indicative of liver synthetic function and HNF4α activity was studied. As shown in FIG. 2A, development of liver failure in the setting of AH, as indicated by elevated serum bilirubin levels and INR and decreased albumin synthesis, was strongly associated with a negative HNF4α Z-Score on IPA analysis. HNF4α is known to have a fetal isoform driven by a ~45 kb upstream alternative promoter (P2-HNF4α). During embryonic development, the P2 promoter is used and alternative splicing of the first exon is produced, originating the fetal isoforms α7-12. These variants lack the AF-1 domain in the N-terminal of the protein resulting in less transactivation activity, affecting its interaction with co-regulators (FIG. 2B). The relevance of P2 derived isoforms in adult human liver disease is not well-known. The expression of N-terminal isoforms was studied in normal and AH human livers. HNF4α-P1 mRNA remained unchanged in AH, while there was a dramatic up-regulation in the expression of the fetal HNF4α-P2 isoform in livers from patients with AH (FIG. 2C). It was found that the expression of the lncRNAN HNF4A-AS1, which shares the P1 promoter region with HNF4A, was downregulated in patients with AH (FIG. 2C). Up-regulation of HNF4α-P2 was not seen in early forms of ALD or in other types of liver diseases such as NASH and chronic hepatitis C. In order to further explore the regulation of the HNF4α locus, we used a specific computational tool (Multivariate Analysis of Transcript Splicing—MATS—) (Shen, S., et al. MATS: a Bayesian framework for flexible detection of differential alternative splicing from RNA-Seq data. *Nucleic Acids Res* 40, e61 (2012)) to assess differences in HNF4α splicing between normal and AH livers. AH livers showed increased expression of exon 1D, 4,5, 6,9 and 10. Correlation analysis of exon expression suggest a profound deregulation of HNF4A gene splicing in AH not only by the increase of P2 isoforms, but also by the decrease of physiological exon exclusion in C-terminal exons. At the protein level, the HNF4α-P1 signal was detected in the nuclei of both normal and AH hepatocytes. Conversely, the HNF4α-P2 isoform, barely detected in the nucleus of normal livers, was markedly up-regulated in AH hepatocytes (FIGS. 2D and 2E). Other important LETFs inhibited in AH such as HNF1α and FOXA-1 showed decreased nuclear expression and increased cytoplasmic localization.

Figures 2F, 2G:
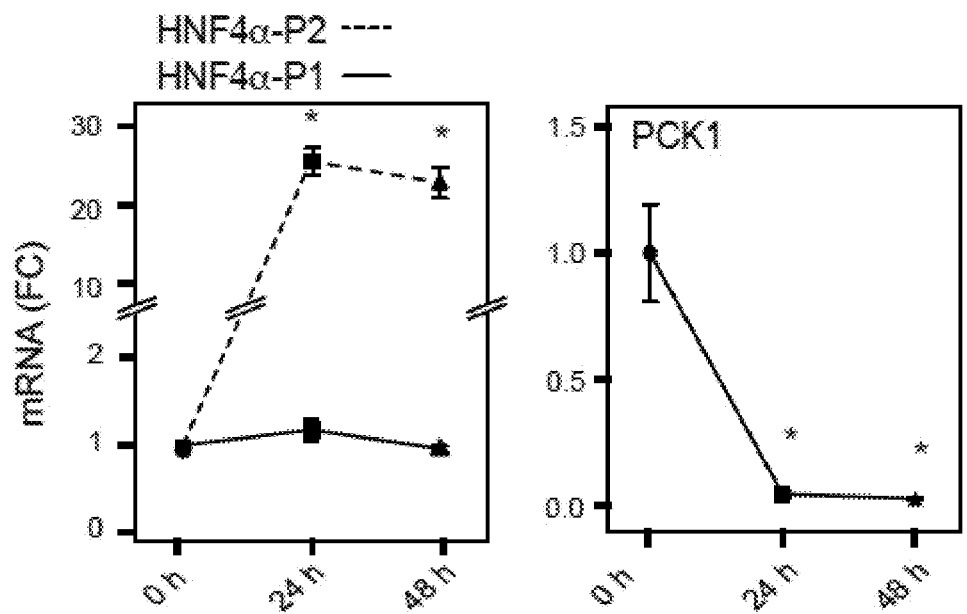
(FIGS. 2F-2I) Primary human hepatocytes were cultured in hepatocyte growth media and collected at baseline and at 24 and 48 h (n=3 for each time point). Quantitative RT-PCR of (FIG. 2F) HNF4a-P1 and P2 isoforms, (FIG. 2G) phosphoenol-pyruvate carboxykinase (PCK1) and (FIG. 2H) albumin (ALB).
Figure 2H:
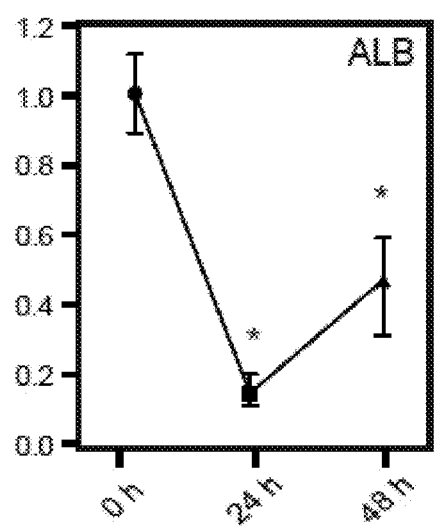
Figure 2I:
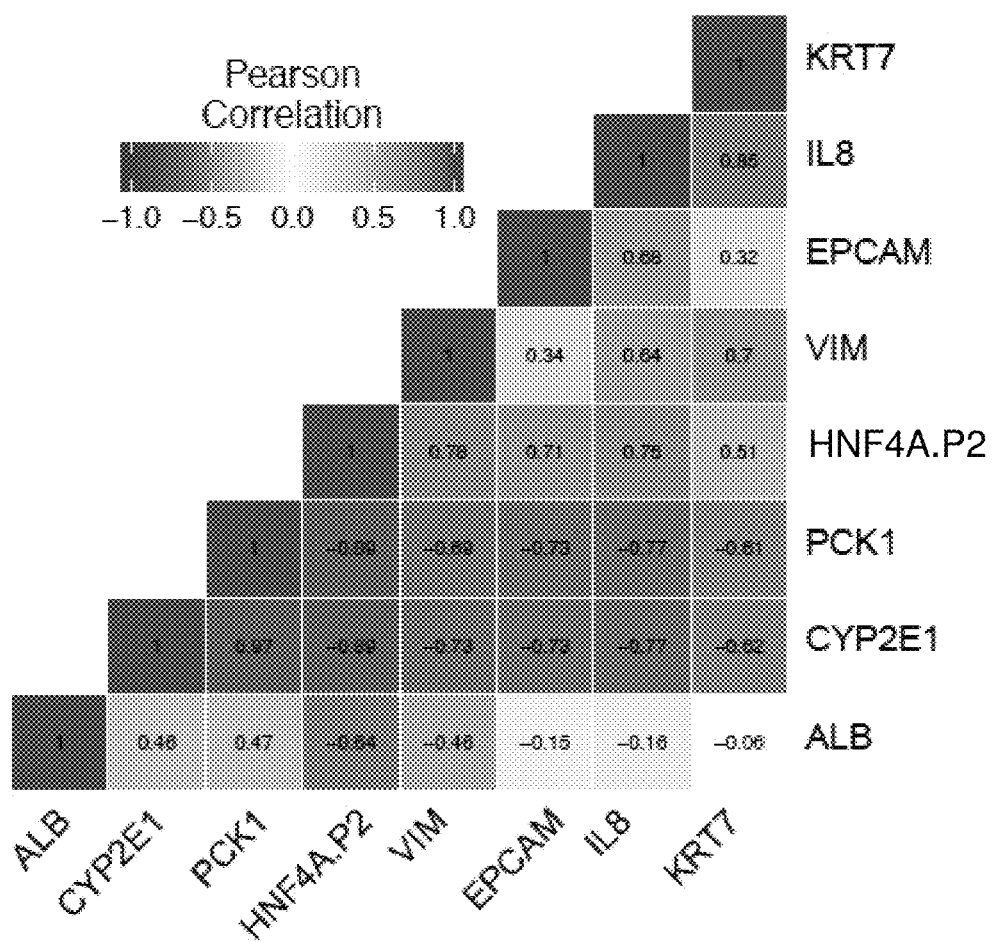
Figure 2Q:
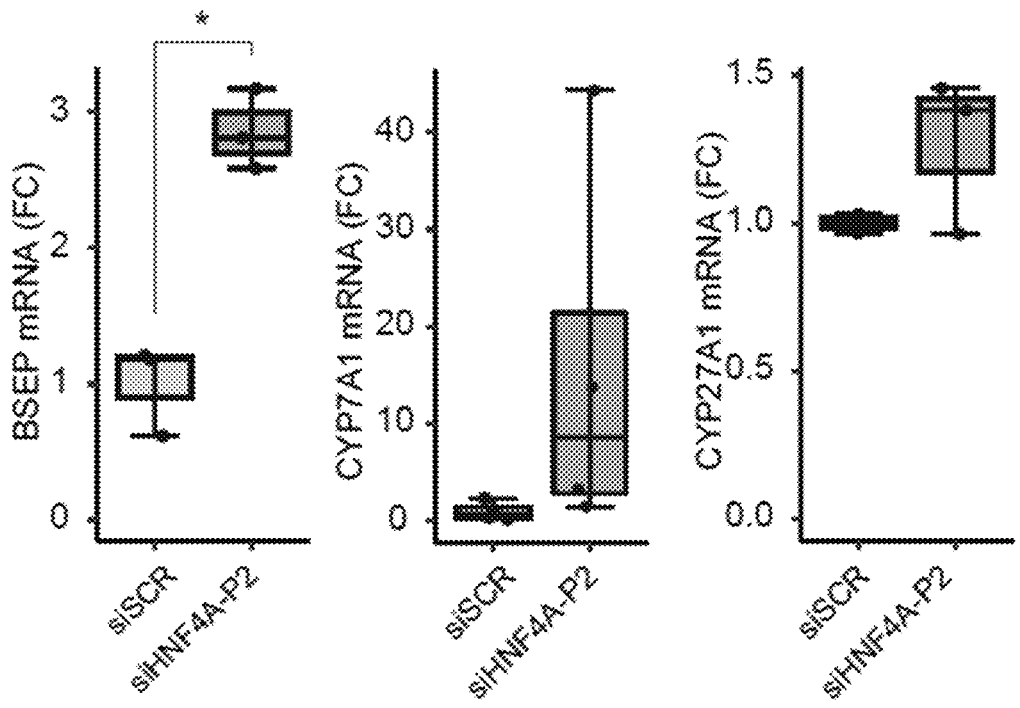
Figures 2R, 2S:
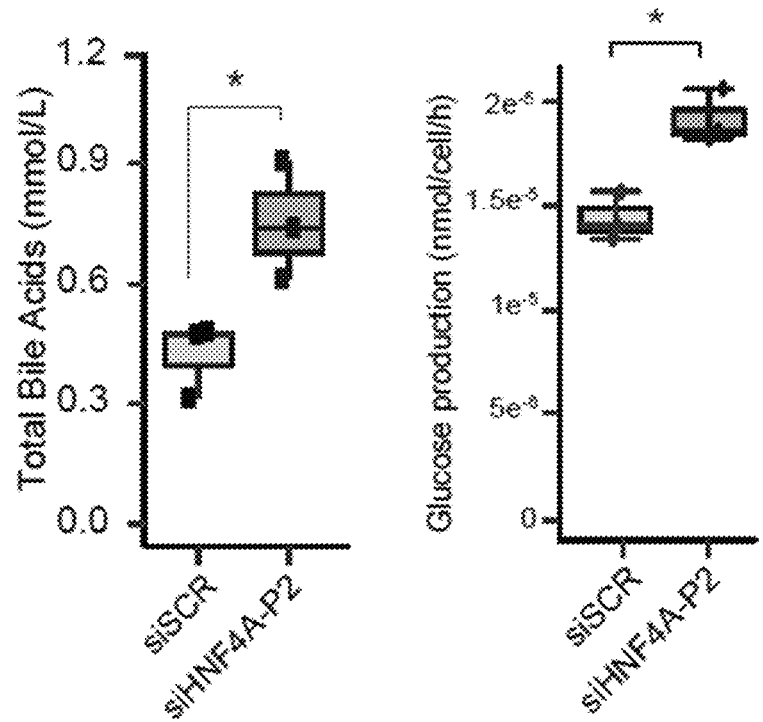

Whether P2 expression in hepatocytes contributes to the loss of mature hepatocyte biological functions during AH including bile acid homeostasis was determined, as well as metabolic and synthetic functions. Because primary hepatocytes undergo de-differentiation in culture, the expression of HNF4α isoforms during this process was examined. Gene expression of the P1 isoform did not change during the first 48 h, while the P2 isoform was 30-fold up-regulated at early time points (FIG. 2F). Phosphoenolpyruvate carboxy-kinase 1 (PCK1), the rate-limiting enzyme in gluconeogenesis, and albumin (ALB) mRNA levels were down-regulated at 24 and 48 h (FIGS. 2G and 2H). Importantly, HNF4α-P2 mRNA levels correlated negatively with genes related to hepatocyte function (such as PCK1, ALB and CYP2E1) and positively with genes related to hepatocyte de-differentiation (such as Vimentin, Epcam, IL8 and KRT7) (FIG. 2I). In AH patients, increased expression of progenitor cell markers and markers of epithelial-to-mesenchymal transition (EMT) were found, suggesting a de-differentiation of hepatocytes, furtherly suggested by correlation analysis with tissue and cell type published gene sets. Gain and loss-of function studies were performed to elucidate the role of P2 in hepatocyte biological functions. Overexpression of HNF4α-P2 results in decreased expression of the HNF4α target gene PCK1 (FIGS. 2J and 2K). In contrast, abrogation of HNF4α-P2 resulted in increased HNF4α-P1 gene and protein expression (FIGS. 2I-2N), without affecting the levels of HNF4A-AS1 (FIG. 2O). The expression of HNF4α target genes involved in hepatocyte metabolic, secretory and synthetic functions such as PCK1, coagulation factor VII (F7), ALB, CYP7A1 and biliary salt export pump (BSEP) was increased (FIGS. 2P and 2Q). Moreover, this maneuver restored bile acid synthesis and secretion (FIG. 2R) and stimulated glucose production (FIG. 2S) in human primary hepatocytes. Overall, these results suggest that P2 overexpression negatively regulates HNF4α-dependent gene expression and several biological properties of mature hepatocytes that are commonly lost in AH.

The potential mechanisms involved in HNF4α P1-P2 imbalance during the development of liver failure in AH was explored. Unbiased analysis of transcriptomic changes in patients progressing to AH uncovered main upstream regulators. When comparing the expression of top enriched upstream regulators through different phenotypes, TGβ1 was found to be the most relevant factor, followed by EGF. Expression of TGβ1-related genes such as TGβ1 receptors 1 and 2 and osteopontin (SPP1), as well as the EGFR ligand Amphiregulin (AREG), were markedly increased in AH livers. TNFα transcript levels were not specifically elevated in AH when compared with other liver disease. It was then hypothesized that TGβ1 and AREG regulate HNF4α P1-P2 relative expression in hepatocytes. TGβ1 and AREG synergistically decreased HNF4α-P1 expression and increased HNF4α-P2 through activation of TGFβ1RI/TAK1 and the EGFR/MEK/ERK axis respectively. The effect of TGβ1 and AREG on HNF4α levels involved proteasome-related degradation. TGβ1 reduced HNF4α-P1 target genes and the blockage of TGFβ1RI restored the levels of rate-limiting enzymes in mature hepatocytes such as PCK1 and ornithine-transcarbamylase (OTC). It was then explored if the detrimental effect of TGβ1 on hepatocyte function is mediated by HNF4α-P2 increase. Hepatocytes transfection with siRNA targeting P2 isoforms abolished TGβ1-mediated suppression of HNF4α-P1. The inhibition of HNF4α-P1 dependent genes, in particular CYP7A1 and BSEP, was also significantly prevented by P2 silencing (FIGS. 3A-3E). These results suggest that the re-expression of HNF4α fetal isoforms in AH could participate in TGβ1-induced loss of hepatocellular function, pointing to these isoforms as potential therapeutic targets.

Figure 3A:
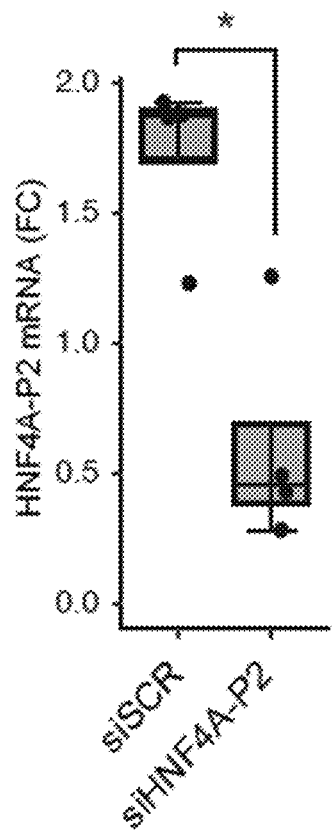
FIGS. 3A-3F. TGFb1 is a major transcriptome regulator in AH, downregulates HNF4a partially by inducing HNF4a-P2 and is modulated by PPARg agonists and corticosteroids.
Figure 3B:
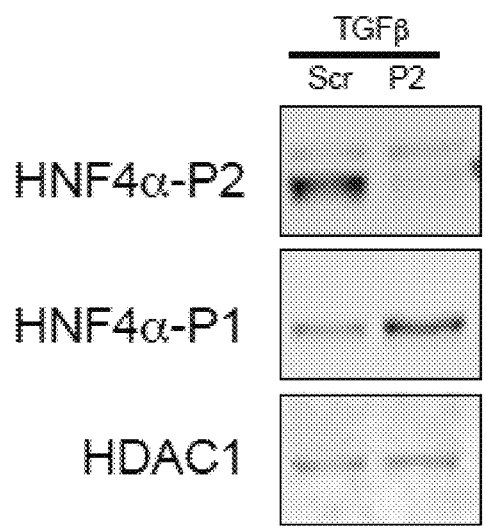
Figure 3C:
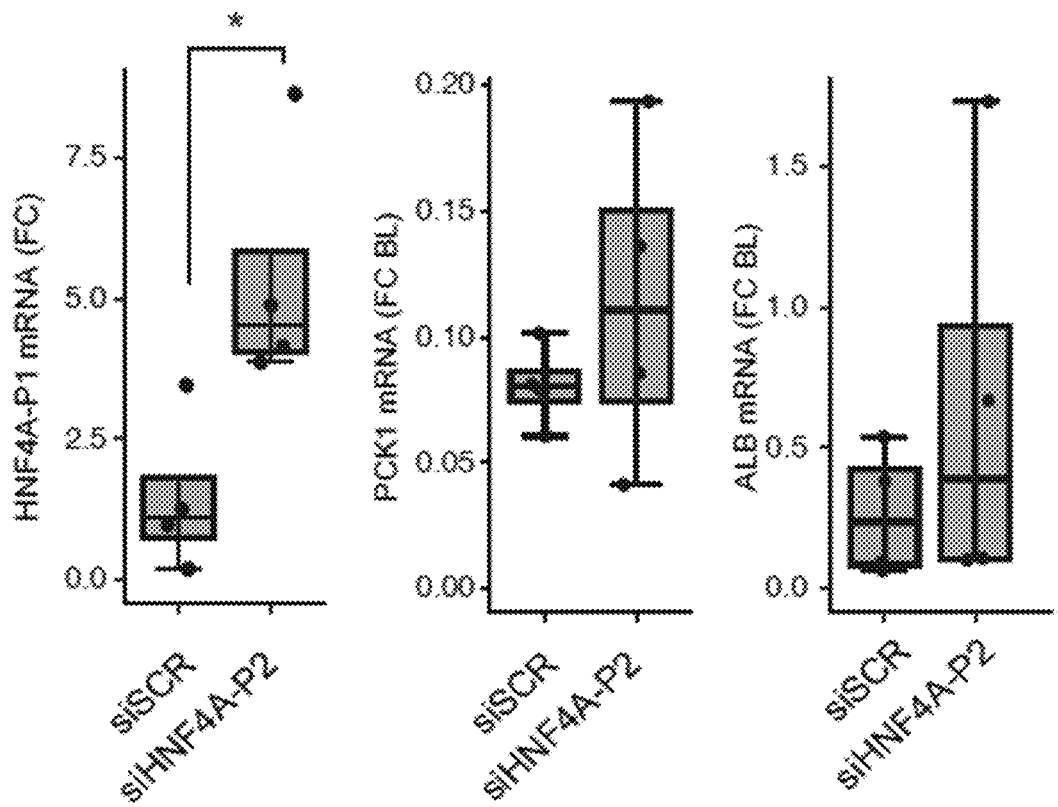
Figure 3D:
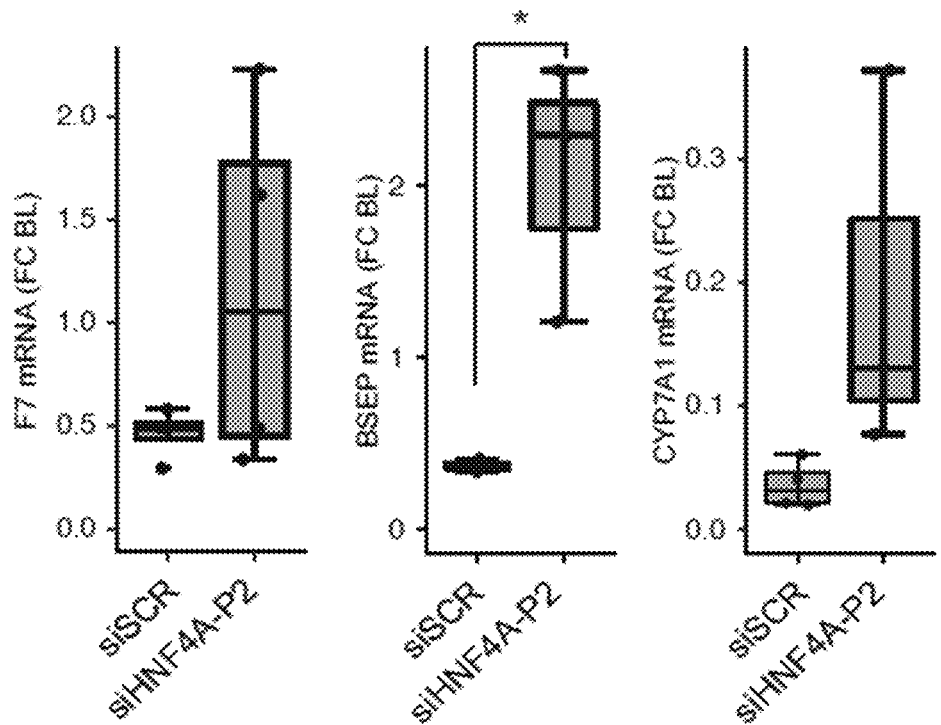
Figure 3E:
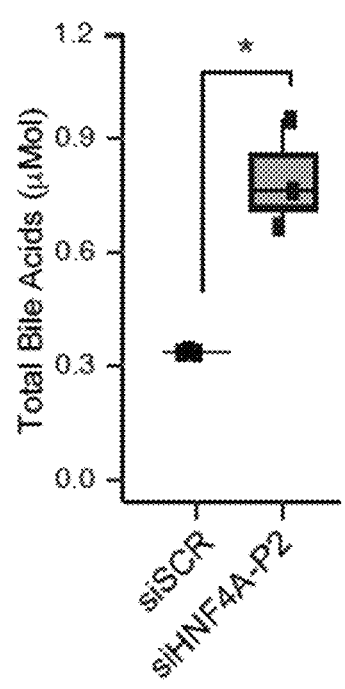
Figure 3F:
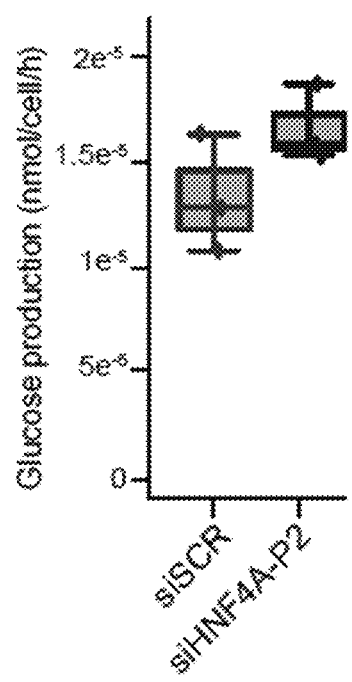

Next, potential mechanisms were identified that maintain the normal HNF4α P1/P2 ratio during the compensated stages of ALD. Transcriptomic footprint analysis revealed a marked predicted activation of PPAR-γ in early phases of ALD. Whether PPAR-γ antagonizes TGβ1-mediated HNF4α dysregulation was explored. The PPAR-γ agonists rosiglitazone and pioglitazone decreased the abundance of P2 isoforms and increased P1 isoforms (FIG. 3F). The effect on P2 protein expression, but not P1, was regulated post-transcriptionally. The effect of rosiglitazone on HNF4α-P1 mRNA levels was dose dependent. TGβ1-mediated ALB down-regulation was restored by PPAR-γ activation. Overall, these results suggest that, in hepatocytes, PPAR-γ counteracts TGβ1-mediated HNF4α dysregulation.

Finally, whether genetic or epigenetic factors are involved in the defective LETFs function in AH was explored. To address this question, GWAS data was first analyzed from a large cohort of AH patients and patients with ethanol abuse but never decompensated. None of the single nucleotide polymorphisms (SNP) detected in LETFs including HNF4α, either genotyped or imputed, were significantly associated with AH development. Because exposure to either TGβ1 or alcohol have been involved in DNA methylation and chromatin remodeling, it was hypothesized that the disruption of the expression and activity of the transcriptional master regulators (i.e., LETFs) in patients with AH could be part of a global epigenetic remodeling. A disease-specific increase was found in the expression of genes encoding DNA methyl transferases DNMT1 and DNMT3A, histone deacetylases HDAC7 and SMARC4 and histone acetyl transferases KAT6A and KAT6B. The methylation status of nearly 800,000 loci in normal livers and livers from AH patients was analyzed and found around 3,000 differentially methylated (DM) CpG-containing loci. Motif enrichment analysis of DM regions revealed the presence of HNF4α and PPAR-γ motifs in hypermethylated regions while hypomethylated regions were enriched in motifs of inflammatory transcriptional regulators, such as STAT4 and AP1 complex (c-FOS, JUN). The analysis of DM-CpG nearest genes with Ingenuity Pathway Analysis showed that among hypermethylated regions HNF4α footprint was the most enriched transcriptional regulator. These results mirrored data from RNA-seq analysis, showing a parallel between hypermethylation and down-regulation of regions controlled by LETFs (e.g., HNF4α, HNF1α, CEBPα, SREBPs, CEBPβ), and other hepatoprotective factors such as PPAR-γ (FIG. 4i-k). The analysis of soluble upstream regulators revealed TNFα and TGβ1 involvement in the expression of genes containing hypomethylated CpG (FIG. 4l). Lastly, data from H3K27Ac chromatin immunoprecipitation coupled to DNA sequencing (ChIP-seq) of normal livers and livers from patients with AH was analyzed. This chromatin mark is known to be enriched in active regulatory regions. Promoter regions of HNF4α targets such as PCK1, CYP3A4 and F7 were poor in H3K27Ac, whereas other gene promoter targets of RELA, like BCL2L1 and ICAM1 were rich in this mark. When focusing on HNF4A genomic locus, enhanced H3K27Ac mark was found in the P2 promoter, in accordance with our RNA expression results. Finally, whether the defective LETFs-depending gene expression in livers with AH results in an abnormal plasma footprint of the corresponding proteins was explored. Plasma was collected from controls and patients with AH and performed mass spectrometry. Among the 288 plasma proteins detected in plasma of both controls and AH patients, 60 corresponded to liver-secreted proteins whose gene expression was altered in AH livers. Importantly, 21 of these proteins belong to the footprint of LETFs altered in AH and correlated with hepatic gene expression. These peripheral footprints could be useful for prognosis, patient stratification or personalized treatment allocation in future clinical trials.

In conclusion, this human-based translational study found that the development of hepatocellular failure in patients with AH is characterized by a dramatic decrease in HNF4α-depending gene expression. The mechanisms likely involve TGβ1 that induces the use of HNF4α P2 promoter in hepatocytes, an effect attenuated by PPAR-γ agonists. Gene polymorphisms in LETFs including HNF4α do not predispose to the development of AH, while AH livers are characterized by profound changes in DNA methylation state and chromatin remodeling in HNF4α-dependent genes. The results of this study suggest that targeting TGβ1 and epigenetic drivers that modulate HNF4α-dependent gene expression could be beneficial in patients with AH.

Materials and Methods

Human RNAseq Studies

Human liver samples were obtained from the Human Biorepository Core from the NIHfunded international InTeam consortium (7U01AA021908-05). Patients with early alcoholic steatohepatitis (ASH) were obtained from Cliniques Universitaires Saint-Luc (Brussels, Belgium). All patients included gave written informed consent and the research protocols were approved by the local Ethics Committees. A total of 76 patients were included. Patients were selected according to different clinically relevant stage groups: 1) patients with early ASH, who were non-obese with high alcohol intake, and presented mild elevation of transaminases and histologic criteria of steatohepatitis (ASH, N=12); 2) patients with histologically confirmed alcoholic hepatitis (AH) who were biopsied before any treatment (AH, N=18) and 3) explants from patients with AH who underwent early transplantation following a well-defined protocol[1] (exAH, N=10). These groups were compared with fragments of non-diseased human livers (N=10), patients with nonalcoholic fatty liver disease (NAFLD) according to Keiner's Crieria[2] and without alcohol abuse (N=9) and from patients with non-cirrhotic HCV infection (N=9) and compensated HCV-related cirrhosis (N=9). Patients with malignancies were excluded from the study. A selection of liver samples from patients with AH (N=6) and fragments of normal human livers (N=5), were used for Methylome and ChIP seq analysis.

Patients for IHCs Analyses

Patients with normal liver and AH were obtained at the Division of Gastroenterology and Hepatology, Medical University of Graz, Austria. All patients had clinically and histologically confirmed AH (N=10) and did not have any concomitant causes of chronic liver disease (N=10)[4]. The study was approved by the Ethics Committee of the Medical University of Graz and performed in accordance with the Declaration of Helsinki.

RNA Extraction, Sequencing and Bioinformatic Analysis

Figure 1B:
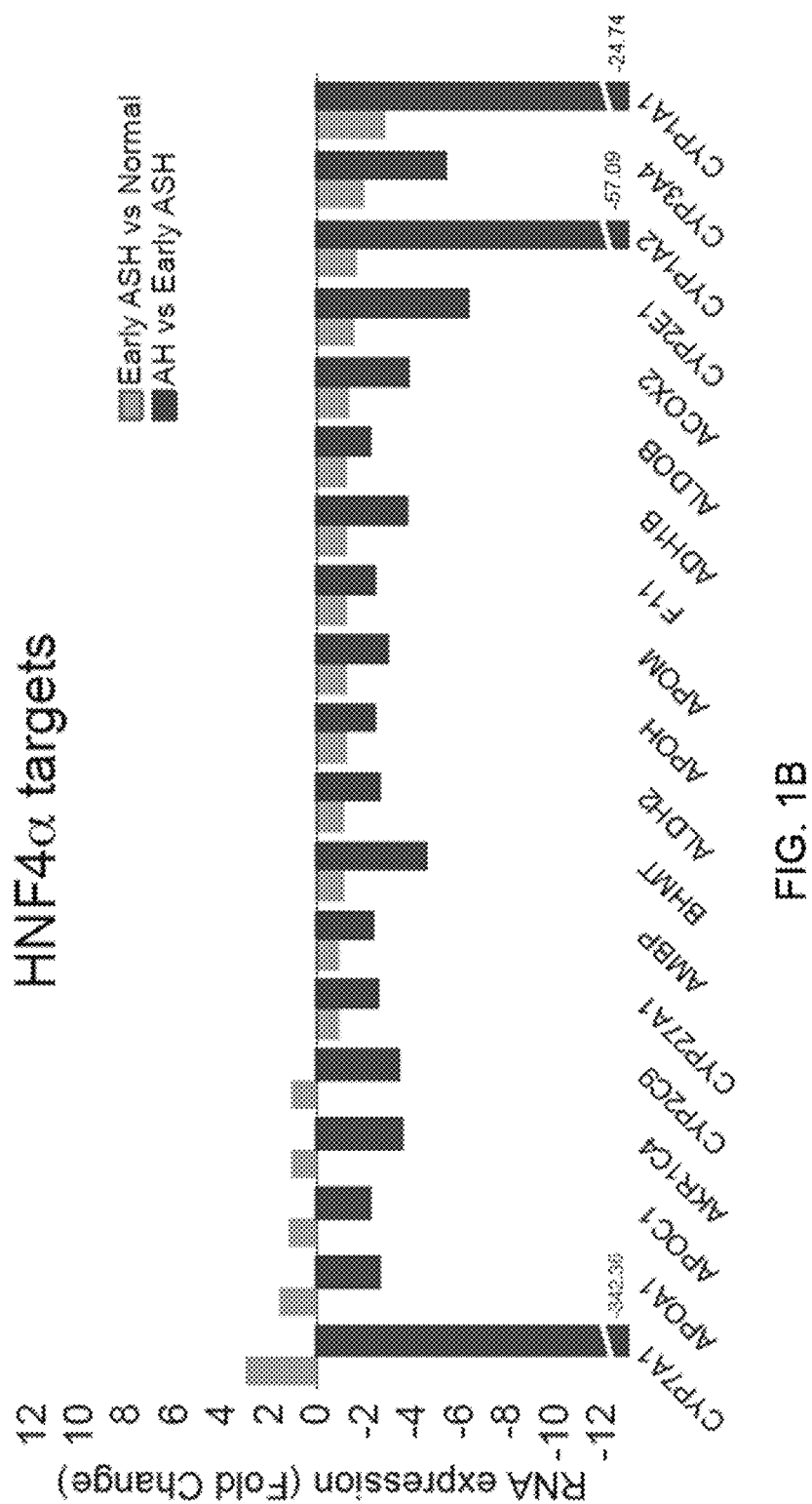

Total RNA from flash-frozen liver tissue was extracted by phenol/chloroform separation (TRIzol, Thermox). RNA purity and quality were assessed by automated electrophoresis (Bioanalyzer, Agilent) and was sequenced using Illumina HiSeq2000 platform. Libraries were built using TruSeq Stranded Total RNA Ribo-Zero GOLD (Illumina). Sequencing was paired end (2×100 bp) and multiplexed. Ninety-four paired-end sequenced samples obtained an average of 36.9 million total reads with 32.5 million (88%) mapped to GRCh37/hg19 human reference. Short read alignment was performed using STAR alignment algorithm with default parameters[5]. To quantify expression from transcriptome mappings we employed RSEM[6]. Principal component analysis (PCA) was done using made4 library[7]. Analysis of differential expression was performed using the Limma package[8]. Cyclic loess normalization was applied, followed by log transformation of the counts per million and mean-variance adjustment using the voom function. The Jonckheere-Terpstratest and Kendall correlation was used to check ordered differences gene among progressive disease stages. To agglomerate gene patterns along disease stages, Short Time-course Expression Miner (STEM) algorithm was used through on-line platform[9]. To uncover biological functions related to gene expression changes, Gene Ontology (GO) enrichment through gene set overlapping computation was done by means of Molecular Signatures Database v3.0, using the Canonical Pathways (CP) collection, which includes 1,329 gene sets[10]. To identify in an unbiased way the transcription factors predicted to be directly involved on transcriptomic changes we apply two methods: 1) Transcription factor motif searching in gene promoters and proximal 5' regulatory regions (−/+2,000 bp from TSS) by means of 2) Opossum on-line tool[11 and 2]) Functional prediction of differentially expressed genes (DEG) by the use of Ingenuity Pathway Analysis (IPA, Qiagen), selecting among predicted upstream regulators, those involved in transcriptional regulation (categories: "transcriptional regulator", "ligand-dependent nuclear receptor"). Only those hits found in both analyses were considered. The statistic approach used to calculate the predicted activation state (IPA) was Z Score (ZS) and is used to infer likely activation states of upstream regulators based on comparison with a model that assigns random regulation directions. An overlap p-value to determine statistically significant overlap between the transcription factor target gene dataset and the DEG of each comparison was also calculated, using Fisher's Exact Test. For this study, all the selected transcription factors (FIGS. 1b and 3f) shown an overlap p value <0.01 (data not shown). Opossum calculates two complementary scoring methods to measure the over-representation of transcription factor binding sites: (1) Z-scores measures the change in the relative number of TFBS motifs in the DEG gene set compared with the background set, and (2) Fisher scores based on a one-tailed Fisher exact probability assessing the number of genes with the TFBS motifs in the foreground set vs. the background set. JASPAR database was used as the source of DNA binding profiles.

HNF4a Gene Splicing Analysis

RNA-seq reads were trimmed to a uniform length of 75 bp using the FastxToolkit (http://hannonlab.cshl.edu/fastx_toolkit/). After read trimming, alignment of RNA-seq reads was performed with the STAR aligner (v2.5.2a) against the hg19 human genome. Resulting bam files were indexed with samtools for rMATS as described previously[12]. Differential expression of splice isoforms was completed using STAR alignment-StringTie-BallGown pipeline as described elsewhere[13]. To identify exon-specific expression, an alternate pipeline was used. First, reads were put through adapter trimming using TrimGalore (https://www.bioinformatics.babraham.ac.uk/projects/trim_galore/). After the trimming, reads were aligned with the STAR aligner (v2.5.2a) against the hg19 genome. The resulting bam files were then put through the DEXSeq R Bioconductor package (v1.26.0 for DEXSeq and 3.3.1 for R) pipeline. To obtain raw read counts for each exon, we used a standard DEXSeq script for exon counting (dexseq_count.py), with minor modifications. The exons were categorized in the GenCode v19 release. After exon counting, individual R scripts were used to obtain the exon-specific expression profiles. All custom scripts are available upon request.

Genomic DNA Methylome Analysis

Genomic DNA (gDNA) was extracted from flash-frozen liver tissue with PureLink Genomic DNA Mini Kit (Thermo) and quantified using Nanodrop (Thermo). 1 µg of isolated gDNA was bisulfite converted, denatured, fragmented and hybridized to Infinium Methylation Bead Chip, following the manufacturer protocol (Infinium Methylation-EPIC kit, Illumina). BeadChips were imaged using an Illumina Scan System and intensity was determined by iScan Control Software (Illumina). Sample intensities were normalized using functional normalization from the minfi package (v1.24.0)[14]. Probes failing a detection p-value threshold (0.01) in at least 50% of samples were removed, as were probes identified as containing a SNP with a MAF>0.05. Differentially methylated probes were identified by applying limma (v3.34.3)[8] contrasts to M values (absolute change in beta value >0.1, FDR-corrected Pvalue <0.05). Differentially methylated regions were identified using DMRcate (v1.14.0)[15] setting a threshold of absolute change in beta value in >0.1 and of Stouffer's value in <0.05.

Chromatin Immunoprecipitation-Deep Sequencing (ChIP-Seq)

ChIP-seq was performed in Mayo Epigenomics Development Laboratory as previously described[16]. ChIP-seq with the liver tissue from 5 controls and 7 severe AH explants (provided by University of Lille, France) were done for four histone modifications, including histone H3 acetylation (H3K27ac with anti-H3K27ac antibody (CST, #8173)). For the next-generation sequencing, ChIP-seq libraries were prepared from 10 ng of ChIP and input DNAs with the Ovation Ultralow DR Multiplex system (NuGEN). The ChIP-seq libraries were sequenced to 51 base pairs from both ends using the Illumina HiSeq 2000 in the Mayo Clinic Medical Genomics Core. Data were analyzed by the HiChIP pipeline[17]. Briefly, reads were aligned to the hg19 genome assembly using BWA and visualized using the Integrative Genomics Viewer (IGV). Mapped reads were post-processed to remove duplicates and pairs of reads mapping to multiple locations. The MACS2 and Sicer algorithm was used for peak-calling in relation to the input DNA. IGV was then used to visualize H3K27ac peak changes on individual genes in this study.

Human Primary Hepatocytes and Cell Lines

Primary human hepatocytes were purchased from Lonza. They were thawed in thawing medium (MCHT, Lonza), plated in plating medium (MP, Lonza), and cultured in maintenance medium (MM, Lonza). PHH were seeded on collagen-coated 12- or 6-well plates (Corning), allowed to attach for 4 hours, and then overlaid with Matrigel (0.3 mg/mL; Corning). In silencing experiments, transfection was done 6 h before Matrigel overlay and cells were kept in reduced serum media (OptiMEM, Gibco) during that time. Cells and/or supernatant were collected at the indicated time points. HepG2 cells and Hep3B cells were purchased from ATCC and were mycoplasma-free. They were expanded in Dulbecco's Minimum Essential Media (DMEM, Gibco) supplemented with 10% Fetal Bovine Serum (FBS, Gibco), 1 unit/mL Penicillin (Gibco), and 1 ug/mL Streptomycin (Gibco). When indicated, cells were serum-starved (1% FBS DMEM) 2 h prior drug incubation. In silencing experiments, transfection was done 24 h or 48 h before treatment and cells were kept in OptiMEM for 6 h after transfection and then in 1% FBS DMEM until harvesting.

RNA Extraction and Real Time Polymerase Chain Reaction (RT-PCR)

RNA from human biopsies, for RT-PCR experiments was extracted with Qiagen AllPrep DNA/RNA/Protein kit (Qiagen) following manufacturer's instructions. For experiments with cell lines and primary hepatocytes, RNA was extracted by phenol/chloroform method (TRIzol, Invitrogen). Concentration and purity was assessed by spectrophotometry (Nanodrop, Thermo). 1 µg of total RNA was used for reverse transcription reaction using Maxima First Strand cDNA Synthesis Kit for RT-qPCR with dsDNase (Thermo) following manufacturer protocol. RT PCR of 50 ng of cDNA was performed in a 96 well plate, using a CFX96 Real Time PCR detection system (BIO-RAD) and fluorescent double-stranded DNA-binding dye (SsoAdvanced Universal Sybr Green Supermix, BIO-RAD). The comparative CT method $(2-\Delta\Delta Ct)$ was used to determine fold changes in mRNA expression compared a control group after normalization to an endogenous reference gene (Human Histone3B3).

Protein Extraction and Western Blot

Liver tissue fragments and cell pellets were lysed in RIPA buffer (150 mM NaCl, 50 mM Tris pH 7.5, 0.1% SDS, 1% Triton X-100) with the addition of 40 mM DTT, protease inhibitor cocktail (Complete, Roche) and phosphatase inhibitors (1 mM $Na_3VO_4$, 2 mM NaF and 2 mM b-glycerophosphate) just before protein extraction. For liver extracts, ratio 1:20 (mg:V) was used, and tissue was pestle and sonicated (5 cycles of 20 sec with a probe sonicator at 20% Amplitude). In indicated cases, nuclear/cytoplasm fractionation was made by using the NE-PER kit (Thermo), following the manufacturer protocol. For western blot, 20-40 ug of protein extract was denatured with Laemli buffer (AlfaAesar), boiled (95° C. for 3 min), loaded in SDS-PAGE system (BIO-RAD), run until complete separation, transferred to a nitrocellulose membrane (0.2 um pore diameter, BIO-RAD). Membranes were blocked for 1 h at room temperature with 5% non-fat milk in 0.1% Tween20-Tris Buffered Saline (T-TBS). After overnight incubation with primary antibodies, membranes were washed three times with T-TBS and incubated with Near-Infrared Florescent secondary antibodies (IRDye 680 CW Goat anti-Rabbit and/or IRDye 800 CW Goat anti-Mouse, LiCOR) for 1 h at room temperature and washed twice with T-TBS and finally rinsed with TBS. Membranes were imaged using an Odissey CLx Imager (LiCOR).

Silencing and Overexpression of HNF4a Isoforms

For silencing of HNF4A-P2 isoforms, a specific custom siRNA and its Scramble (Scr) were generated by using BLOCK-iT RNAi Designer online tool (Thermo-Fisher). The sense-strand sequence of siRNA anti-HNF4A-P2 was GCTCCAGTGGAGAGTTCTTdTdT and that of Scr was GCTGAGTAGAGTGTCCCTT-dTdT. The effective working concentration of siRNA was 20 pM in primary hepatocytes and 10 pM in HepG2/Hep3B cells. Transfection of siRNAs was performed by the use of Lipofectamine-RNAiMAX (Invitrogen) following the manufacturer recommendations. This protocol showed 70-85% of silencing efficiency (mRNA and Protein level) at 24 and/or 48 h. For overexpression of HNF4a-P1 dependent isoforms, ORF of HNF4a2 was cloned in a pcDNA6 (Invitrogen) under the CMV promoter. Plasmid containing HNF4a8 ORF under CMV promoter, was gently provided from Dr. Bell (Pittsburgh Liver Research Center). Plasmids were transfected at the indicated doses in HepG2 cells using Lipofectamine 3,000 (Invitrogen) following standard manufacturer protocol.

Cell Culture Treatments

TGFb1 (5 ng/mL, R&D Systems) or amphiregulin (AREG, 50 nM, Sigma Aldrich) were added immediately before Matrigel overlay and mRNA or protein were collected at the indicated time points. For was used. For proteasome inhibition, MG132 (10 µM, Calbiochem-EMD Millipore) was added 45 min prior to cell harvesting. Treatments with TGF-β RI Kinase Inhibitor VI (5 nM, SB431542, Calbiochem-EMD Millipore), TAKI Inhibitor (0.5 or 1 µM, NG25 trihydrochloride, Axon), EGFR inhibitor (3 µM, PD153035, Calbiochem-EMD Millipore), MEK Inhibitor (10 µM, U0126, Promega), PPARg agonists, Rosiglitazone (10 µM, Sigma) and Pioglitazone (10 µM, Sigma), and Dexamethasone (0.25 µM, Sigma), was performed after of 2 h starvation (1% FBS DMEM) and 45 min before TGFb1 treatment.

Biliary Acid Quantification

Cryopreserved human primary hepatocytes (Lonza) were plated overnight on collagen coated 96-well plates at 2×104 cells per well in MM (Lonza) and collected after 24 and 48 h of siRNA transfection. Total bile acids were measured following the protocol supplied in the Total Bile Acid Assay Kit available from Cell Biolabs (San Diego, Ca). Absorbance data was collected using the SpectraMax M2 (Molecular Devices, Sunnyvale, CA, USA) microtiter plate reader. The total bile acids were calculated by extrapolating test values to a calibration curve as described in the assay kit.

Glucose Production Assay

Cryopreserved human primary hepatocytes (Lonza) were plated overnight on collagen coated 12-well plates at 1×105 cells per well in MM (Lonza). Twenty-four hours after plating, cells were serum-starved in DMEM base medium (Sigma) supplemented with 1 g/L glucose (Sigma), 3.7 g/L sodium bicarbonate (Sigma), and 4 mM L-glutamine (Corning) overnight, followed by 24 hours incubation in 0.3 ml glucose-production medium: DMEM base with 2 mM glutamine, 3.7 g/L sodium bicarbonate, 15 mM HEPES (ThermoFisher), 20 mM lactate (Sigma), 2 mM pyruvate (Fisher) and 0.1 mM pCPT-cAMP (Sigma). After 24 hours, 50 µL of medium was removed for glucose detection with Invitrogen Glucose Colorimetric Detection kit (#EIAGLUC), according to manufacturer's protocol, and read on a plate reader (Multiskan G O, Thermo-Scientific).

Model of Alcoholic Liver Disease

Animals: Male mice (C57BL/6J, 20-25 g, 12 weeks of age) were obtained from the Jackson Laboratory (Bar Harbor, ME) and housed in a temperature-controlled environment with a 12-h light-dark cycle and were given free access to regular laboratory chow diet and water. All studies were approved by the Institutional Animal Care and Use Committee at UNC-Chapel Hill.

Diets and Treatment: CCl4 (>99.5% pure) and olive oil vehicle were from Sigma (St. Louis, MO), ethyl alcohol (EtOH) (190 proof, Koptec) was from VWR (Radnor, PA). Procedures for CCl4-induced liver fibrosis were as detailed elsewhere[18]. Mice were intraperitoneally injected (15 ml/kg) with CCl4 (0.2 ml/kg) or olive oil vehicle-alone 2× week for 6 weeks. After 6 weeks of CCl4 treatment, animals underwent surgical intragastric intubation[19]. Following surgery, mice were housed in individual metabolic cages and allowed one week to recover with ad libitum access to food and water. Animals had free access to water and non-nutritious cellulose pellets throughout the remaining study. Alcohol groups received high-fat diet containing ethyl alcohol as detailed elsewhere[19]. Alcohol was delivered continuously through the intragastric cannula initially at 16 g/kg/day and was gradually increased to 25 g/kg/day. All animals were given humane care in compliance with the National Institutes of Health guidelines and alcohol intoxication was assessed to evaluate the development of tolerance. At the end of the study, mice were anesthetized with pentobarbital (50 mg/kg, i.p.) and sacrificed via exsanguination through the vena cava, which was the site of blood collection. Tissues were excised and snap-frozen in liquid nitrogen.

Immunohistochemistry

Dewaxed 3 µm thick sections were stained with hematoxylin and eosin (H&E) or chromatrope aniline blue (CAB) connective tissue stain according to standard protocols. All slides were reviewed by a single pathologist (CL). For immunohistochemistry paraffin sections were dewaxed and rehydrated. After immunohistochemical staining sections were counterstained with hematoxylin (Labonord, Templemars, France) and mounted with Aquatex (Merck, Darmstadt, Germany). Immunohistochemical signals were evaluated semi-quantitatively by the application of numerical scores, based on the intensity of the signal. For HNF4a, HNF1a and FOXA1, where the signal in AH patients was also cytoplasmic, scoring was made separately for cytoplasmatic and nuclear signals.

Single Nucleotide Polymorphism (SNP) Analysis

Patients with AH (n=878) were recruited through the steroids or pentoxifylline for alcoholic hepatitis (STOPAH) trial[20]. Inclusion was based upon a clinical diagnosis of alcoholic hepatitis, modified Maddrey's discriminant (mDF) ≥32, current excess alcohol consumption, recent onset of jaundice and exclusion of other causes of decompensated liver disease[21]. Controls with a background of alcohol dependence but with no evidence of liver injury were recruited via the University College London Consortium (N=318). All were of English, Scottish, Welsh or Irish descent with a maximum of one grandparent of white European Caucasian origin. None of the individuals was related. The alcoholic cirrhosis study data were obtained from a genome-wide association study of alcohol-related cirrhosis with data from a total of 2,178 individuals[22]. Publicly available study summary data were downloaded from gengastro.med.tudresden. de/suppl/alc_cirrhosis/. There was known overlap between the control populations of the alcoholic hepatitis study and United Kingdom cohort of the alcoholic cirrhosis study. Samples were genotyped using the HumanCoreExome beadchip (Illumina) at the Wellcome Trust Sanger Institute (Cambridge, UK). Quality control and analysis of data were performed in PLINK v1.90. Individual data were quality controlled such that those with genotyping rate <98%, sample heterozygosity >3 standard deviations from the population mean, relatedness determined by pi-hat >0.185 or phenotypic and genotypic sex mismatch were excluded. Markers with genotyping rate <98% or with a probability of deviation from Hardy-Weinberg equilibrium <$10^6$ were also excluded. Population principal components were calculated using a linkage-disequilibrium pruned data set of common variants in PLINK v1.90, associations between principal components and case-control status were tested using R. The principal components associated with case-control status were specified as covariates in analyses. Key transcription factors and related genes were identified through the primary analysis of RNA-seq data. Genomic coordinates for the coding regions of these genes were obtained from ensembl Biomart. Single nucleotide polymorphisms (SNPs) falling within these genetic loci were extracted from the alcoholic hepatitis study data. Analyses were limited to SNPs with a minor allele frequency >1%. Study significance was set through application of a Bonferroni correction for the number of tests performed for a=0.05. For significantly associated SNPs predicted effects on protein structure were predicted using SIFT[23] and Polyphen[24], expression quantitative train locus (eQTL) tests were conducted using GTeX[25]. The SNPs most significantly associated with disease risk at each locus were further examined in the alcohol-related cirrhosis dataset. Gene- and pathway-based association tests were performed using study summary statistics in MAGMA v1.06[26]. Study-specific significance threshold was set using a=0.05 corrected for the number of genes evaluated using the Bonferroni method. Pathway-based association testing was achieved by defining a biological pathway incorporating the gene target of interest.

Mass Spectrometry of Plasma Samples (LC-MS/MS)

Plasma samples from Control subjects (N=10, 10 µL each) and plasma from patients with AH (N=15, 10 µL each) were pooled and protein concentration of each group was determined by Qubit fluorometry. 10 µL of protein from each pooled sample was depleted in duplicate on a Pierce™ Top 12 Abundant Protein Depletion Spin Column (Thermo Scientific) according to manufacturer's protocol. Depleted samples were buffer exchanged into water on a centrifugal concentrator (Spin X, Corning) using a 5 kD molecular weight cut off and quantified by Qubit fluorometry (Life Technologies). 50 µg of each sample was reduced with dithiothreitol, alkylated with iodoacetamide and digested overnight with trypsin (Promega). The digestion was terminated with formic acid. Each digested sample was processed by solid phase extraction using an Empore C18 (3M) plate under vacuum (5 in Hg). Briefly, columns were activated with 400 µL 95% acetonitrile/0.1% TFA×2, and then equilibrated with 400 µL 0.1% TFA×4. Acidified samples were samples were loaded and columns were washed with 400 µL 0.1% TFA×2. Peptides were eluted with 200 µL 70% acetonitrile/0.1% TFA×2 and then lyophilized for further processing. 2 µg of each sample was analyzed by nano LC-MS/MS with a NanoAcquity HPLC system (Waters) interfaced to a Q Exactive (Thermo-Fisher). Peptides were loaded on a trapping column and eluted over a 75 µm analytical column at 350 nL/min using a 3 hr reverse phase gradient. Columns were packed with Luna C18 resin (Phenomenex). The mass spectrometer was operated in data-dependent mode, with the Orbitrap operating at 60,000 FWHM and 17,500 FWHM for MS and MS/MS respectively. The fifteen most abundant ions were selected for MS/MS. Data were searched using a local copy of Mascot with the following parameters: Enzyme: Trypsin/P; Database: SwissProt Human. Fixed modification: Carbamidomethyl (C); Variable modifications: Oxidation (M), Acetyl (N-term), Pyro-Glu (N-term Q), Deamidation (N/Q); Mass values: Monoisotopic; Peptide Mass Tolerance: 10 ppm; Fragment Mass Tolerance: 0.02 Da; Max Missed Cleavages: 2. Mascot DAT files were parsed into Scaffold (Proteome Software) for validation, filtering and to create a non-redundant list per sample. Data were filtered using at 1% protein and peptide FDR and requiring at least two unique peptides per protein. Normalized Spectral Abundance Factor (NSAF) values were used to obtain the fold change between Normal and AH groups. For unbiased searching of secreted protein coding genes from RNA-seq data, Retrieve/ID mapping online tool of UniProt was used (filters "signal peptide" and "NOT transmembrane domain")[27].

REFERENCES (MATERIAL & METHODS)

1. Mathurin, P., et al. Early liver transplantation for severe alcoholic hepatitis. N Engl J Med 365, 1790-1800 (2011).
2. Kleiner, D. E., et al. Design and validation of a histological scoring system for nonalcoholic fatty liver disease. Hepatology 41, 1313-1321 (2005).
3. Louvet, A., et al. The Lille model: a new tool for therapeutic strategy in patients with severe alcoholic hepatitis treated with steroids. Hepatology 45, 1348-1354 (2007).
4. Lackner, C., et al. Histological parameters and alcohol abstinence determine long-term prognosis in patients with alcoholic liver disease. J Hepatol 66, 610-618 (2017).
5. Dobin, A., et al. STAR: ultrafast universal RNA-seq aligner. Bioinformatics 29, 15-21 (2013).
6. Li, B. & Dewey, C. N. RSEM: accurate transcript quantification from RNA-Seq data with or without a reference genome. BMC Bioinformatics 12, 323 (2011).
7. Culhane, A. C., Thioulouse, J., Perriere, G. & Higgins, D. G. MADE4: an R package for multivariate analysis of gene expression data. Bioinformatics 21, 2789-2790 (2005).
8. Ritchie, M. E., et al. limma powers differential expression analyses for RNA-sequencing and microarray studies. Nucleic Acids Res 43, e47 (2015).
9. Ernst, J. & Bar-Joseph, Z. STEM: a tool for the analysis of short time series gene expression data. BMC Bioinformatics 7, 191 (2006).
10. Liberzon, A., et al. Molecular signatures database (MSigDB) 3.0. Bioinformatics 27, 1739-1740 (2011).
11. Ho Sui, S. J., Fulton, D. L., Arenillas, D. J., Kwon, A. T. & Wasserman, W. W. oPOSSUM: integrated tools for analysis of regulatory motif over-representation. Nucleic Acids Res 35, W245-252 (2007).

12. Shen, S., et al. rMATS: robust and flexible detection of differential alternative splicing from replicate RNA-Seq data. Proc Natl Acad Sci USA 111, E5593-5601 (2014).
13. Pertea, M., Kim, D., Pertea, G. M., Leek, J. T. & Salzberg, S. L. Transcript-level expression analysis of RNA-seq experiments with HISAT, StringTie and Ballgown. Nat Protoc 11, 1650-1667 (2016).
14. Aryee, M. J., et al. Minfi: a flexible and comprehensive Bioconductor package for the analysis of Infinium DNA methylation microarrays. Bioinformatics 30, 1363-1369 (2014).
15. Peters, T. J., et al. De novo identification of differentially methylated regions in the human genome. Epigenetics Chromatin 8, 6 (2015).
16. Zhong, J., et al. Purification of nanogram-range immunoprecipitated DNA in ChIP-seq application. BMC Genomics 18, 985 (2017).
17. Yan, H., et al. HiChIP: a high-throughput pipeline for integrative analysis of ChIP-Seq data. BMC Bioinformatics 15, 280 (2014).
18. Uehara, T., Pogribny, I. P. & Rusyn, I. The DEN and CCl4-Induced Mouse Model of Fibrosis and Inflammation-Associated Hepatocellular Carcinoma. Curr Protoc Pharmacol 66, 14 30 11-10 (2014).
19. Kono, H., et al. Development of an intragastric enteral model in the mouse: studies of alcohol-induced liver disease using knockout technology. J Hepatobiliary Pancreat Surg 7, 395-400 (2000).
20. Thursz, M. R., Forrest, E. H., Ryder, S. & investigators, S. Prednisolone or Pentoxifylline for Alcoholic Hepatitis. N Engl J Med 373, 282-283 (2015).
21. Forrest, E. H. & Lucey, M. R. Rescue liver transplantation for severe alcoholic hepatitis: arriving where we started? Hepatology 57, 10-12 (2013).
22. Buch, S., et al. A genome-wide association study confirms PNPLA3 and identifies TM6SF2 and MBOAT7 as risk loci for alcohol-related cirrhosis. Nat Genet 47, 1443-1448 (2015).
23. Vaser, R., Adusumalli, S., Leng, S. N., Sikic, M. & Ng, P. C. SIFT missense predictions for genomes. Nat Protoc 11, 1-9 (2016).
24. Adzhubei, I. A., et al. A method and server for predicting damaging missense mutations. Nat Methods 7, 248-249 (2010).
25. Consortium, G. T. The Genotype-Tissue Expression (GTEx) project. Nat Genet 45, 580-585 (2013).
26. de Leeuw, C. A., Mooij, J. M., Heskes, T. & Posthuma, D. MAGMA: generalized gene-set analysis of GWAS data. PLoS Comput Biol 11, e1004219 (2015).
27. Apweiler, R., et al. UniProt: the Universal Protein knowledgebase. Nucleic Acids Res 32, D115-119 (2004).

The following numbered clauses describe various aspects or embodiments of the present invention:

Clause 1: A method of treating a patient having liver damage or liver failure, comprising knocking down or inhibiting expression of a hepatocyte nuclear factor 4 alpha mRNA transcribed from its P2 promoter (HNF4α-P2 isoform mRNA) in the patient, or reducing activity of the protein encoded by the HNF4α-P2 isoform mRNA, thereby treating the liver damage or liver failure in the patient.

Clause 2: The method of clause 1, wherein the liver damage or liver failure is acute liver failure.

Clause 3: The method of clause 1, wherein the liver damage or liver failure is associated with alcohol-related liver disease (ALD), alcoholic hepatitis (AH), or Acute-on-Chronic Liver Failure (ACLF).

Clause 4: The method of any one of clauses 1-3, wherein the treatment normalizes or decreases blood bilirubin levels, normalizes or decreases prothrombin time, and/or normalizes or increases serum albumin.

Clause 5: The method of any one of clauses 1-4, wherein an RNAi agent for knocking down or inhibiting expression of an HNF4α-P2 isoform mRNA is administered to the patient in an amount effective to treat the liver damage or liver failure in a patient.

Clause 6: A method of knocking down expression of an HNF4α-P2 isoform mRNA in a cell, comprising contacting the cell with an RNAi agent for selectively knocking down expression of an HNF4α-P2 isoform mRNA, in an amount effective to reduce production of the protein product of the HNF4α-P2 isoform mRNA in a cell.

Clause 7: The method of clause 6, wherein the cell is a liver cell.

Clause 8: The method of clause 6 or 7, wherein the cell is a human cell.

Clause 9: The method of any one of clauses 6-8, wherein the cell is in vitro.

Clause 10: The method of any one of clauses 6-8, wherein the cell is in vivo.

Clause 11: The method of any one of clauses 5-10, wherein the RNAi agent targets a contiguous sequence of 15 or more bases within bases 1-63, or within bases 1-53 of SEQ ID NO: 1.

Clause 12: The method of clause 11, wherein the RNAi agent targets a contiguous sequence of 15 or more bases within the sequence: GCTCCAGTGGAGAGTTCTTACGACACG (SEQ ID NO: 1, bases 32-58).

Clause 13: The method of clause 12, wherein the RNAi agent targets the sequence: GCTCCAGTGGAGAGTTCTT (SEQ ID NO: 1, bases 32-50), CTCCAGTGGAGAGTTCTTA (SEQ ID NO: 1, bases 33-51), TCCAGTGGAGAGTTCTTAC (SEQ ID NO: 1, bases 34-52), or GGAGAGTTCTTACGACAC (SEQ ID NO: 1, bases 40-57).

Clause 14: The method of any one of clauses 5-11, wherein the sense strand of the RNAi agent has the sequence GCTCCAGTGGAGAGTTCTTdTdT (SEQ ID NO: 30), CTCCAGTGGAGAGTTCTTAdTdT (SEQ ID NO: 32), TCCAGTGGAGAGTTCTTACdTdT (SEQ ID NO: 34), or GGAGAGTTCTTACGACACdTdT (SEQ ID NO: 36).

Clause 15: The method of any one of clauses 5-11, wherein the RNAi agent is chosen from GCTCCAGTGGAGAGTTCTTdTdT (SEQ ID NO: 30), CGTGTCGTAAGAACTCTCCdTdT (SEQ ID NO: 31), gscstccaGftGfGfAfgagttcttL96 (SEQ ID NO: 6), or asAfsgaaCfuCfUfccacUfgGfagcscsc (SEQ ID NO: 7).

Clause 16: The method of any one of clauses 5-13, wherein one or both strands of the RNAi agent comprises one or more dT residues at its 3' end.

Clause 17: The method of any one of clauses 5-13, wherein one or both strands of the RNAi agent comprises one or more modified bases.

Clause 18: The method of clause 17, wherein one or both strands of the RNAi agent is chemically modified at its 3' end with L96 (N-[tris(GalNAc-alkyl)-amidodecanoyl]-4-hydroxyprolinol (Hyp-(GalNAc-alkyl)$_3$).

Clause 19: The method of clause 2 or 3, wherein a RNAi reagent comprises a sense or antisense strand as depicted in FIG. 7A.

Clause 20: The method of any one of clauses 1-19, wherein an RNAi agent is used for knocking down or inhibiting expression of an HNF4α-P2 isoform mRNA, and wherein the target sequence of the RNAi agent is a human sequence.

Clause 21: The method of any one of clauses 1-20, wherein an RNAi agent is used for knocking down or inhibiting expression of an HNF4α-P2 isoform mRNA, and wherein the RNAi agent is delivered parenterally to a patient.

Clause 22: The method of any one of clauses 1-21, wherein liver cells are targeted for knock-down of an HNF4α-P2 isoform mRNA.

Clause 23: The method of any one of clauses 1-22, for treatment of a patient, wherein the patient is a human.

Clause 24: The method of any one of clauses 1-23, wherein an iRNAi reagent is used to knock down expression of an HNF4α-P2 isoform mRNA in the patient.

Clause 25: The method of clause 24, wherein the expression of an HNF4α-P1 isoform mRNA in the patient is not substantially affected by knocking down expression of the HNF4α-P2 isoform mRNA in the patient.

Clause 26: The method of any one of clauses 1-25, further comprising administering to the patient, or contacting the cells with, a second active agent for treatment of liver damage or liver failure in a patient.

Clause 27: A RNAi agent targeting exon 1D of HFN4α.

Clause 28: The RNAi agent of clause 27, targeting 15-30 bases of bases 1-63 of SEQ ID NO: 1.

Clause 29: The RNAi agent of clause 27, comprising a sense strand having the sequence of at least 15 contiguous bases of GCTCCAGTGGAGAGTTCTTACGACACG (SEQ ID NO: 1, bases 32-58).

Clause 30: The RNAi agent of clause 29, wherein the sense strand has the sequence GCTCCAGTGGAGAGTTCTT (SEQ ID NO: 1, bases 32-50), CTCCAGTGGAGAGTTCTTA (SEQ ID NO: 1, bases 33-51), TCCAGTGGAGAGTTCTTAC (SEQ ID NO: 1, bases 34-52), or GGAGAGTTCTTACGACAC (SEQ ID NO: 1, bases 40-57).

Clause 31: The RNAi agent of any one of clauses 27-30, wherein one or both strands of the RNAi agent comprises one or more, e.g., two, dT residues at its 3' end.

Clause 32: The RNAi agent of any one of clauses 27-30, wherein one or both strands of the RNAi agent comprises one or more modified bases.

Clause 33: The RNAi agent of clause 32, wherein the sense strand has the sequence: GCTCCAGTGGAGAGTTCTTdTdT (SEQ ID NO: 30), CTCCAGTGGAGAGTTCTTAdTdT (SEQ ID NO: 32), TCCAGTGGAGAGTTCTTACdTdT (SEQ ID NO: 34), or GGAGAGTTCTTACGACACdTdT (SEQ ID NO: 36).

Clause 34: The RNAi agent of any one of clauses 27-30, wherein the RNAi agent is chosen from GCTCCAGTGGAGAGTTCTTdTdT (SEQ ID NO: 30), CGTGTCGTAAGAACTCTCCdTdT (SEQ ID NO: 31), gscstccaGftGfGfAfgagttcttL96 (SEQ ID NO: 6), or asAfsgaaCfuCfUfccacUfgGfagcscsc (SEQ ID NO: 7).

Clause 35: The RNAi agent of clause 27, comprising a sense or antisense strand as depicted in FIG. 7A.

Clause 36: The RNAi agent of any one of clauses 27-30, wherein the RNAi agent is chemically-modified.

Clause 37: The RNAi agent of clause 36, wherein one or both strands of the RNAi agent is chemically modified at its 3' end with L96 (N-[tris(GalNAc-alkyl)-amidodecanoyl)]-4-hydroxyprolinol (Hyp-(GalNAc-alkyl)$_3$).

Having described this invention, it will be understood to those of ordinary skill in the art that the same can be performed within a wide and equivalent range of conditions, formulations and other parameters without affecting the scope of the invention or any embodiment thereof. References incorporated herein by reference are incorporated for their technical disclosure and only to the extent that they are consistent with the present disclosure.

What is claimed is:

1. A method of treating a patient having liver damage or liver failure, comprising administering to the patient a RNAi agent selected from the group consisting of:
- a contiguous sequence of 15-30 bases within SEQ ID NO: 44;
- SEQ ID NO: 38;
- SEQ ID NO: 39;
- SEQ ID NO: 40;
- SEQ ID NO: 41;
- SEQ ID NO: 42;
- SEQ ID NO: 43;
- SEQ ID NO: 30;
- SEQ ID NO: 31;
- SEQ ID NO: 32;
- SEQ ID NO: 33;
- SEQ ID NO: 34;
- SEQ ID NO: 35;
- SEQ ID NO: 36;
- SEQ ID NO: 37;
- SEQ ID NO: 6; and
- SEQ ID NO: 7,
  in an amount effective to knock down or inhibit expression of a hepatocyte nuclear factor 4 alpha mRNA transcribed from its P2 promoter (HNF4α-P2 isoform mRNA) in the patient, or reducing activity of the protein encoded by the HNF4α-P2 isoform mRNA, thereby treating the liver damage or liver failure in the patient.

2. The method of claim 1, wherein the liver damage or liver failure is acute liver failure or is associated with alcohol-related liver disease (ALD), alcoholic hepatitis (AH), or Acute-on-Chronic Liver Failure (ACLF).

3. The method of claim 1, wherein the treatment normalizes or decreases blood bilirubin levels, normalizes or decreases prothrombin time, and/or normalizes or increases serum albumin.

4. The method of claim 1, wherein expression of an HNF4α-P1 isoform mRNA in the patient is not substantially affected by knocking down expression of the HNF4α-P2 isoform mRNA in the patient.

5. The method of claim 1, wherein the RNAi agent is administered parenterally.

6. The method of claim 1, further comprising administering to the patient a second active agent for treatment of liver damage or liver failure in a patient.

7. A RNAi agent targeting SEQ ID NO: 1 and selected from the group consisting of:
- a contiguous sequence of 15-30 bases within SEQ ID NO: 44;
- SEQ ID NO: 38;
- SEQ ID NO: 39;
- SEQ ID NO: 40;
- SEQ ID NO: 41;
- SEQ ID NO: 42;
- SEQ ID NO: 43;
- SEQ ID NO: 30;
- SEQ ID NO: 31;
- SEQ ID NO: 32;
- SEQ ID NO: 33;
- SEQ ID NO: 34;
- SEQ ID NO: 35;
- SEQ ID NO: 36;
- SEQ ID NO: 37;
- SEQ ID NO: 6; and
- SEQ ID NO: 7,
  wherein the RNAi agent selectively knocks down expression of hepatocyte nuclear factor 4α-P2 (HNF4α-P2) isoform mRNA in a cell to which the RNAi agent is administered.

* * * * *